United States Patent
Aqad

(10) Patent No.: US 12,140,866 B2
(45) Date of Patent: Nov. 12, 2024

(54) PHOTOACID GENERATORS, PHOTORESIST COMPOSITIONS, AND PATTERN FORMATION METHODS

(71) Applicant: Rohm and Haas Electronic Materials LLC, Marlborough, MA (US)

(72) Inventor: Emad Aqad, Northborough, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 274 days.

(21) Appl. No.: 17/454,331

(22) Filed: Nov. 10, 2021

(65) Prior Publication Data

US 2022/0214614 A1 Jul. 7, 2022

Related U.S. Application Data

(60) Provisional application No. 63/133,189, filed on Dec. 31, 2020.

(51) Int. Cl.

| | | |
|---|---|---|
| G03F 7/004 | (2006.01) | |
| C07C 51/02 | (2006.01) | |
| C07C 303/32 | (2006.01) | |
| C07C 309/12 | (2006.01) | |
| C07C 381/12 | (2006.01) | |
| C08F 220/30 | (2006.01) | |
| G03F 7/039 | (2006.01) | |
| G03F 7/20 | (2006.01) | |
| G03F 7/30 | (2006.01) | |
| G03F 7/32 | (2006.01) | |

(52) U.S. Cl.
CPC ............ *G03F 7/0045* (2013.01); *C07C 51/02* (2013.01); *C07C 303/32* (2013.01); *C07C 309/12* (2013.01); *C07C 381/12* (2013.01); *C08F 220/303* (2020.02); *G03F 7/2004* (2013.01); *G03F 7/30* (2013.01); *G03F 7/322* (2013.01)

(58) Field of Classification Search
CPC ... C07C 303/32; C07C 381/12; C07C 309/12; C07C 51/02; C07C 381/32; G03F 7/322; G03F 7/0045; G03F 7/004; G03F 7/20; G03F 7/029; G03F 7/0382; G03F 7/26; G03F 7/0392; C08F 220/303
See application file for complete search history.

(56) References Cited

U.S. PATENT DOCUMENTS

| | | | |
|---|---|---|---|
| 2003/0113658 A1* | 6/2003 | Ebata | ....................... G03F 7/038 430/270.1 |
| 2008/0248422 A1 | 10/2008 | Iwai et al. | |
| 2008/0311522 A1 | 12/2008 | Iwai et al. | |
| 2014/0080058 A1* | 3/2014 | Cameron | ................. G03F 7/027 430/281.1 |
| 2014/0080060 A1* | 3/2014 | LaBeaume | ............ G03F 7/0382 430/281.1 |
| 2014/0120471 A1* | 5/2014 | Aqad | ..................... C07C 321/10 430/285.1 |
| 2014/0186767 A1* | 7/2014 | Thackeray | ............... G03F 7/004 430/281.1 |
| 2014/0295347 A1 | 10/2014 | Aqad et al. | |
| 2015/0093708 A1 | 4/2015 | LaBeaume | |
| 2015/0093709 A1* | 4/2015 | LaBeaume | .............. G03F 7/027 430/325 |
| 2019/0155152 A1* | 5/2019 | Aqad | ..................... G03F 7/0045 |

FOREIGN PATENT DOCUMENTS

| | | | |
|---|---|---|---|
| JP | 2005189501 A | 7/2007 | |
| JP | 2013-116885 A | 6/2013 | |
| JP | 2014-40387 A | 3/2014 | |
| KR | 20190080769 A * | 7/2019 | ........... C07C 303/32 |

OTHER PUBLICATIONS

Translated Description from Takashi (Year: 2019).*
Translated Claims from Takashi (Year: 2019).*

* cited by examiner

*Primary Examiner* — John S Chu
(74) *Attorney, Agent, or Firm* — Jonathan D. Baskin

(57) ABSTRACT

Photoacid generators comprising a moiety of formula (1):

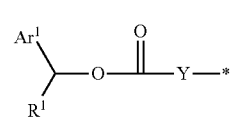

(1)

wherein: $Ar^1$ is a substituted or unsubstituted aryl group; $R^1$ is an alkyl or aryl group, each of which may be substituted or unsubstituted, wherein $Ar^1$ and $R^1$ are optionally connected together by a single bond or a divalent linking group to form a ring; Y is a single bond or a divalent group; and * is the point of attachment of the moiety to another atom of the photoacid generator. The photoacid generator compounds find particular use in photoresist compositions that can be used to form lithographic patterns for the formation of electronic devices.

6 Claims, No Drawings

PHOTOACID GENERATORS, PHOTORESIST COMPOSITIONS, AND PATTERN FORMATION METHODS

This application claims the benefit of priority under 35 U.S.C. § 119 (e) to U.S. Provisional Application No. 63/133,189, filed Dec. 31, 2020, the entire contents of which are incorporated herein by reference.

BACKGROUND OF THE INVENTION

1. Field of the Invention

The invention relates generally to the manufacture of electronic devices. More specifically, this invention relates to photoacid generators (PAGs), to photoresist compositions containing the PAGs, and to pattern formation methods using the photoresist compositions. The PAGs, photoresist compositions, and patterning methods find particular use in the formation of lithographic patterns useful in the manufacture of semiconductor devices.

2. Description of the Related Art

Photoresist compositions are photosensitive materials used to transfer a pattern to one or more underlying layers, such as a metal, semiconductor, or dielectric layer disposed on a substrate. Positive-tone chemically amplified photoresist compositions are conventionally used for high-resolution processing. Such resist compositions typically include a polymer having acid-labile groups and a photoacid generator (PAG). A layer of the photoresist composition is patternwise exposed to activating radiation and the PAG generates an acid in the exposed regions. During post-exposure baking, the acid causes cleavage of the polymer's acid-labile groups. This creates a difference in solubility characteristics between exposed and unexposed regions of the photoresist layer in a developer solution. In a positive tone development (PTD) process, exposed regions of the photoresist layer become soluble in a developer, typically an aqueous base developer, and are removed from the substrate surface. Unexposed regions, which are insoluble in the developer, remain after development to form a positive relief image. The resulting relief image permits selective processing of the substrate.

To increase the integration density of semiconductor devices and allow for the formation of structures having dimensions in the nanometer (nm) range, photoresists and photolithography processing tools having high-resolution capabilities have been and continue to be developed. One approach to achieving nm-scale feature sizes in semiconductor devices is the use of activating radiation having a short wavelength, for example, 193 nm or less, for exposure of the photoresist layer. To further improve lithographic performance, immersion lithography tools have been developed to effectively increase the numerical aperture (NA) of the lens of the imaging device, for example, a scanner having an ArF (193 nm) light source. This is accomplished by use of a relatively high refractive index fluid, typically water, between the last surface of the imaging device and the upper surface of the semiconductor wafer.

ArF immersion tools are currently pushing the boundaries of lithographic processing to the 16 nm and 14 nm device nodes with the use of multiple (double, triple, or higher order) patterning techniques. The use of multiple patterning, however, can be costly in terms of increased material usage and number of process steps required as compared with single step, directly-imaged patterns. The need for photoresist compositions for next-generation (e.g., EUV) lithography has thus become of increased importance for advanced device nodes. At the extreme feature sizes associated with these nodes, the performance requirements of photoresist compositions has become increasingly more stringent. Desired performance properties include, for example, high sensitivity to activating radiation, low unexposed film thickness loss (UFTL), good contrast, high-resolving capability, low surface roughness, good critical dimension uniformity (CDU), and minimal patterning defects.

Typical PAG compounds used in advanced photoresist compositions include an anion, which is the conjugated base of an acid to be photo-generated, and an onium cation that is hydrophobic. Hydrophobicity of the cation, however, can result in poor dissolution in the exposed regions of the resist layer during aqueous base development. This can lead to patterning defects, which can adversely impact device performance and product yield. Hydrophobic cations can further result in instability of the post-exposure latent image, which can negatively affect the profile of the resist pattern formed after development.

To address developer PAG solubility issues, an acid-labile group can be included on the cation. Cleavage of the acid-labile group in exposed regions of the photoresist layer during post-exposure bake produces a hydrophilic group on the cation, thereby increasing solubility in an aqueous base developer. The use of PAG cations that include an acid-labile group in photoresist compositions has been proposed. US 2008/0248422 A1, for example, discloses PAG cations comprising an acid dissociable dissolution inhibiting group. Examples of such groups are disclosed as including cyclic or linear tertiary alkyl ester groups and acetal-type groups. Given current performance criteria and chemistries for photoresists at advanced device nodes, the provision of new photoacid generators would be desired.

There is a need in the art for photoacid generators, photoresist compositions, and pattern formation methods which address one or more problems associated with the state of the art.

SUMMARY OF THE INVENTION

In accordance with a first aspect of the invention, photoacid generators are provided. The photoacid generators comprise a moiety of formula (1):

wherein: $AR^1$ is a substituted or unsubstituted aryl group; $R^1$ is an alkyl or aryl group, each of which may be substituted or unsubstituted, wherein $Ar^1$ and $R^1$ are optionally connected together by a single bond or a divalent linking group to form a ring; Y is a single bond or a divalent group; and * is the point of attachment of the moiety to another atom of the photoacid generator.

Also provided are photoresist compositions. The photoresist compositions comprise a photoacid generator as described herein and a solvent. The photoresist compositions typically comprise an acid-sensitive polymer. In such case, the photoacid generator may be present as part of a polymerized unit of the acid-sensitive polymer or as a component separate from the acid-sensitive polymer.

Also provided are pattern formation methods. The pattern formation methods comprise: (a) forming a photoresist layer from a photoresist composition as described herein on a substrate; (b) exposing the photoresist layer to activating radiation; and (c) developing the exposed photoresist layer to provide a resist relief image.

DETAILED DESCRIPTION OF THE INVENTION

The terminology used herein is for the purpose of describing particular embodiments only and is not intended to be limiting of the invention. The singular forms "a", "an" and "the" are intended to include singular and plural forms, unless the context indicates otherwise. All ranges disclosed herein are inclusive of the endpoints, and the endpoints are independently combinable with each other. When an element is referred to as being "on" or "over" another element, it may be directly in contact with the other element or intervening elements may be present therebetween. In contrast, when an element is referred to as being "directly on" another element, there are no intervening elements present.

The term "aromatic group" refers to a monocyclic or polycyclic ring system that satisfies the Huckel Rule, and may be carbocyclic, including only carbon atoms in the aromatic ring, or heterocyclic, including one or more heteroatoms (e.g., N, O, or S) as ring atom(s); "aryl group" refers to a monovalent aromatic group; and "arylene group" refers to an aromatic group having a valence of two.

The term "alkyl group" refers to a straight, branched, or cyclic saturated hydrocarbon group, or a combination thereof, having a valence of one; "alkylene group" refers to an alkyl group having a valence of two.

The prefix "hetero" means that the compound or group includes one or more heteroatoms (e.g., 1, 2, 3, or 4 or more heteroatoms) each in place of a respective carbon atom, wherein the heteroatoms can independently be, for example, N, O, S, Se, Te, Si, or P.

"Substituted" means that at least one hydrogen atom on the group is replaced with another group, provided that the designated atom's normal valence is not exceeded. Combinations of substituents or variables are permissible. Exemplary groups that may be present on a "substituted" position include, but are not limited to, nitro (—NO$_2$), cyano (—CN), hydroxy (—OH), amino (—NH$_2$), mono- or di-(C$_{1-6}$)alkylamino, alkanoyl (such as a C$_{2-6}$ alkanoyl group such as acyl), formyl (—C(=O)H), carboxylic acid or an alkali metal or ammonium salt thereof, esters (including lactones) such as C$_{2-6}$ alkyl esters (—C(=O)O-alkyl or —OC(=O)-alkyl) and C$_{7-13}$ aryl esters (—C(=O)O-aryl or —OC(=O)-aryl), amido (—C(=O)NR$_2$ wherein R is hydrogen or C$_{1-6}$ alkyl), carboxamido (—CH$_2$C(=O)NR$_2$ wherein R is hydrogen or C$_{1-6}$ alkyl), halogen, thiol (—SH), C$_{1-6}$ alkylthio (—S-alkyl), thiocyano (—SCN), C$_{1-6}$ alkyl, C$_{2-6}$ alkenyl, C$_{2-6}$ alkynyl, C$_{1-6}$ haloalkyl, C$_{1-9}$ alkoxy, C$_{1-6}$ haloalkoxy, C$_{3-12}$ cycloalkyl, C$_{5-18}$ cycloalkenyl, C$_{6-12}$ aryl having at least one aromatic ring (e.g., phenyl, biphenyl, naphthyl, or the like, each ring either substituted or unsubstituted aromatic), C$_{7-19}$ arylalkyl having 1 to 3 separate or fused rings and from 6 to 18 ring carbon atoms, arylalkoxy having 1 to 3 separate or fused rings and from 6 to 18 ring carbon atoms, C$_{7-12}$ alkylaryl, C$_{4-12}$ heterocycloalkyl, C$_{3-12}$ heteroaryl, C$_{1-6}$ alkyl sulfonyl (—S(=O)$_2$-alkyl), C$_{6-12}$ arylsulfonyl (—S(=O)$_2$-aryl), or tosyl (CH$_3$C$_6$H$_4$SO$_2$—), and vinyl and vinyl-containing groups such as acrylic, vinyl ether, vinyl ketone, and norbornyl. When a group is substituted, the indicated number of carbon atoms is the total number of carbon atoms in the group, excluding those of any substituents. For example, the group —CH$_2$CH$_2$CN is a C$_2$ alkyl group substituted with a cyano group.

As used herein, an "acid-labile group" refers to a group in which a bond is cleaved by the catalytic action of an acid, optionally and typically with thermal treatment, resulting in formation of a polar group, such as a carboxylic acid or alcohol group, being formed on the polymer, and optionally and typically with a moiety connected to the cleaved bond becoming disconnected from the polymer. Such acid is typically a photo-generated acid with bond cleavage occurring during post-exposure baking. Suitable acid-labile groups include, for example: tertiary alkyl ester groups, secondary or tertiary aryl ester groups, secondary or tertiary ester groups having a combination of alkyl and aryl groups, tertiary alkoxy groups, acetal groups, or ketal groups. Acid-labile groups are also referred to in the art as "acid-cleavable groups," "acid-cleavable protecting groups," "acid-labile protecting groups," "acid-leaving groups," "acid-decomposable groups," and "acid-sensitive groups."

Photoacid Generators

The photoacid generators (PAGs) of the invention are photo-decomposable with exposure to activating radiation, and generate an acid on photodecomposition. The strength of the photo-generated acid of the PAGs can vary widely, for example, having a pKa from −20 to 20, from −15 to 15, from −12 to 12, from −15 to −1, or from greater than −1 to 6. The PAGs comprise a moiety of formula (1):

wherein: Ar$^1$ is a substituted or unsubstituted aryl group, for example, C$_{6-40}$ carbocyclic aryl or C$_{4-40}$ heterocyclic aryl, each of which is monocyclic or polycyclic and is substituted or unsubstituted, with substituted or unsubstituted C$_6$ carbocyclic aryl being preferred; R$^1$ is a substituted or unsubstituted alkyl or aryl group, for example, C$_{1-20}$ linear alkyl, C$_{3-20}$ branched alkyl, monocyclic or polycyclic C$_{3-20}$ cycloalkyl, monocyclic or polycyclic C$_{6-40}$ carbocyclic aryl, or monocyclic or polycyclic C$_{6-40}$ heterocyclic aryl, each of which is substituted or unsubstituted, with substituted or unsubstituted alkyl being preferred, wherein Ar$^1$ and W are optionally connected together by a single bond or a divalent linking group to form a ring, exemplary divalent linking groups including —O—, —S—, —Te—, —Se—, —C(O)—, —C(S)—, —C(Te)—, —S(O)—, —S(O)$_2$—, —N(R)—, or —C(Se)—, substituted or unsubstituted C$_{1-5}$ alkylene, and combinations thereof, wherein R is hydrogen, C$_{1-20}$ alkyl, C$_{1-20}$ heteroalkyl, C$_{6-30}$ carbocyclic aryl, or C$_{4-30}$ heterocyclic aryl, each of which except for hydrogen can be substituted or unsubstituted; Y is a single bond or a divalent group, for example, —O—, —S—, —Te—, —Se—, —C(O)—, —C(O)O—, —N(R$^a$)—, —C(O)N(R$^{2a}$)—, —N(R$^{2a}$)S(O)$_2$—, substituted or unsubstituted C$_{1-30}$ alkylene, substituted or unsubstituted C$_{3-30}$ cycloalkylene, substituted or unsubstituted C$_{1-30}$ heterocycloalkylene, substituted or unsubstituted C$_{6-30}$ arylene, substituted or unsubstituted C$_{7-30}$ arylalkylene, substituted or unsubstituted $C_{1-30}$ heteroarylene, substituted or unsubstituted $C_{3-30}$ heteroarylalkylene, wherein $R^a$ and $R^{2a}$ are independently hydrogen, $C_{1-20}$ alkyl, $C_{1-20}$ heteroalkyl, $C_{6-30}$ aryl, or $C_{4-30}$ heteroaryl, or combinations thereof, each of which except for hydrogen may be substituted or unsubstituted, and optionally further comprising one or more of —S(O)—, —S(O)$_2$—, —C(S)—, —C(Te)—, or —C(Se)—, with —CH$_2$C(O)O— being preferred for Y; and * is the point of attachment of the moiety to another atom of the photoacid generator. The moiety of formula (1) comprises an acid-labile secondary ester group. With photo-generated acid, the O—C bond of the secondary ester is cleaved, leaving a carboxylic acid group on the decomposed PAG.

The photoacid generator having a moiety of formula (1) is not particularly limited, and can be ionic or non-ionic. Preferably, the PAG is ionic and is represented by formula (2):

$$G^+Z^- \quad (2)$$

wherein $G^+$ is a cation comprising a moiety of formula (1) and $Z^-$ is a counter anion, which may be referred to herein as the cation portion and the anion portion, respectively. The cation and anion are typically organic. The acid strength of the photo-generated acid is determined by the anion portion.

The ionic PAG can be chosen, for example, from onium salts such as sulfonium salts, iodonium salts, halonium salts, quaternary ammonium salts, phosphonium salts, arsonium salts, sulfoxonium salts, tellurenium salts, or selenium salts. Preferably, the PAG is a sulfonium or iodonium salt. The acid generator group may, for example, comprise a negatively charged aromatic-sulfonate or perfluoroalkylsulfonate and a substituted triarylsulfonium or substituted diaryliodonium counter cation. A preferred such ionic PAG is represented by formula (2-1):

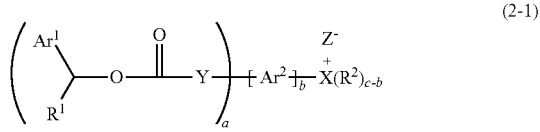

wherein: $Ar^1$, $R^1$, and Y are each independently as defined above with respect to formula (1); $Ar^2$ independently represents a substituted or unsubstituted arylene group, for example, $C_{6-40}$ carbocyclic aryl or $C_{4-40}$ heterocyclic aryl, each of which is monocyclic or polycyclic and is substituted or unsubstituted, and is preferably a substituted or unsubstituted $C_6$ carbocyclic aryl group; X is S or I; $R^2$ independently represents a substituted or unsubstituted alkyl or aryl group, for example, $C_{1-20}$ linear alkyl, $C_{3-20}$ branched alkyl, monocyclic or polycyclic $C_{3-20}$ cycloalkyl, monocyclic or polycyclic $C_{6-40}$ carbocyclic aryl, or monocyclic or polycyclic $C_{4-40}$ heterocyclic aryl, each of which is substituted or unsubstituted, and is preferably a $C_6$ carbocyclic aryl group; $Z^-$ is a counter anion; a is an integer from 1 to the total number of available carbon atoms on $Ar^2$, typically from 1 to 5, and more typically 1 or 2; when X is S, b is 1, 2, or 3 and c is 3; and when X is I, b is 1 or 2 and c is 2; wherein (i) two $R^2$ groups or (ii) an $Ar^2$ group and an $R^2$ group are optionally connected together by a single bond or a divalent linking group to form a ring. Exemplary divalent linking groups include —O—, —S—, —Te—, —Se—, —C(O)—, —C(S)—, —C(Te)—, —S(O)—, —S(O)$_2$—, —N(R)—, or —C(Se)—, substituted or unsubstituted $C_{1-5}$ alkylene, and combinations thereof, wherein R is hydrogen, $C_{1-20}$ alkyl, $C_{1-20}$ heteroalkyl, $C_{6-30}$ carbocyclic aryl, or $C_{4-30}$ heterocyclic aryl, each of which except for hydrogen can be substituted or unsubstituted. When two $R^2$ groups or an $Ar^2$ group and an $R^2$ group are connected together to form a ring, it is preferably with a single bond, —O—, —S—, or —C(O)—.

Suitable exemplary PAG cations of formula (2-1) include the following:

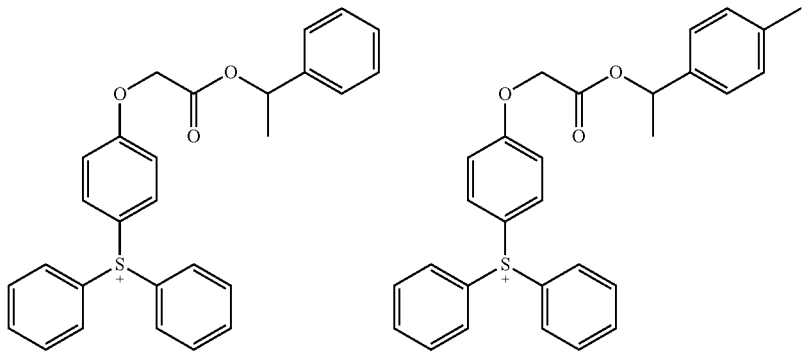

-continued
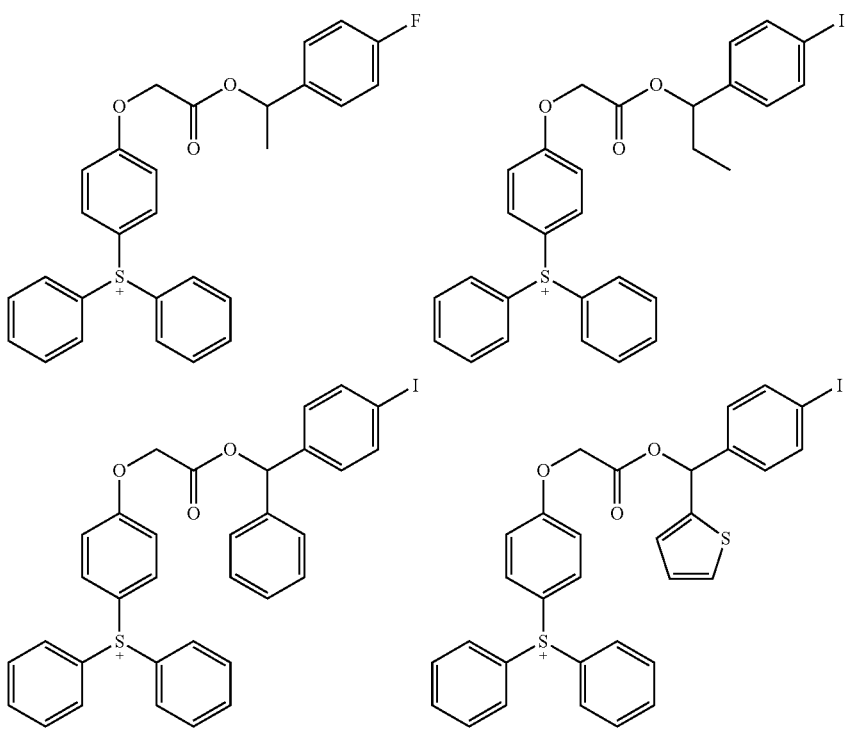
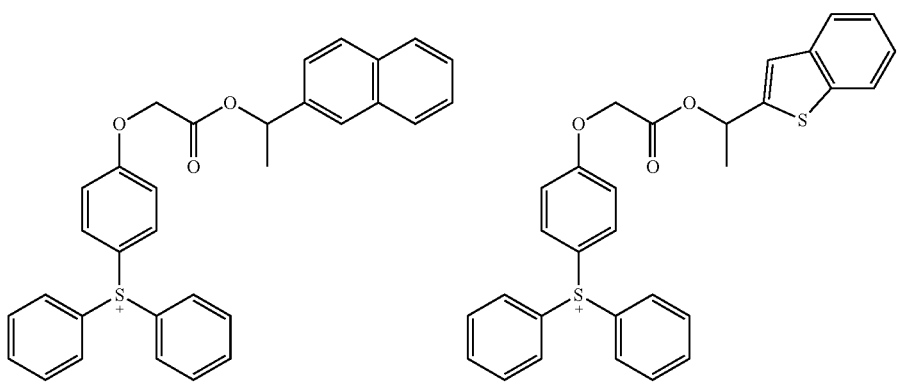
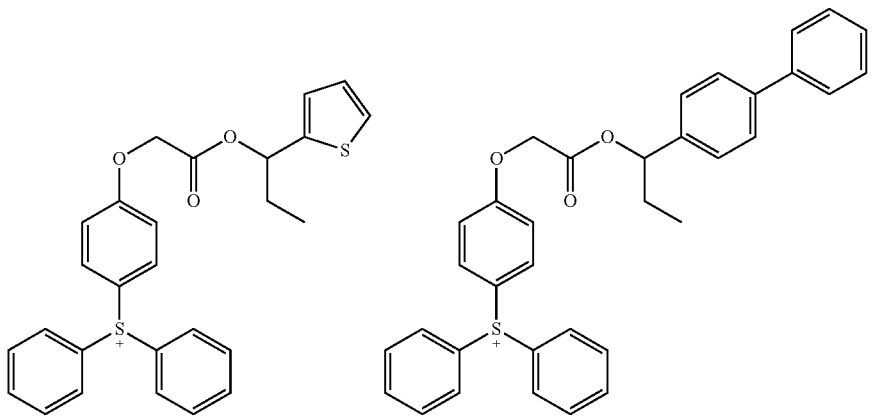

-continued
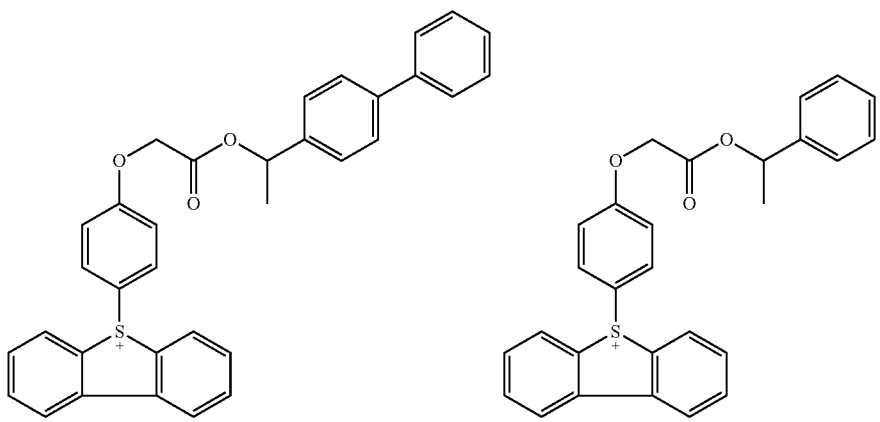
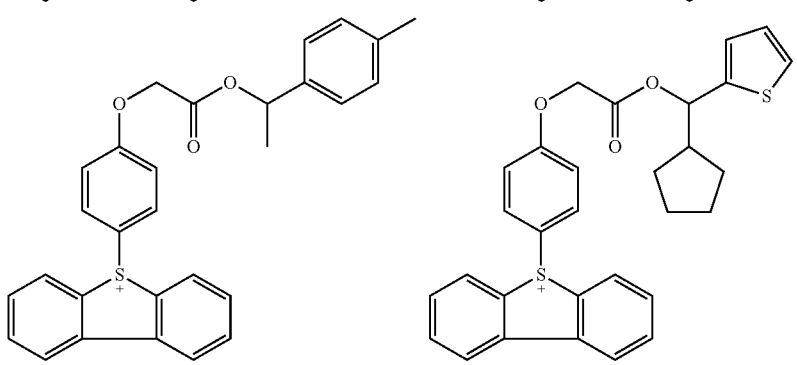
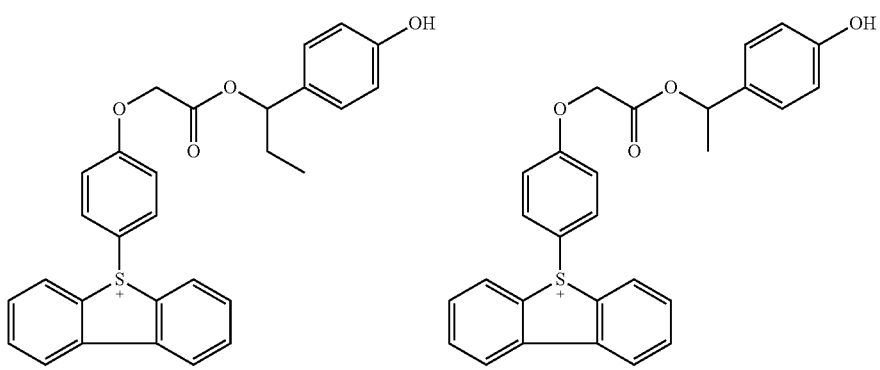
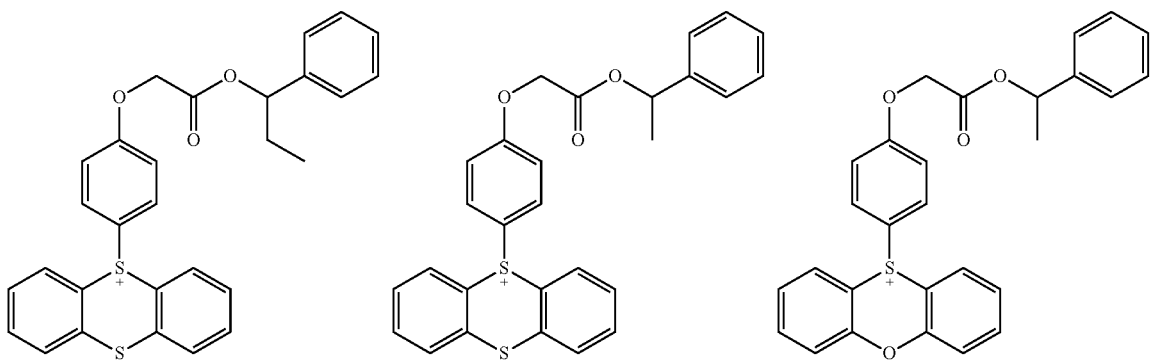

-continued
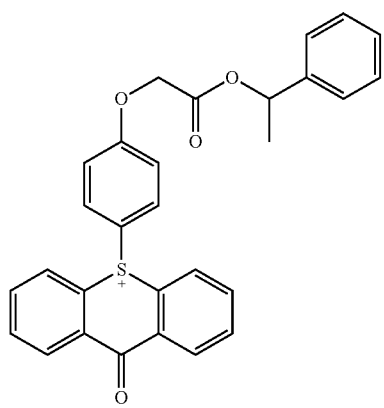
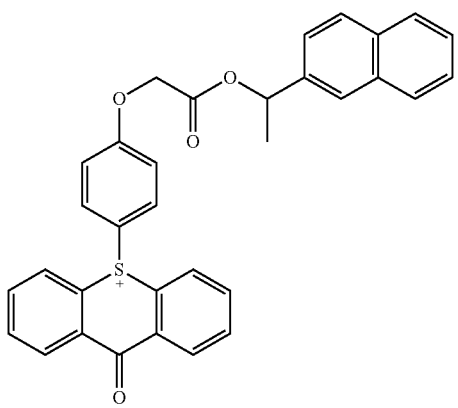
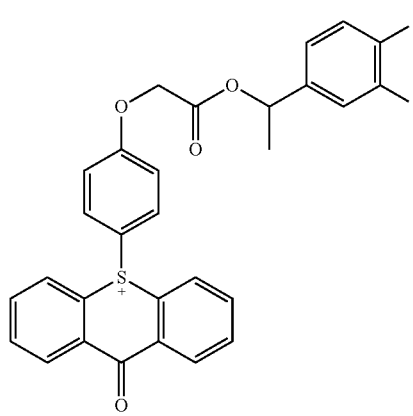
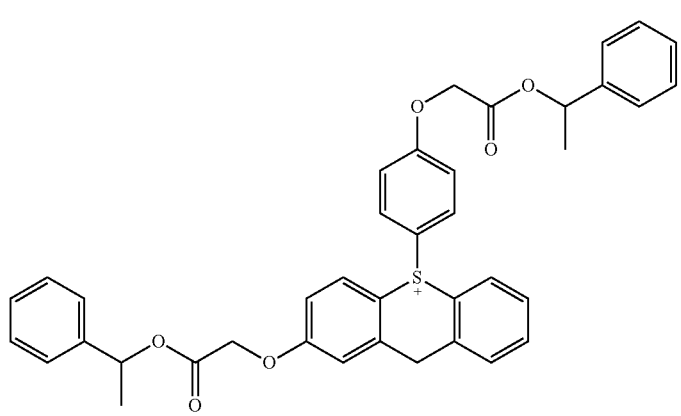
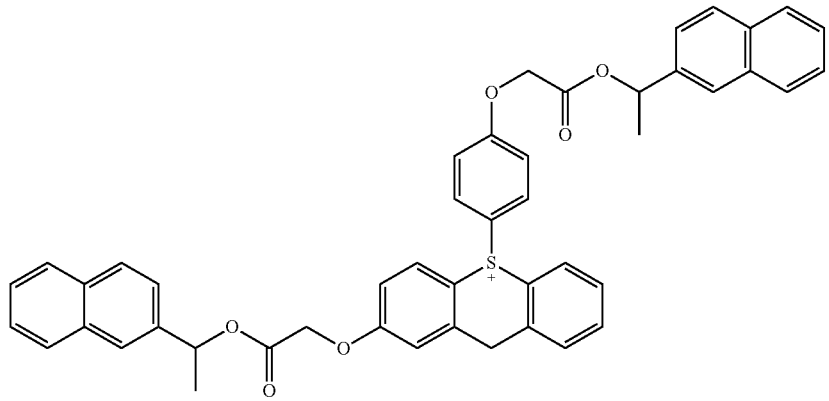
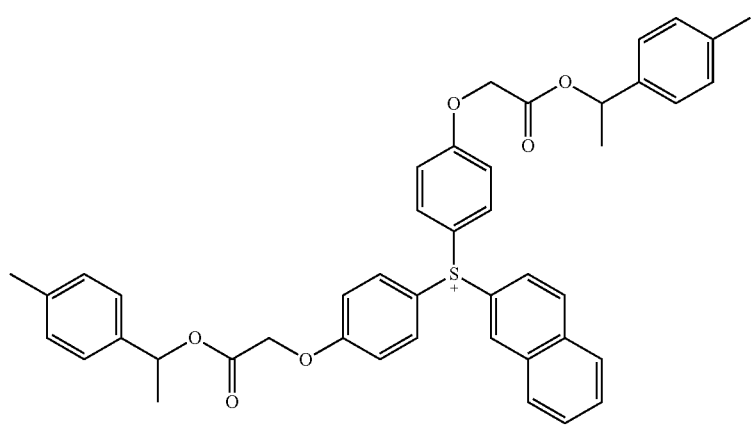

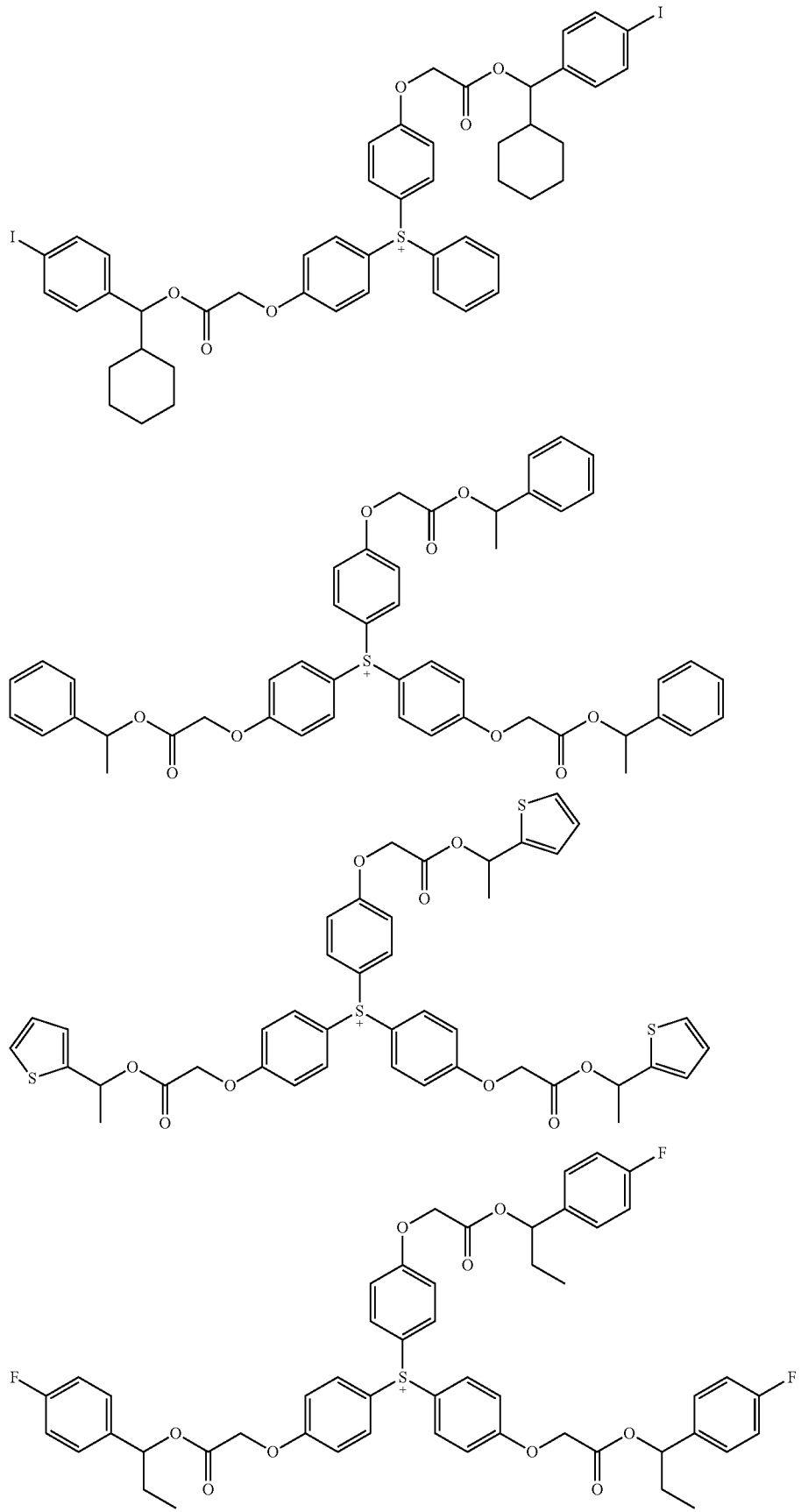

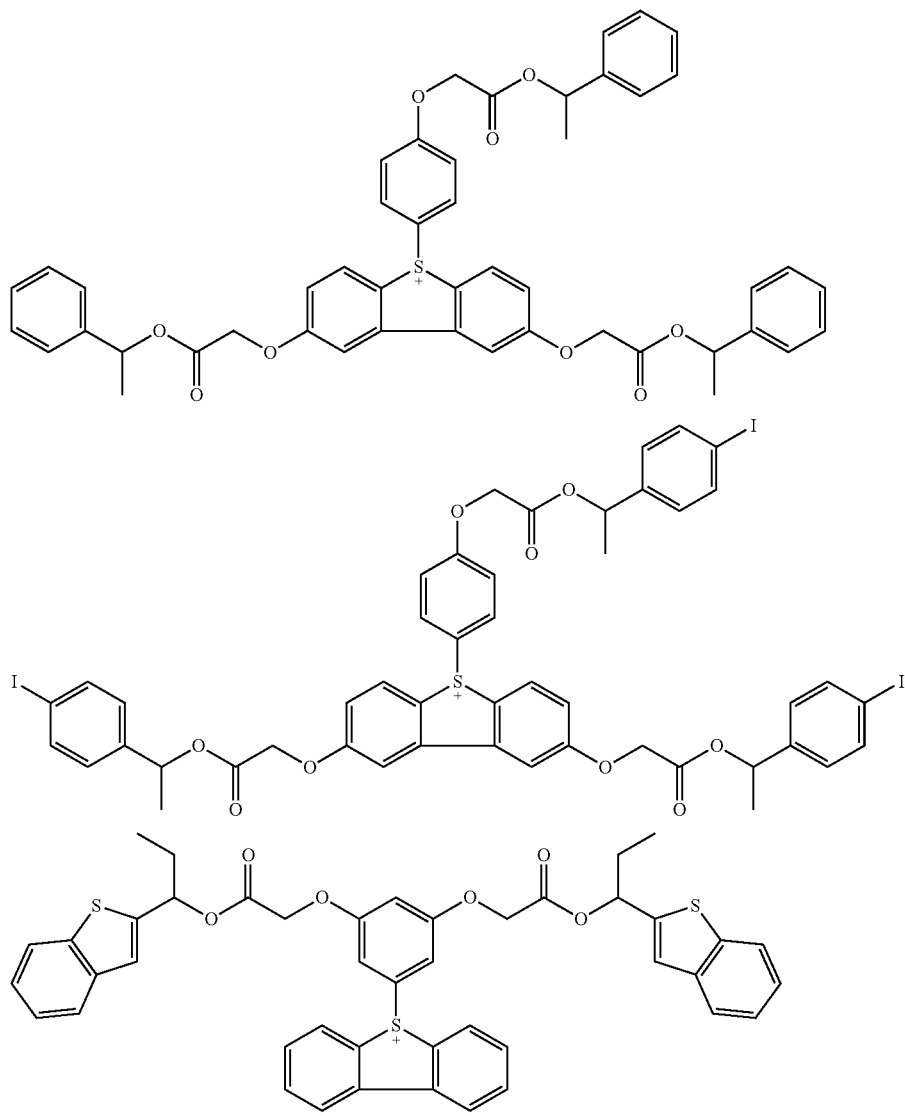
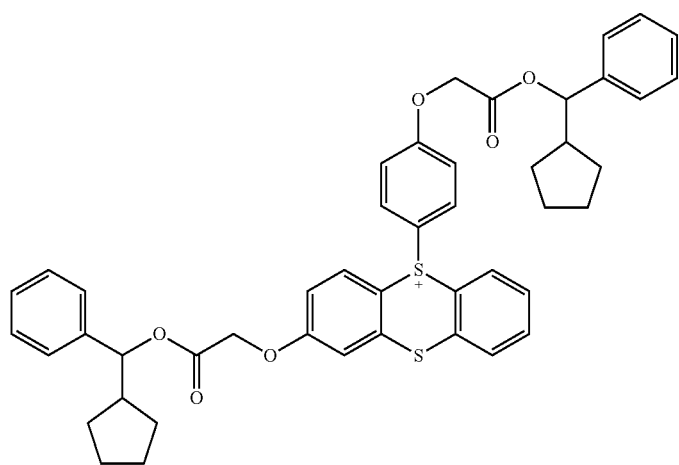

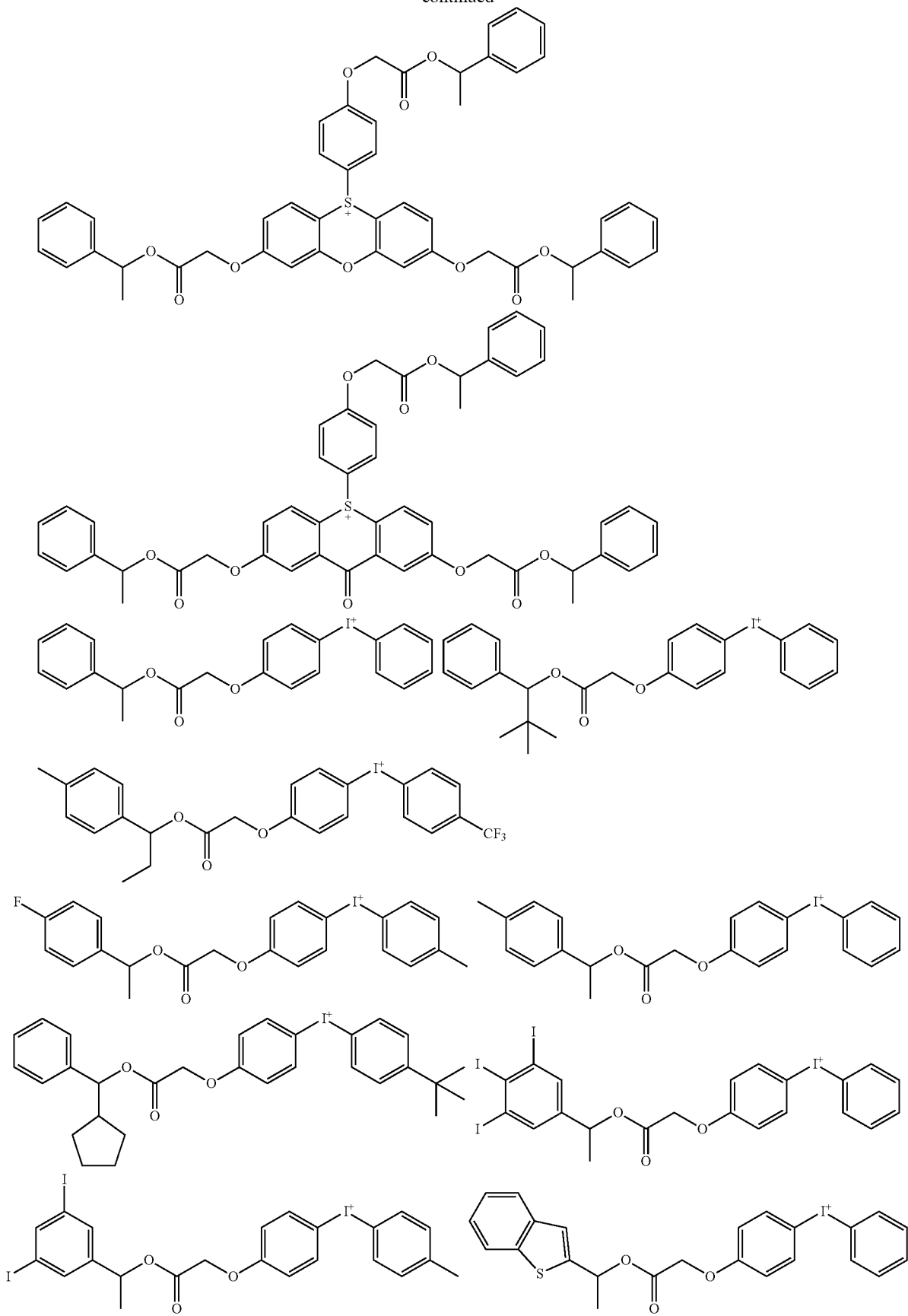

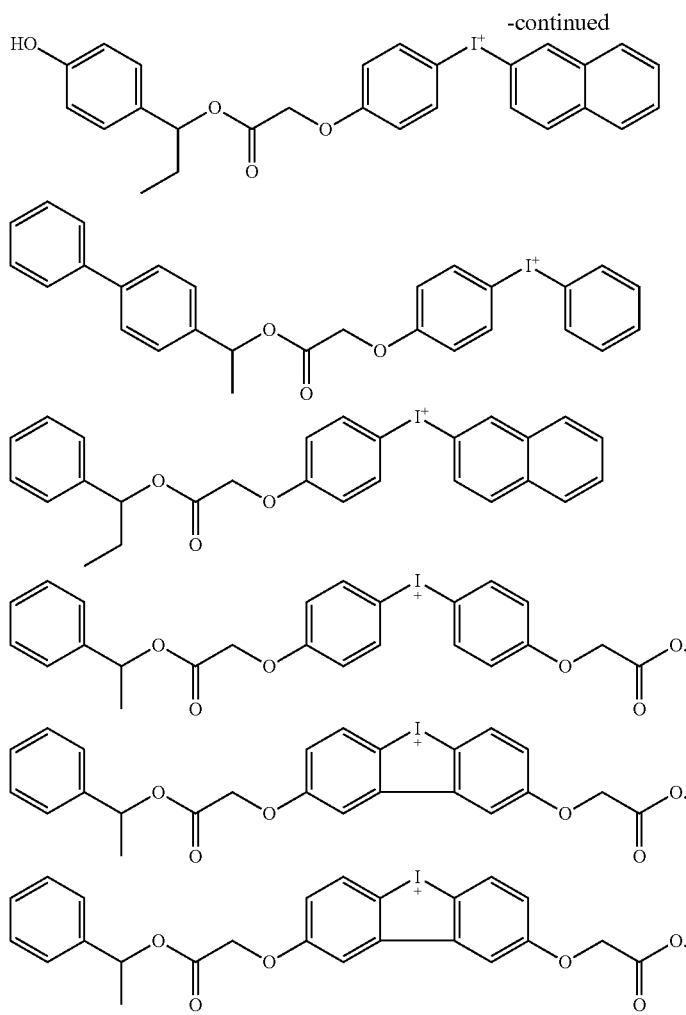

Selection of a suitable PAG anion will depend, for example, on the desired pKa of the photo-generated acid. Preferred PAG anions comprise a group chosen from sulfonate anion, methide anion, sulfonamide anion, sulfonimide anion, sulfamate anion, phenolate anion, or carboxylate anion. Suitable exemplary PAG anions which may be paired with the cations described above include the following:

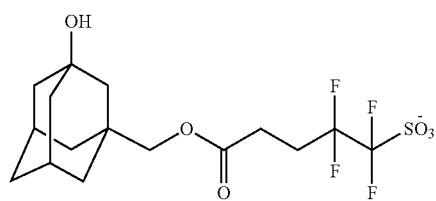

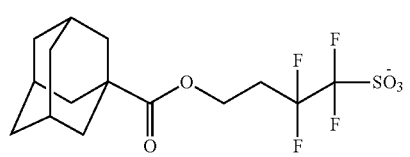

-continued

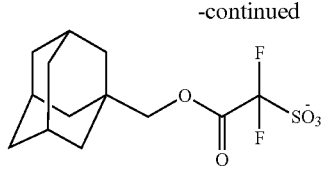

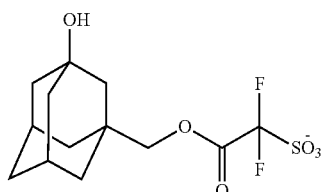

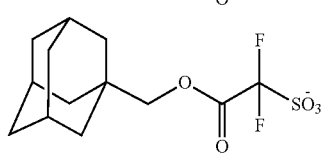

-continued
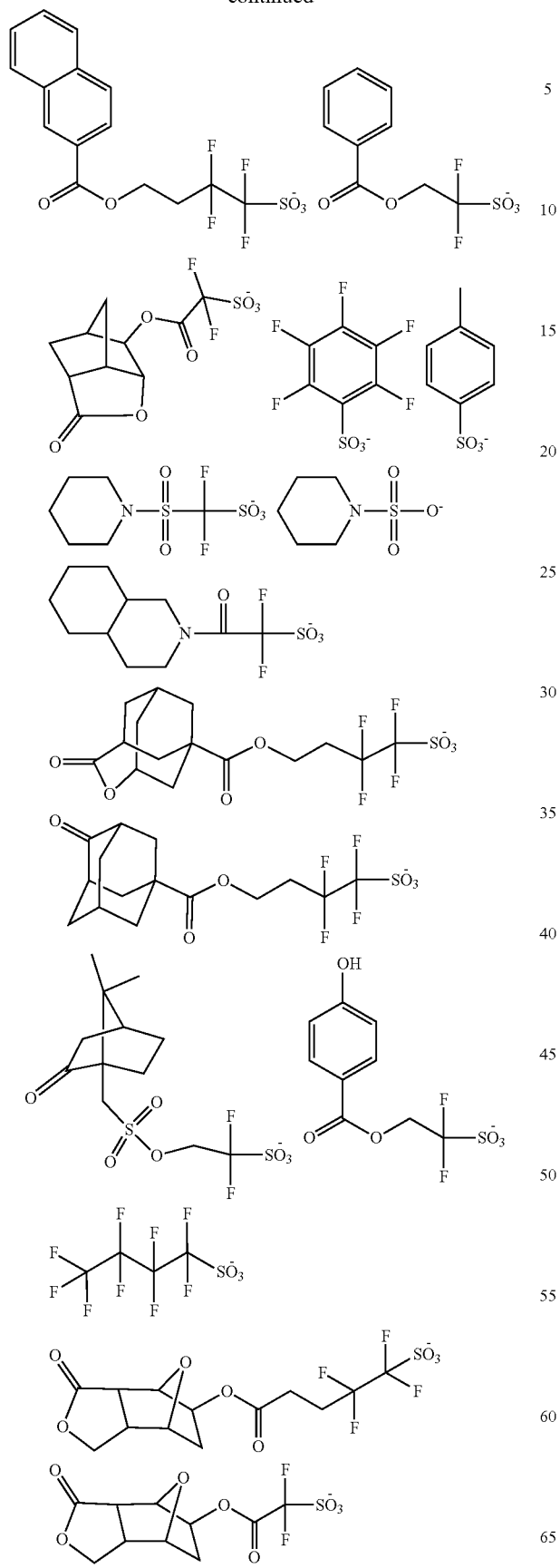
-continued
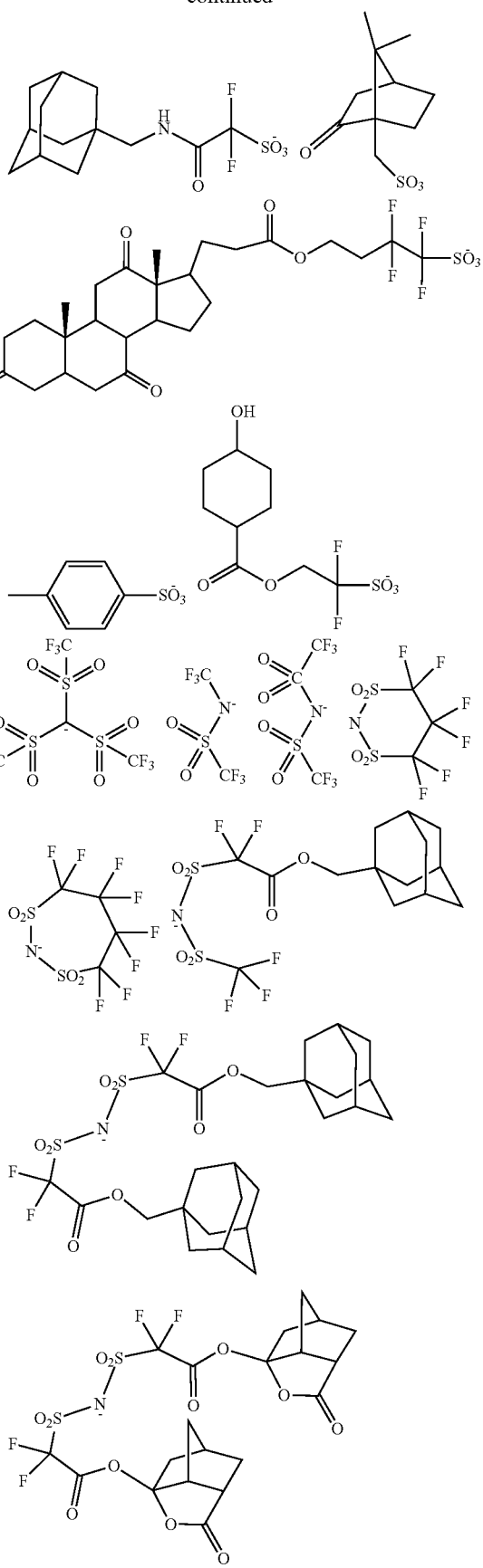

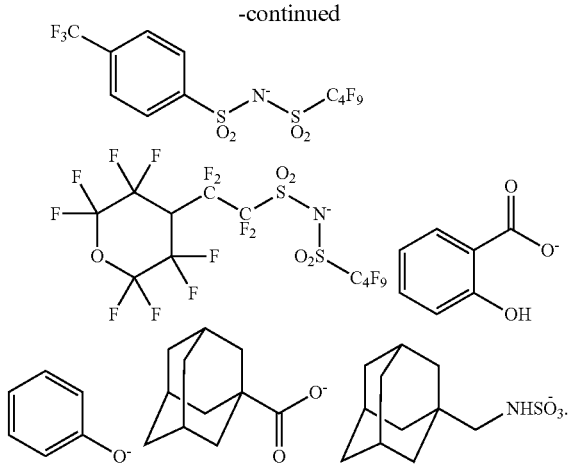

Suitable non-ionic PAGs include, for example, nitrobenzyl derivatives, diazomethane derivatives, sulfonic acid ester derivatives, glyoxime derivatives, β-ketosulfone derivatives, disulfone derivatives, nitrobenzyl sulfonate derivatives, imido-yl sulfonate-derivatives, oxime sulfonate derivatives, imino sulfonate derivatives, and triazine derivatives, that comprise a moiety of formula (1) as described above.

Suitable exemplary non-ionic PAGs include, for example, the following:

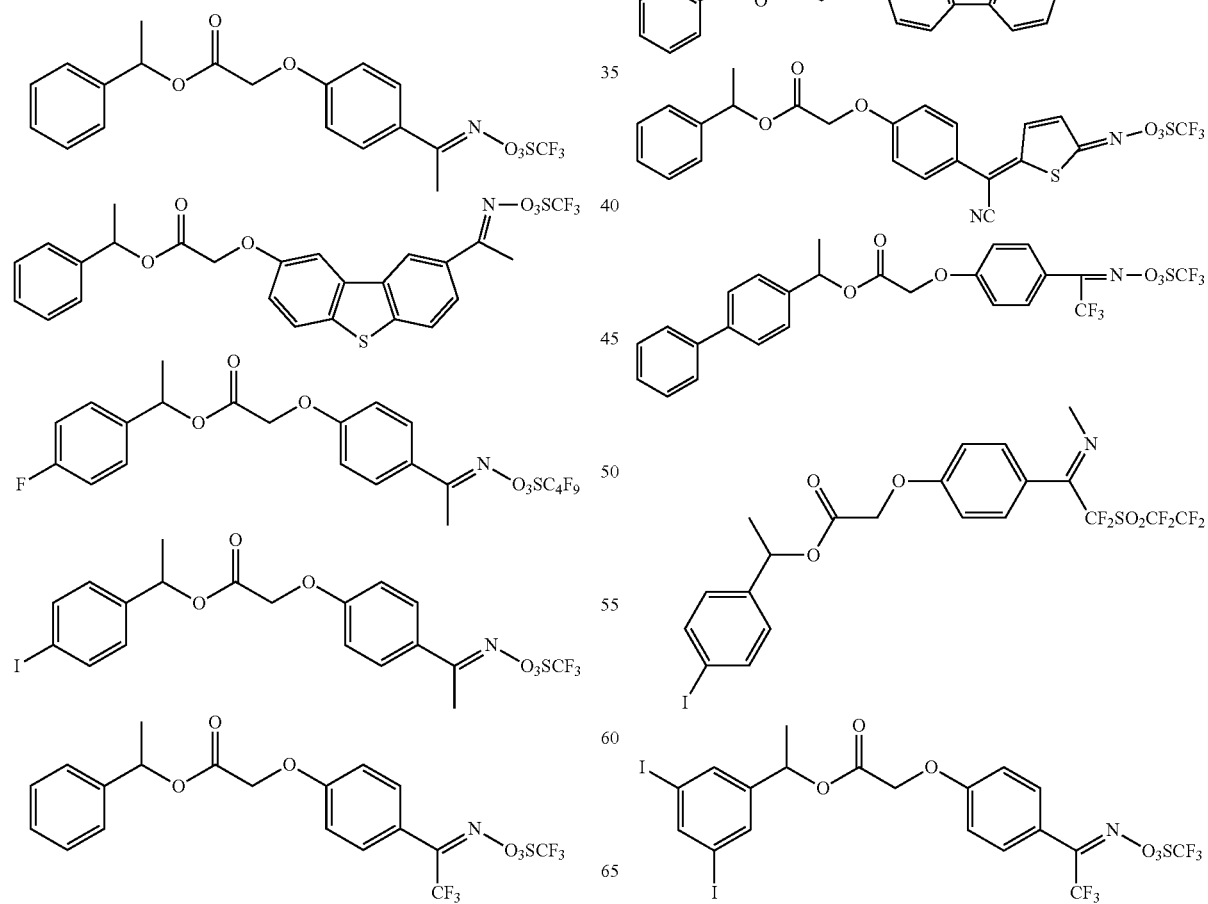
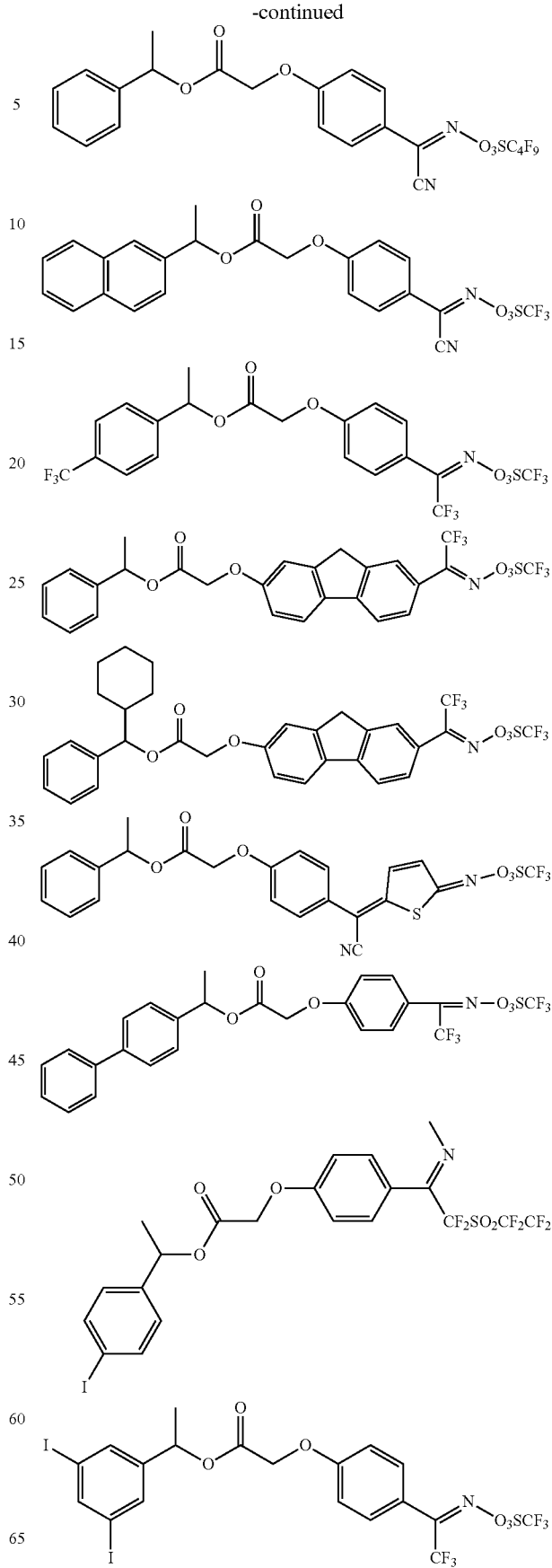

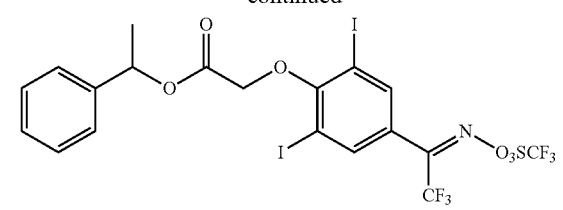
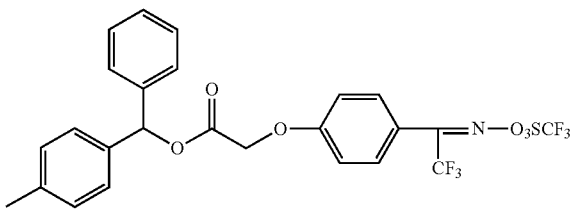
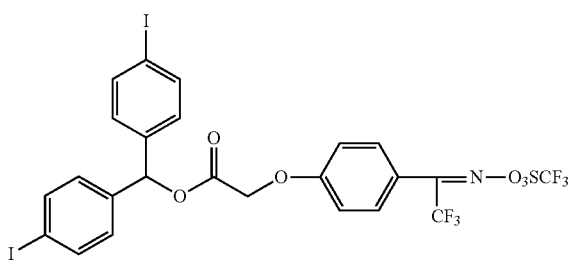
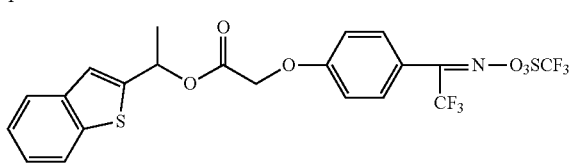
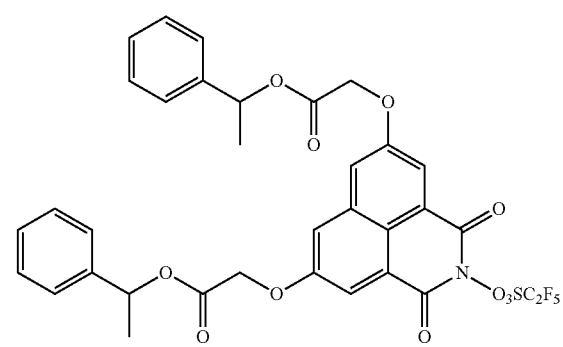
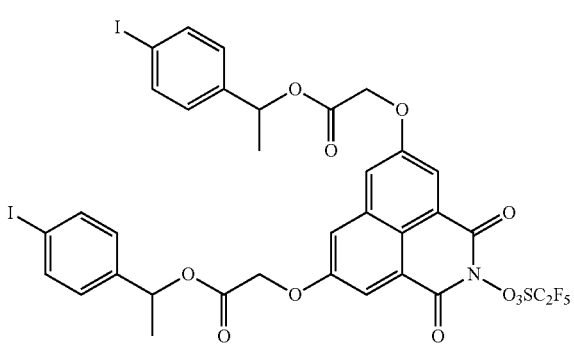
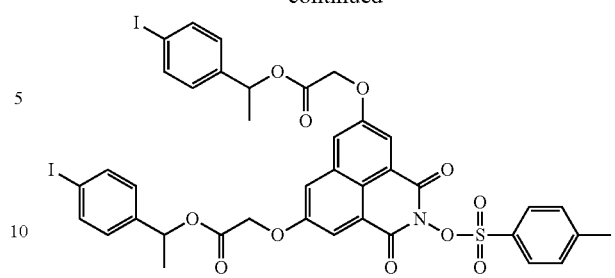
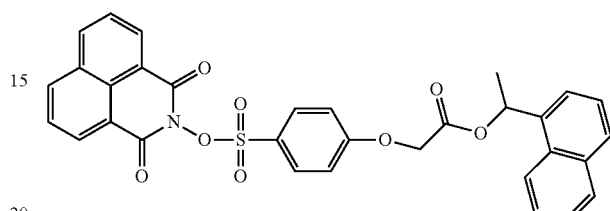
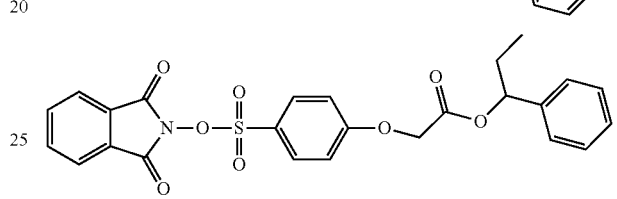
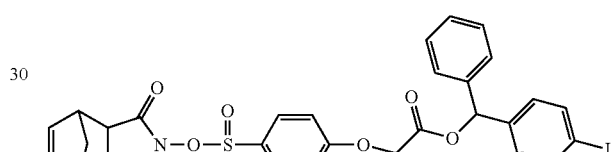
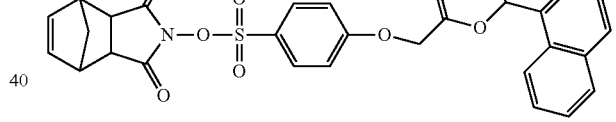
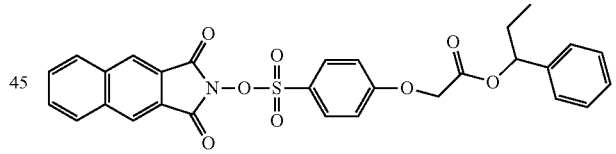
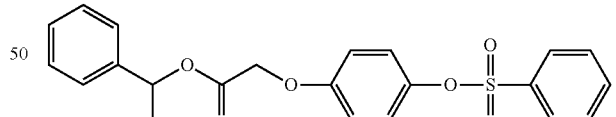
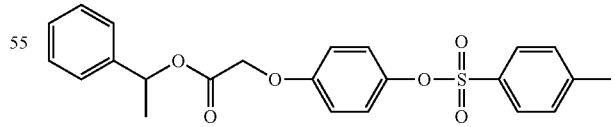
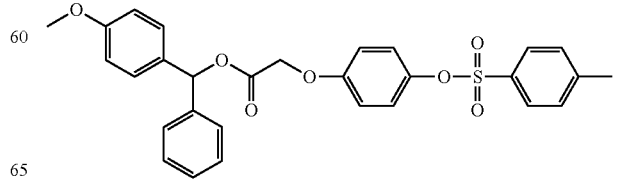

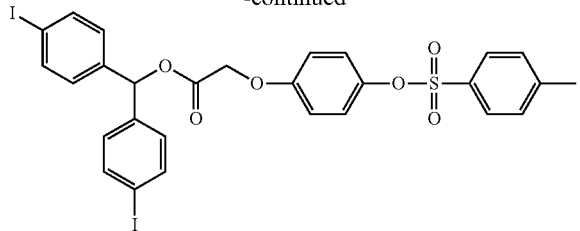
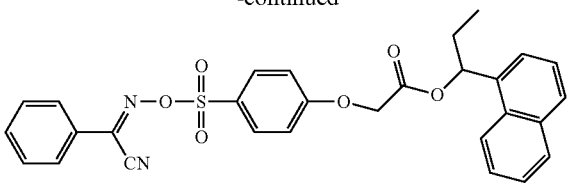
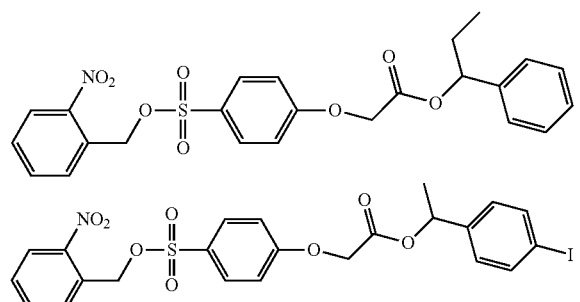
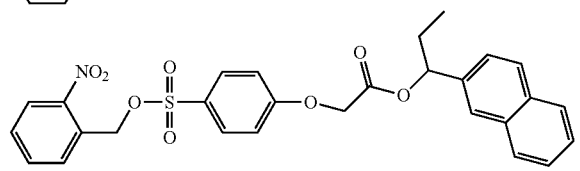
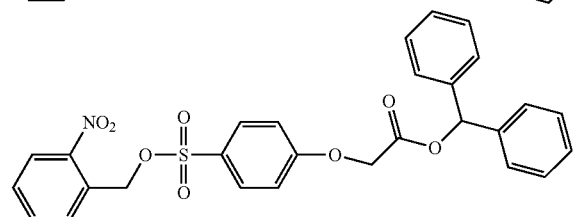
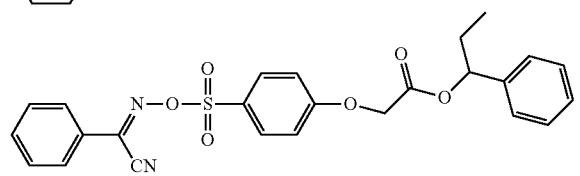

The PAG may take the form of a non-polymeric compound or a polymer. Suitable non-polymeric compounds include monomers and non-polymerizable compounds. Typical monomers include a free-radical polymerizable group such as a vinyl group, with styrenic, acrylic, vinyl ether, vinyl ketone, and norbornyl monomers being typical.

In some aspects, the ionic or nonionic PAG may optionally be covalently bonded as a pendant group to a polymer in polymerized units of the polymer. In the case of an ionic PAG, the anion or the cation may be covalently bonded to the polymer. For example, in formula (2-1), the sulfonium or iodonium salt of formula (1) optionally may be covalently bonded as a pendant group to a polymer through a substituent on $Ar^1$, $R^1$, or $R^2$ of the cation portion, or the anion portion of the sulfonium or iodonium salt of formula (1) may be covalently bonded through $Z^-$ as a pendant group to a polymer. For example, the pendant group may be attached to a main chain or backbone of the polymer.

Polymerized units comprising a PAG can, for example, be derived from the following exemplary monomers:

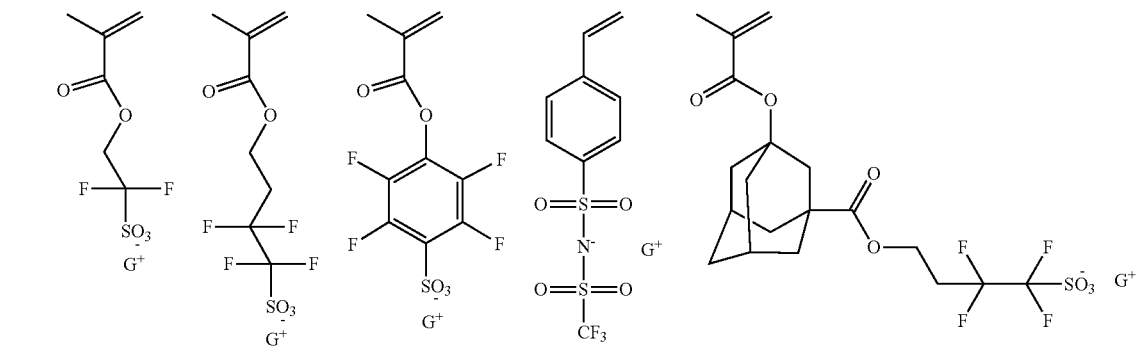

-continued
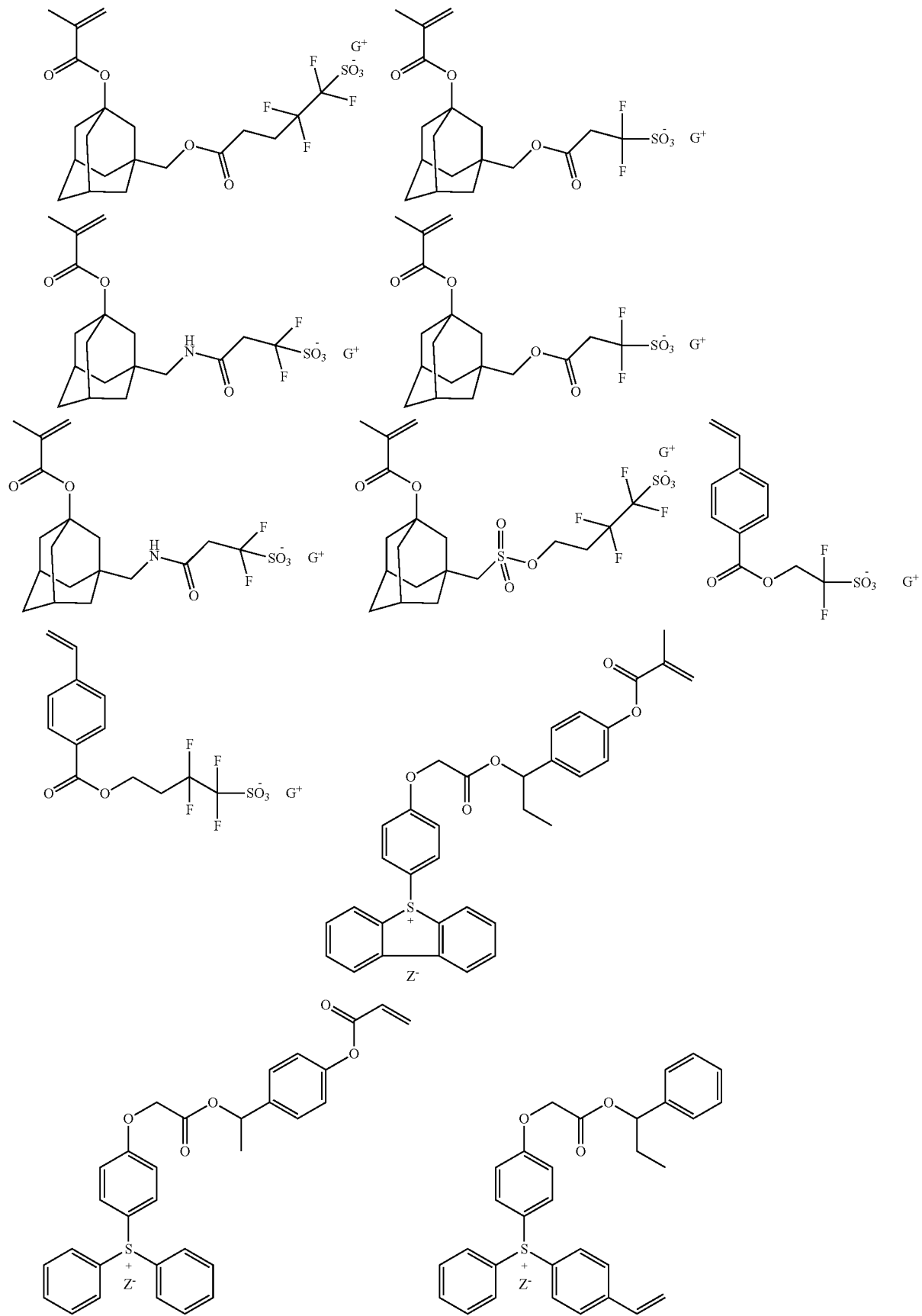

-continued

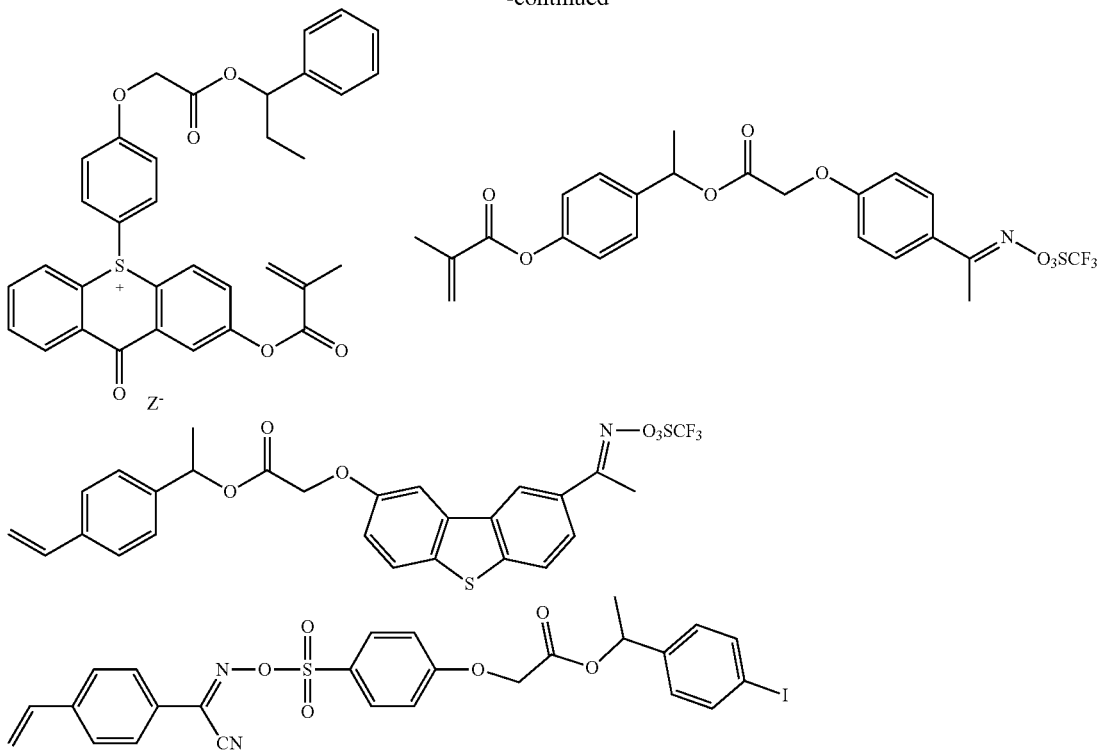

wherein G⁺ and Z⁻ are as defined above.

The polymer may be a homopolymer or, more typically, is a copolymer comprising one or more additional repeating units different from the repeating unit comprising the PAG. Suitable additional repeating units may include, for example, one or more additional units such as described below with respect to the acid-sensitive polymer of the photoresist composition. If used in a copolymer, the repeating unit comprising the PAG are typically present in an amount from 1 to 90 mol %, 1 to 40 mol %, more typically from 1 to 25 mol %, and still more typically from 2 to 15 mol %, based on total repeating units in the polymer.

The polymer typically has a $M_w$ from 1500 to 50,000 Da, from 2000 to 30,000 Da, more specifically 3000 to 20,000 Da, still more specifically 3000 to 10,000 Da. The PDI of the polymer, which is the ratio of $M_w$ to $M_n$ is typically 1.1 to 5, more typically from 1.3 to 2.5. Molecular weights are determined by GPC using polystyrene standards.

The photoacid generators of the invention can be made by persons skilled in the art. For example, the PAGs can be synthesized by covalent attachment of a moiety of formula (1) to an onium salt cation or to a non-ionic PAG. The covalent attachment can be accomplished, for example, by alkylation reaction or esterification reaction of a hydroxy-substituted cation of an onium salt or nonionic PAG with a derivative of the moiety of formula (1). An exemplary alkylation reaction is by reaction of a hydroxy-substituted onium salt or hydroxy-substituted non-ionic photoacid generator with a compound represented by Hal-Y—C(=O)—O—CH(R¹)Ar¹ or the like in the presence of base, wherein Y, R¹ and Ar¹ are as defined above with respect to formula (1). In the case of an onium salt, the product of the alkylation step is typically an onium halide which subsequently can be subject to ion exchange reaction with a salt having the formula Z⁻X⁺, wherein Z⁻ is as define above and X⁺ is an inorganic or organic counter cation, to produce a photoacid generator of formula (2-1).

Photoresist Compositions

The photoacid generators described herein can be used for various applications and find particular use in photoresist compositions useful in the manufacture of electronic devices, for example, semiconductor devices, circuit boards, and display devices. The photoresist compositions comprise a photoacid generator as described above and a solvent, and may include one or more additional optional components. The PAG may serve various functions in the composition depending on the strength of the generated acid and other components of the photoresist composition. For example, in one aspect, the PAG may serve as a source of acid for deprotecting acid-labile group(s) on the PAG and/or on a separate acid-sensitive polymer. In another aspect, the PAG may serve as a photo-decomposable quencher (PDQ) when used in combination with a second PAG, wherein the corresponding photoacid of the second PAG has a lower pKa than a corresponding photoacid of the PDQ.

In view of the acid-sensitive nature of the PAGs of the invention, the PAG may itself in one aspect of the invention serve as a photoresist matrix whether in polymeric or non-polymeric form. Thus, the photoresist composition can optionally be free of an acid-sensitive polymer that is chemically different from the PAG. Alternatively and more typically the photoresist composition may include an acid-sensitive polymer that is chemically different from the PAG. As such, the PAG of the invention may be present in the photoresist composition in a wide range, for example, in an amount from 1 to 100 wt % based on total solids of the photoresist composition. When an acid-sensitive polymer is used that is chemically different than the PAG, the PAG is typically present in an amount from 1 to 65 wt %, more typically from 5 to 55 wt %, and still more typically from 8 to 30 wt %, based on total solids of the photoresist composition. When the PAG serves as the sole or primary acid-sensitive component of the photoresist composition, whether in polymeric or non-polymeric form, the PAG is typically present in an amount from 50 to 100 wt %, more typically from 90 to 100 wt %, and still more typically from 95 to 99.5 wt %, based on total solids of the photoresist composition.

The photoresist composition can include one or more acid-sensitive polymers. The acid-sensitive polymer comprises polymerized units comprising an acid-labile group, for example, a tertiary ester or an acetal group. Additionally or alternatively, the polymerized units comprising an acid-labile group can be derived from a PAG monomer of the invention. Other suitable monomers for these polymerized units include, for example, the following:

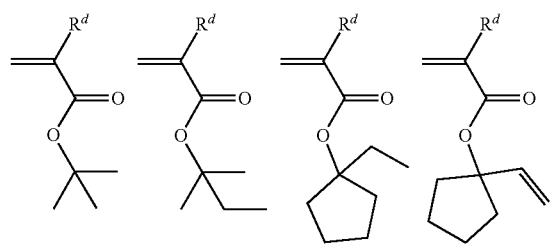
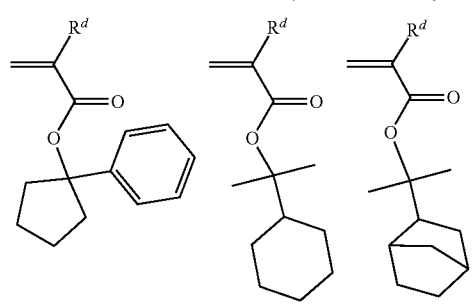
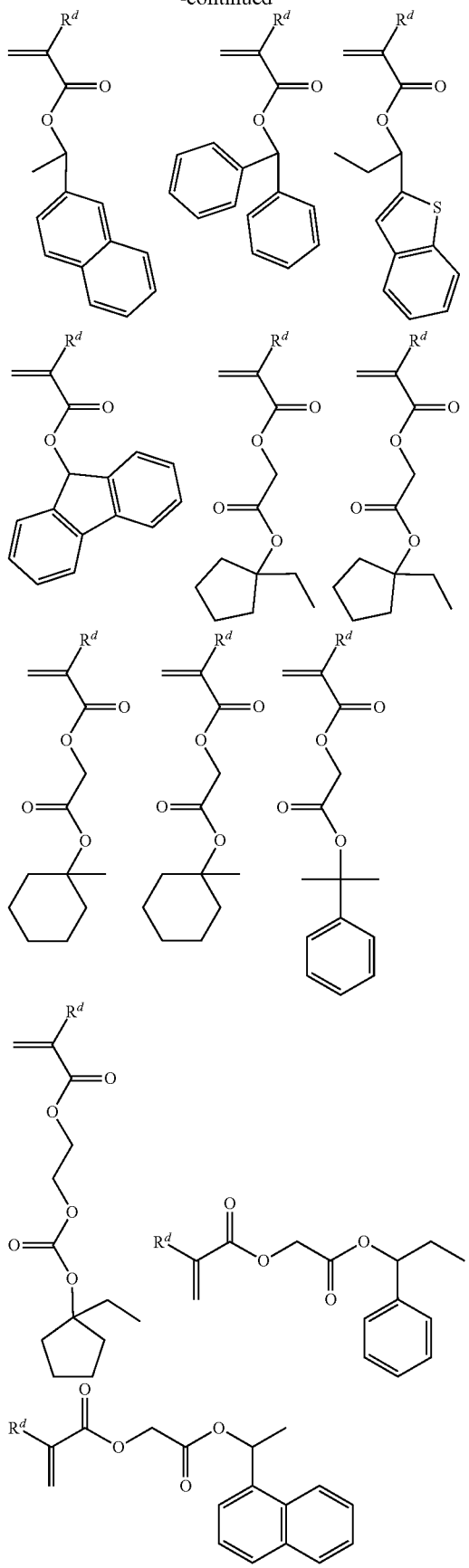

-continued

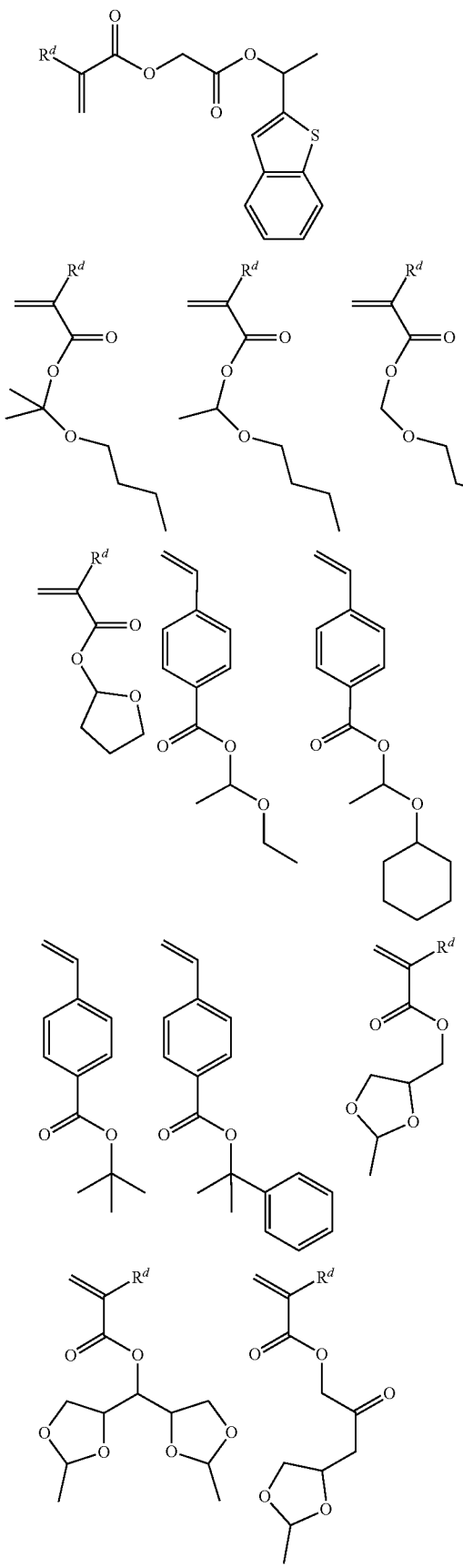
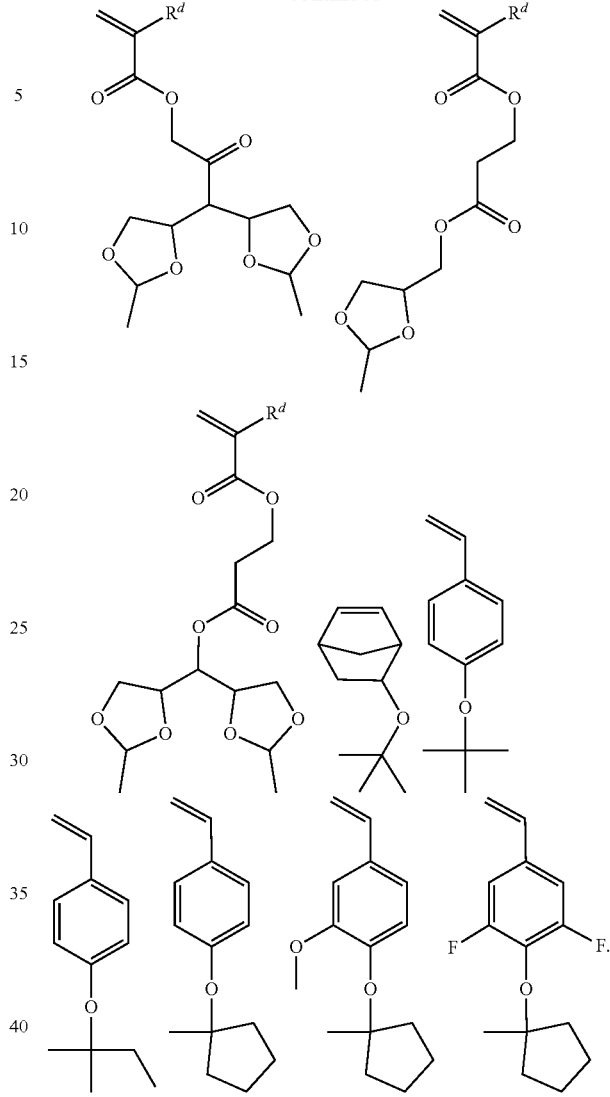

wherein $R^d$ is hydrogen, fluorine, $C_{1-5}$ alkyl, or $C_{1-5}$ fluoroalkyl, typically hydrogen or methyl.

Repeating units having an acid-labile group are typically present in the acid-sensitive polymer in an amount from 10 to 80 mol %, more typically from 25 to 75 mol %, still more typically from 30 to 70 mol %, based on total repeating units in the acid-sensitive polymer.

In some aspects, the acid-sensitive polymer may include a repeating unit having an aromatic group, wherein the aromatic group may be substituted or unsubstituted. The aromatic group is a monocyclic or polycyclic $C_{5-60}$ aromatic group optionally comprising one or more aromatic ring heteroatoms chosen from N, O, S, or a combination thereof. When the aromatic group is polycyclic, the ring or ring groups may be fused (such as naphthyl or the like), directly linked (such as biaryls such as biphenyl), bridged by a heteroatom (such as triphenylamino or diphenylene ether), and/or may include a combination of fused and directly linked rings (such as binaphthyl or the like).

The monocyclic or polycyclic $C_{5-60}$ aromatic group can be substituted or unsubstituted. Exemplary substituents include, but are not limited to, substituted or unsubstituted $C_{1-30}$ alkyl, substituted or unsubstituted $C_{1-30}$ haloalkyl, substituted or unsubstituted $C_{3-30}$ cycloalkyl, substituted or unsubstituted $C_{1-30}$ heterocycloalkyl, substituted or unsubstituted $C_{2-30}$ alkenyl, substituted or unsubstituted $C_{2-30}$ alkynyl, substituted or unsubstituted $C_{6-30}$ aryl, substituted or unsubstituted $C_{7-30}$ arylalkyl, substituted or unsubstituted $C_{7-30}$ alkylaryl, substituted or unsubstituted $C_{3-30}$ heteroaryl, substituted or unsubstituted $C_{4-30}$ heteroarylalkyl, halogen, —$OR^{51}$, —$SR^{52}$, or —$NR^{53}R^{54}$, wherein $R^{51}$ to $R^{54}$ are each independently hydrogen, or substituted or unsubstituted $C_{1-30}$ alkyl, substituted or unsubstituted $C_{3-30}$ cycloalkyl, substituted or unsubstituted $C_{2-30}$ heterocycloalkyl, substituted or unsubstituted $C_{6-30}$ aryl, substituted or unsubstituted $C_{7-30}$ arylalkyl, substituted or unsubstituted $C_{3-30}$ heteroaryl, or substituted or unsubstituted $C_{4-30}$ heteroarylalkyl. Preferably, the aromatic group is a substituted $C_{6-30}$ aryl group or a substituted $C_{7-30}$ heteroaryl group, wherein the aromatic group is substituted with a heteroatom-containing substituent group, such as —$OR^{51}$, —$SR^{52}$, or —$NR^{53}R^{54}$, wherein $R^{51}$ to $R^{54}$ are each independently hydrogen, or substituted or unsubstituted $C_{1-10}$ alkyl, substituted or unsubstituted $C_{3-20}$ cycloalkyl, substituted or unsubstituted $C_{2-20}$ heterocycloalkyl, substituted or unsubstituted $C_{6-30}$ aryl, substituted or unsubstituted $C_{7-30}$ arylalkyl, substituted or unsubstituted $C_{3-30}$ heteroaryl, or substituted or unsubstituted $C_{4-30}$ heteroarylalkyl.

The repeating unit having the aromatic group is typically present in the acid-sensitive polymer in an amount from 5 to 80 mol %, more typically from 10 to 50 mol %, still more typically from 10 to 40 mol %, based on total repeating units in the acid-sensitive polymer.

The acid-sensitive polymer may include a repeating unit comprising a lactone group. Suitable repeating units may, for example, be derived from a monomer of formula (5a) or formula (5b):

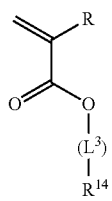

(5a)

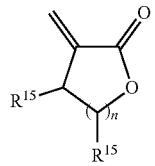

(5b)

In formula (5a), R is hydrogen, fluorine, cyano, a substituted or unsubstituted $C_{1-10}$ alkyl, or a substituted or unsubstituted $C_{1-10}$ fluoroalkyl. Preferably, $R^d$ is hydrogen, fluorine, or substituted or unsubstituted $C_{1-5}$ alkyl, typically methyl. $L^3$ may be a single bond or a divalent linking group comprising one or more of substituted or unsubstituted $C_{1-30}$ alkylene, substituted or unsubstituted $C_{1-30}$ heteroalkylene, substituted or unsubstituted $C_{3-30}$ cycloalkylene, substituted or unsubstituted $C_{1-30}$ heterocycloalkylene, substituted or unsubstituted $C_{6-30}$ arylene, substituted or unsubstituted $C_{7-30}$ arylalkylene, or substituted or unsubstituted $C_{1-30}$ heteroarylene, or substituted or unsubstituted $C_{3-30}$ heteroarylalkylene, wherein $L^3$ optionally may further include one or more groups chosen, for example, from —O—, —C(O)—, —C(O)—O—, —S—, —S(O)$_2$—, and —N($R^{44}$)—S(O)$_2$—, wherein $R^{44}$ may be hydrogen, a straight chain or branched $C_{1-20}$ alkyl, monocyclic or polycyclic $C_{3-20}$ cycloalkyl, or monocyclic or polycyclic $C_{3-20}$ heterocycloalkyl. $R^{14}$ may be a monocyclic, polycyclic, or fused polycyclic $C_{4-20}$ lactone-containing group. In formula (5b), $R^{15}$ is hydrogen or a non-hydrogen substituent, typically substituted or unsubstituted $C_{1-10}$ alkyl and n is 1 or 2.

Suitable exemplary lactone-containing monomers of formulas (5a) and (5b) include the following:

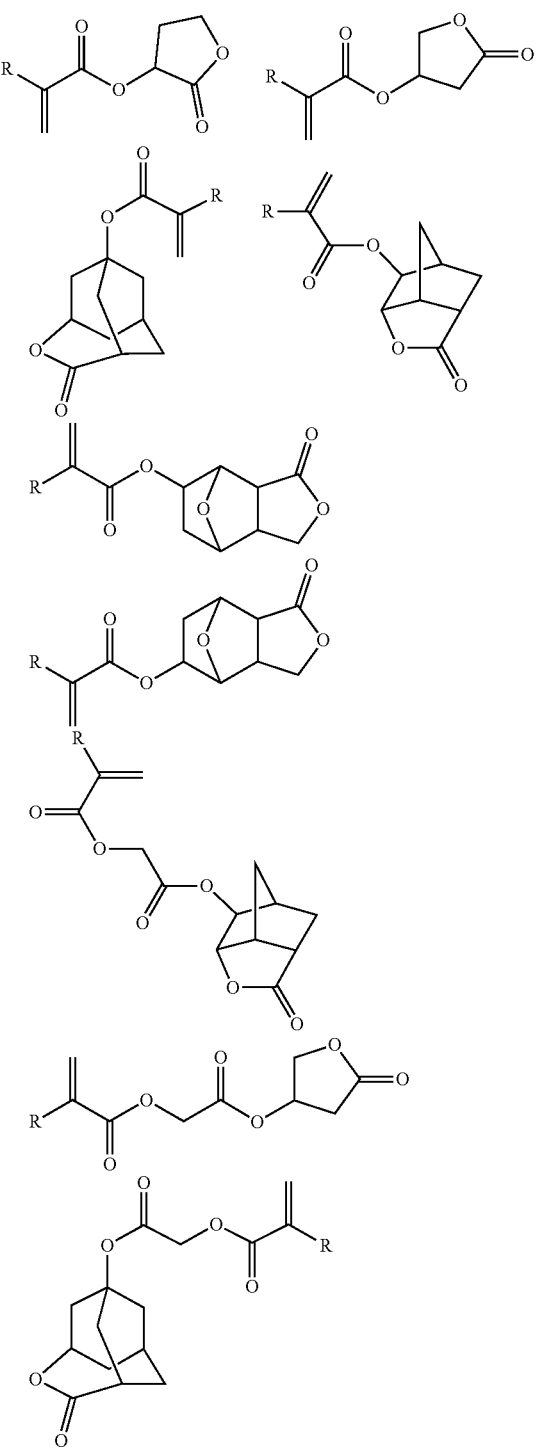

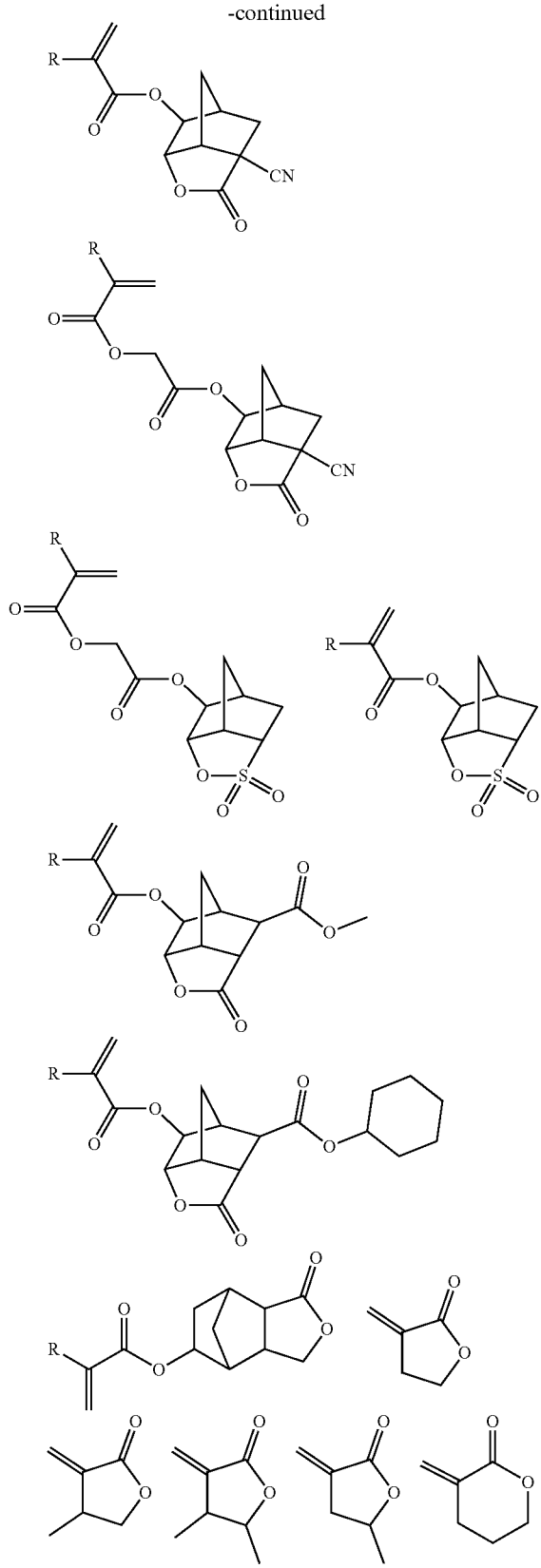

wherein R is as described above. When present, the acid-sensitive polymer typically comprises a lactone repeating unit in an amount from 5 to 60 mol %, typically 20 to 55 mol %, more typically 25 to 50 mol % based on total repeating units in the acid-sensitive polymer.

The acid-sensitive polymer may include a base-soluble repeating unit having a pKa of less than or equal to 12. For example, the base-soluble repeating unit can be derived from a monomer of formula (6):

In formula (6), $R^g$ may be hydrogen, fluorine, cyano, a substituted or unsubstituted $C_{1-10}$alkyl, or a substituted or unsubstituted $C_{1-10}$ fluoroalkyl. Preferably, $R^g$ is hydrogen, fluorine, or substituted or unsubstituted $C_{1-5}$ alkyl, typically methyl. $Q^4$ may comprise one or more of substituted or unsubstituted $C_{1-30}$ alkylene, substituted or unsubstituted $C_{3-30}$ cycloalkylene, substituted or unsubstituted $C_{1-30}$ heterocycloalkylene, substituted or unsubstituted $C_{6-30}$ arylene, substituted or unsubstituted divalent $C_{7-30}$ arylalkyl, substituted or unsubstituted $C_{1-30}$ heteroarylene, or substituted or unsubstituted divalent $C_{3-30}$ heteroarylalkyl, or —C(O)—O—. W is a base-soluble group and can be chosen, for example, from hydroxyl (—OH); —C(O)—OH; a fluorinated alcohol such as —C(CF$_3$)$_2$OH; an imide; or —NH—S(O)$_2$—Y$^1$ where Y$^1$ is $C_{1-4}$ alkyl or fluoroalkyl, typically $C_{1-4}$ perfluoroalkyl. In formula (6), a is an integer of 1 to 3.

Non-limiting examples of monomers of formula (6) include:

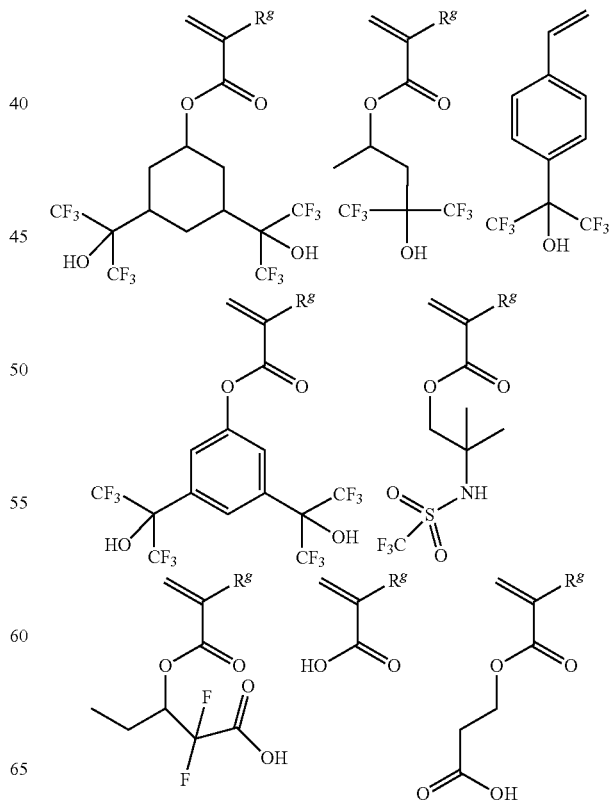

-continued

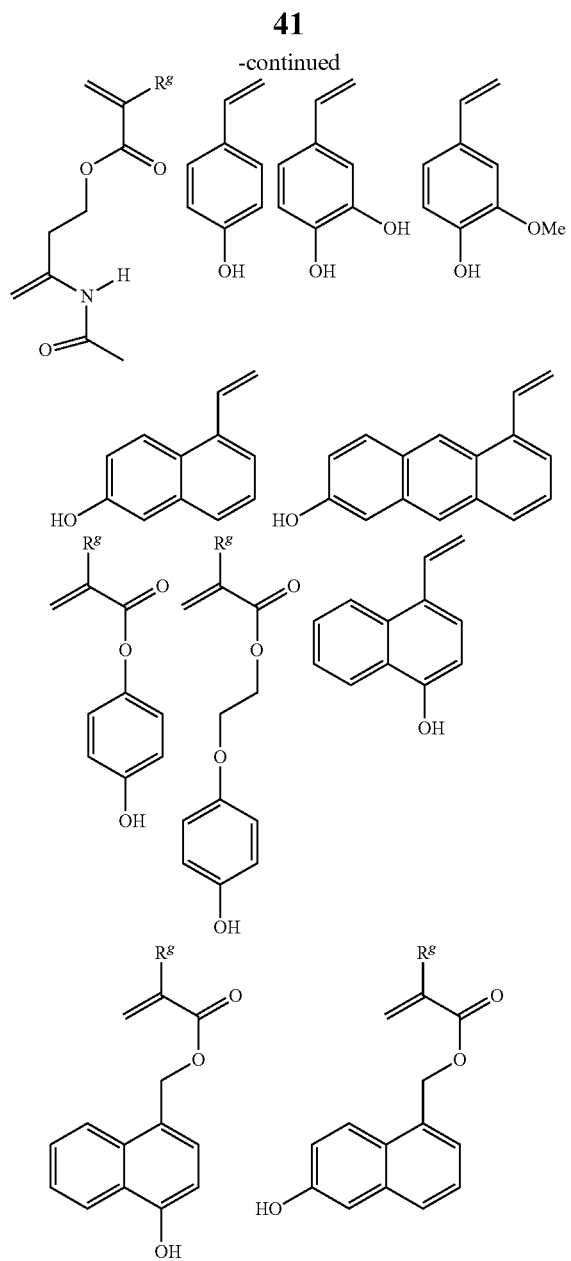

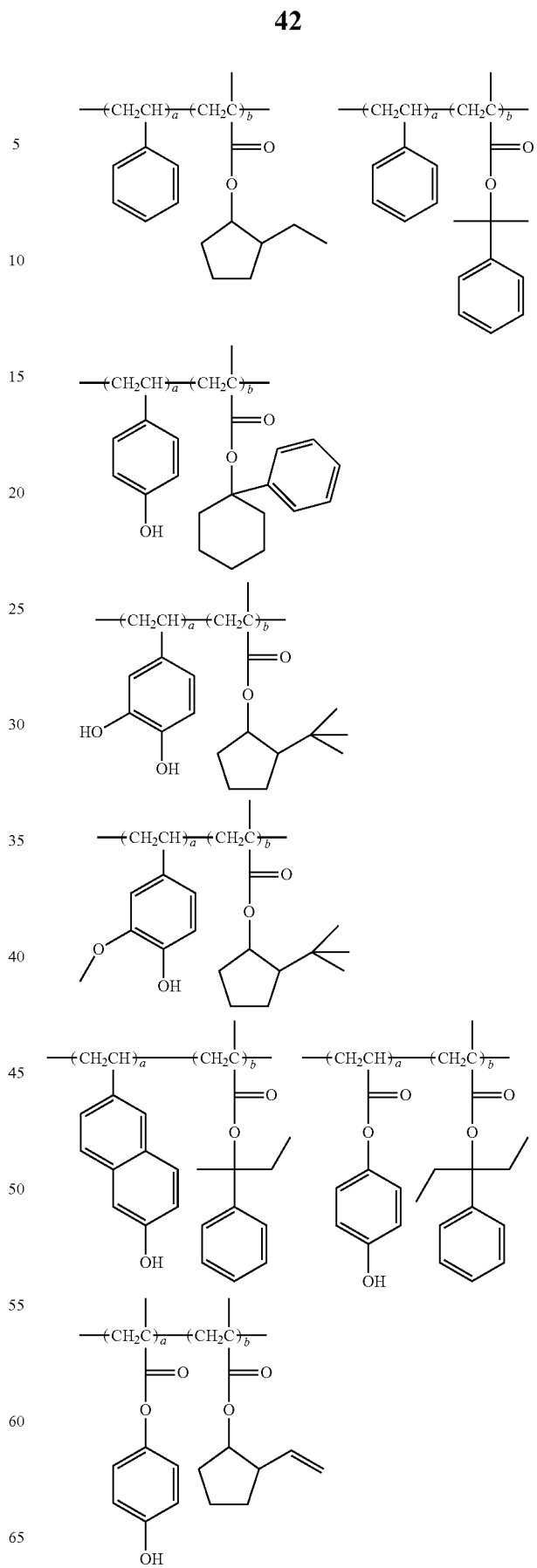

wherein $R^g$ is as described above. When present, the acid-sensitive polymer typically comprises the above-described base-soluble repeating unit in an amount from 5 to 60 mol %, typically 20 to 55 mol %, more typically 25 to 50 mol % based on total repeating units in the acid-sensitive polymer.

The acid-sensitive polymer may optionally include one or more additional repeating units. The additional repeating units may include, for example, one or more additional units for purposes of adjusting properties of the photoresist composition, such as etch rate and solubility. The additional units may include, for example, one or more of styrene, (meth) acrylate, vinyl ether, vinyl ketone, or vinyl ester type units. The one or more additional repeating units if present in the acid-sensitive polymer may be used in an amount of up to 70 mol %, typically from 3 to 50 mol %, based on total repeating units of the acid-sensitive polymer.

Non-limiting examples of the acid-sensitive polymer include the following:

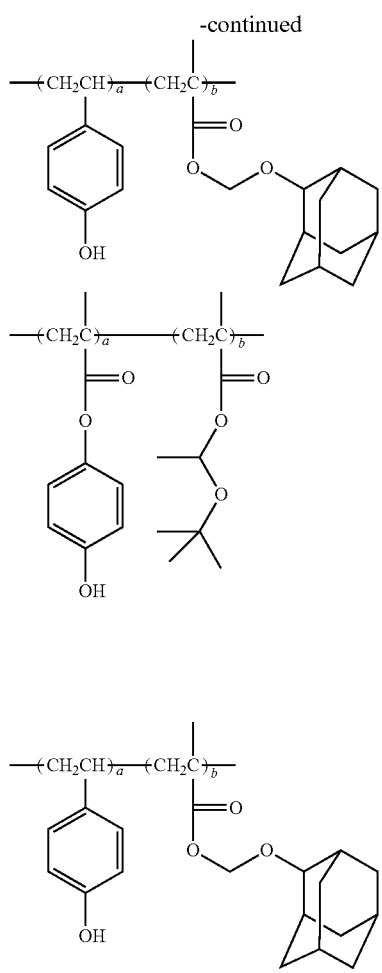
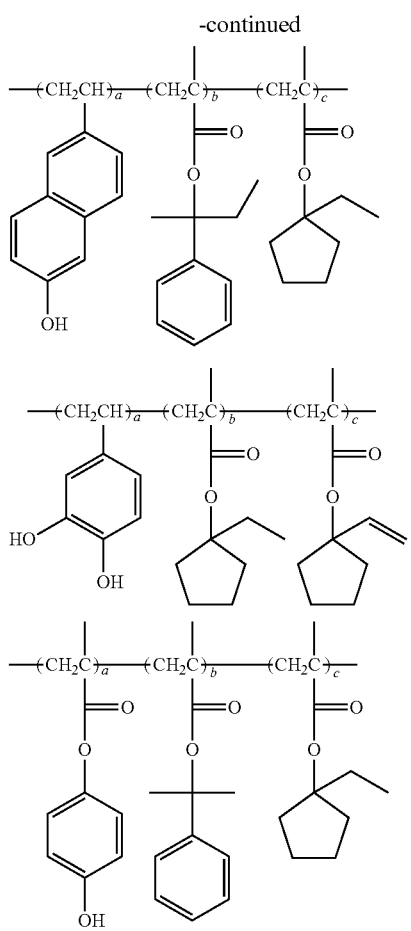
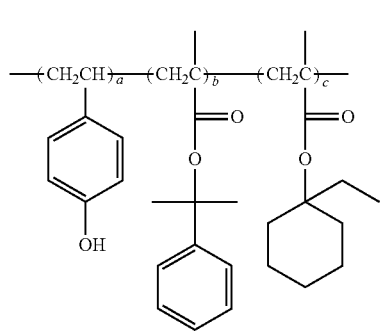
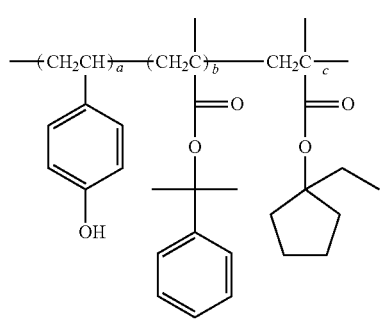
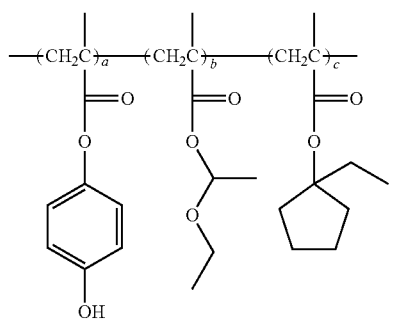
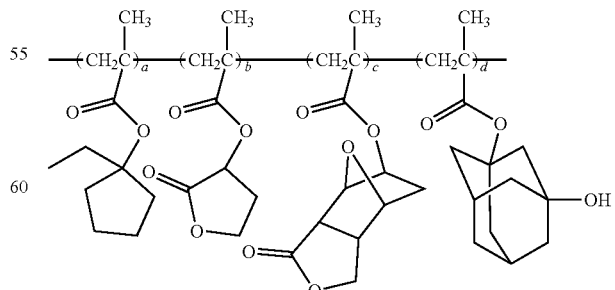

-continued
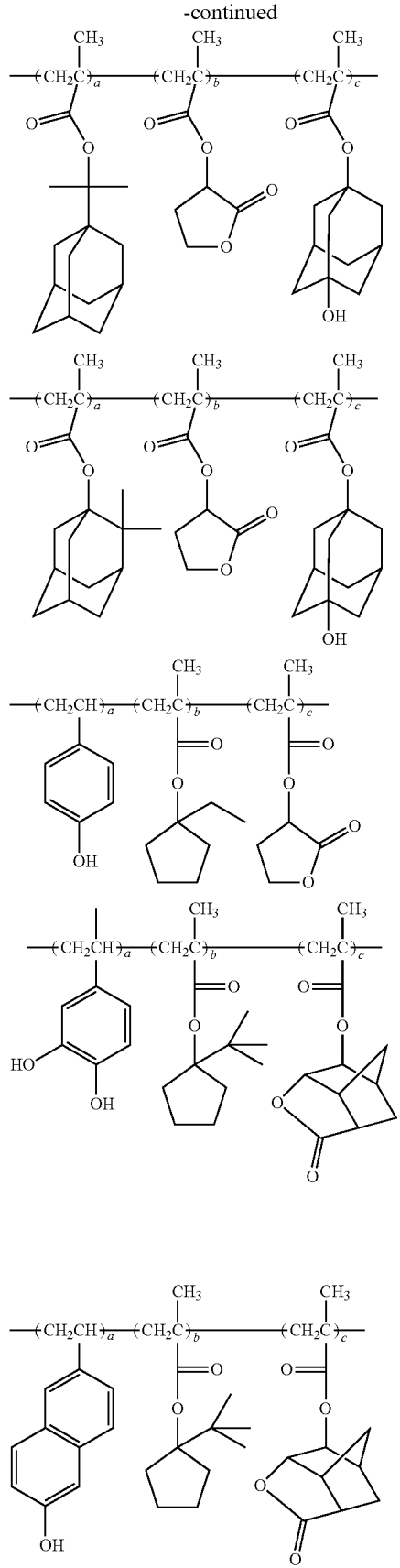
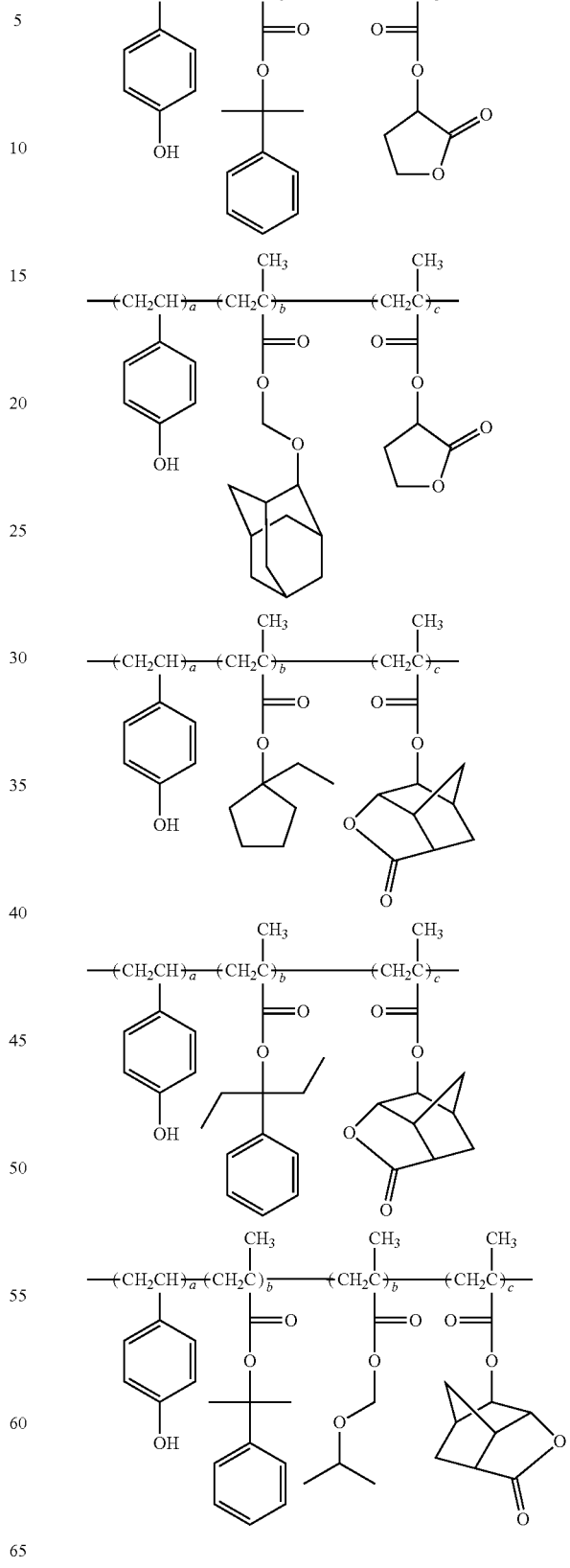

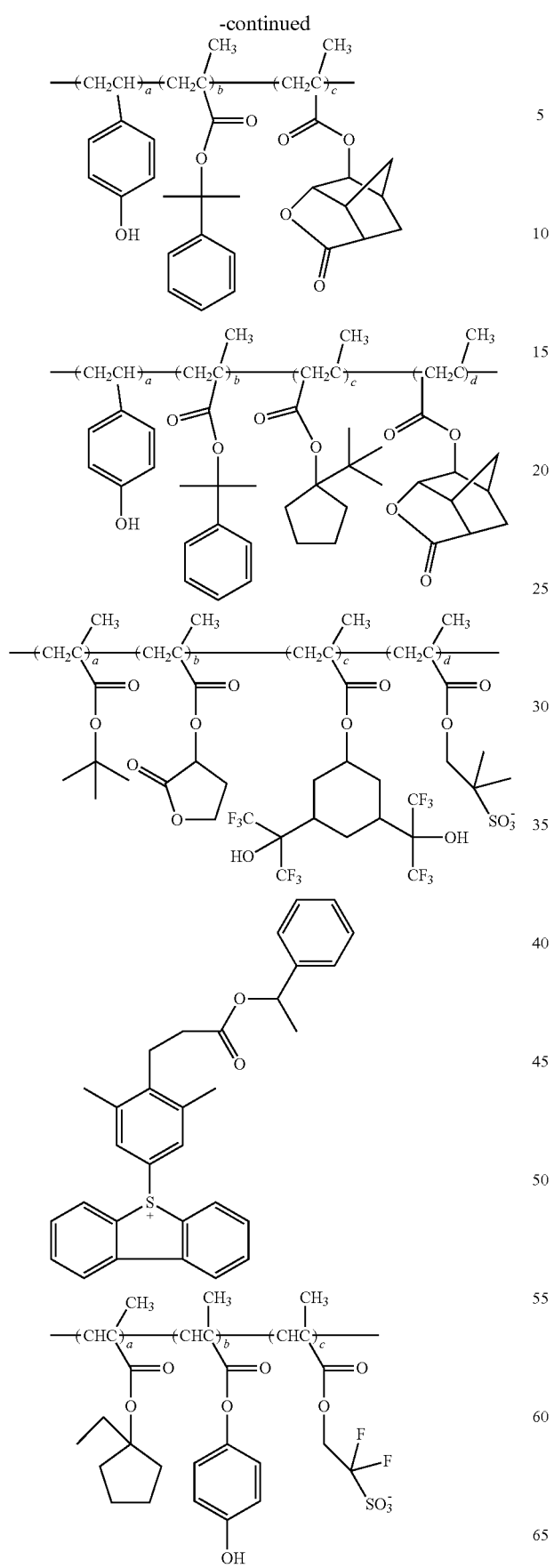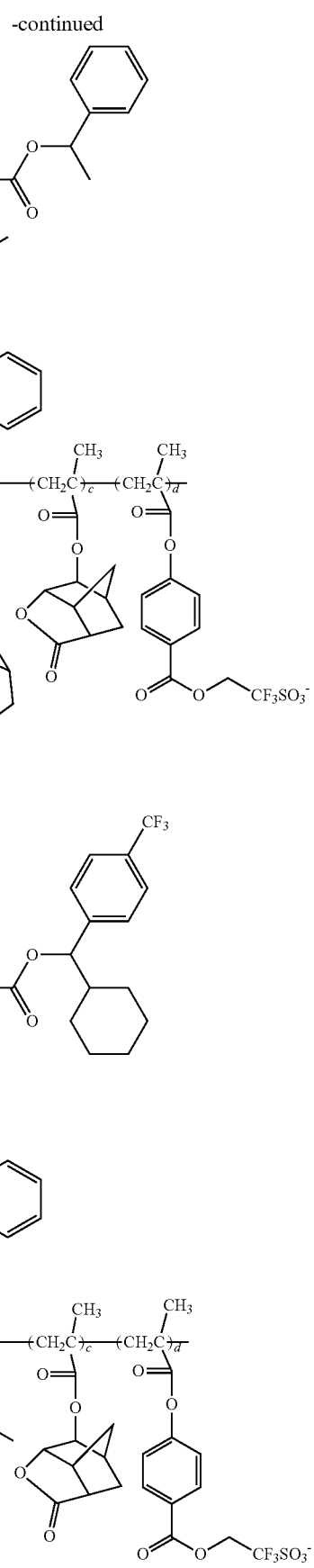

-continued

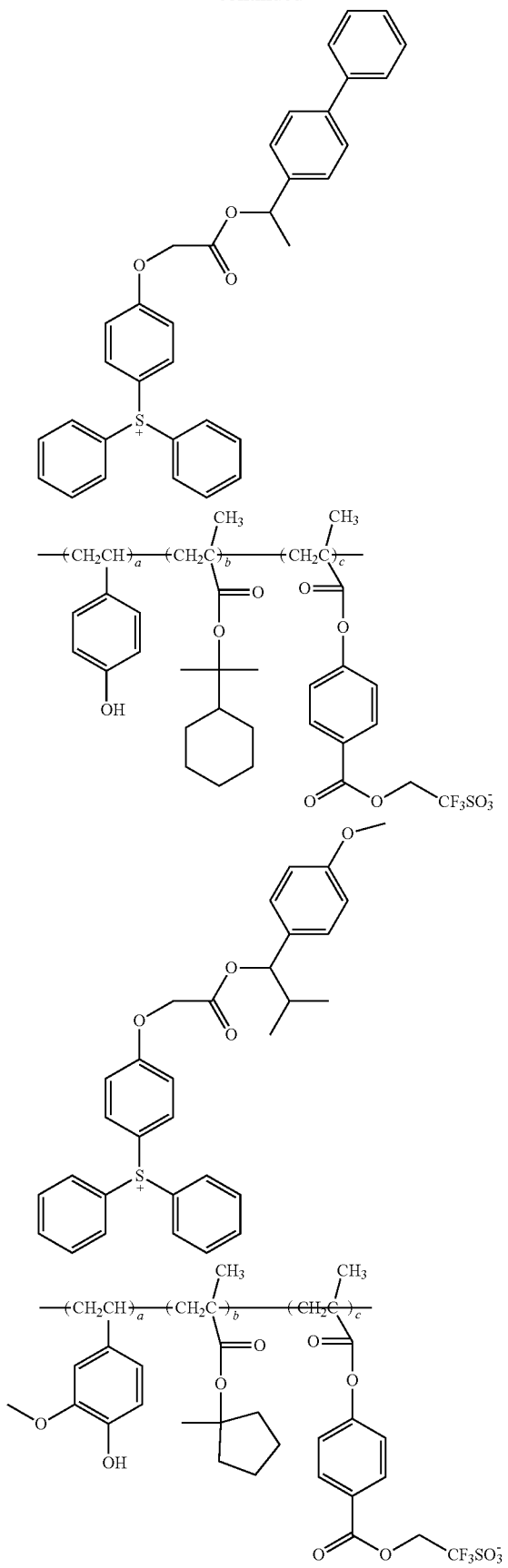

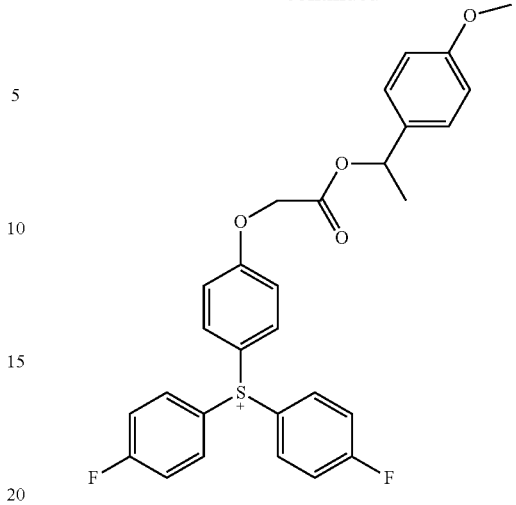

wherein a, b, c, and d represent mole fractions of the corresponding repeating units.

The acid-sensitive polymer typically has a weight average molecular weight (Mw) of 1,000 to 50,000 Daltons (Da), specifically 2,000 to 30,000 Da, more specifically 3,000 to 20,000 Da, still more specifically 3,000 to 10,000 Da. The polydispersity index (PDI) of the acid-sensitive polymer, which is the ratio of Mw to number average molecular weight (Mn) is typically 1.1 to 3, specifically 1.1 to 2. Molecular weight values are determined by gel permeation chromatography (GPC) using polystyrene standards.

The acid-sensitive polymer and any other polymers in the photoresist composition may be prepared using suitable methods known in the art. For example, one or more monomers corresponding to the repeating units of the polymer may be combined or fed separately with suitable solvent(s) and initiator, and polymerized in a reactor. The polymer may be obtained by polymerization under any suitable conditions, such as by heating at an effective temperature, irradiation with actinic radiation at an effective wavelength, or a combination thereof.

The photoresist compositions may further include a basic quencher and/or a photo-decomposable quencher (PDQ) (also known as a photo-decomposable base). If used, the content of each is typically from 0.01 to 10 wt %, based on total solids of the photoresist composition.

Exemplary basic quenchers include, for example: linear aliphatic amines such as tributylamine, trioctylamine, triisopropanolamine, tetrakis(2-hydroxypropyl)ethylenediamine: n-tert-butyldiethanolamine, tris(2-acetoxy-ethyl) amine, 2,2',2'',2'''-(ethane-1,2-diylbis(azanetriyl))tetraethanol, 2-(dibutylamino)ethanol, and 2,2',2''-nitrilotriethanol; cyclic aliphatic amines such as 1-(tert-butoxycarbonyl)-4-hydroxypiperidine, tert-butyl 1-pyrrolidinecarboxylate, tert-butyl 2-ethyl-1H-imidazole-1-carboxylate, di-tert-butyl piperazine-1,4-dicarboxylate, and N-(2-acetoxy-ethyl) morpholine; aromatic amines such as pyridine, di-tert-butyl pyridine, and pyridinium; linear and cyclic amides and derivatives thereof such as N,N-bis(2-hydroxyethyl)pivalamide, N,N-diethylacetamide, N1,N1,N3,N3-tetrabutylmalonamide, 1-methylazepan-2-one, 1-allylazepan-2-one, and tert-butyl 1,3-dihydroxy-2-(hydroxymethyl)propan-2-ylcarbamate; ammonium salts such as quaternary ammonium salts of sulfonates, sulfamates, carboxylates, and phosphonates; imines such as primary and secondary aldimines and ketimines; diazines such as optionally substituted pyrazine, piperazine, and phenazine; diazoles such as optionally substituted pyrazole, thiadiazole, and imidazole; and optionally substituted pyrrolidones such as 2-pyrrolidone and cyclohexyl pyrrolidine.

Photo-decomposable quenchers PDQs generate a relatively weak acid upon irradiation that does not react rapidly with acid-labile groups in the photoresist composition. Exemplary photo-decomposable quenchers include, for example, photo-decomposable cations, and preferably those also useful for preparing strong acid generators but paired with an anion of a weak acid such as, for example, a $C_{1-20}$ carboxylic acid or $C_{1-20}$ sulfonic acid. Exemplary carboxylic acids include formic acid, acetic acid, propionic acid, tartaric acid, succinic acid, cyclohexanecarboxylic acid, benzoic acid, salicylic acid, and the like. Exemplary carboxylic acids include p-toluene sulfonic acid, camphor sulfonic acid and the like. In a preferred embodiment, the photo-decomposable quencher is a photo-decomposable organic zwitterion compound such as diphenyliodonium-2-carboxylate.

The photoresist composition may include one or more photoacid generators in addition to the PAG of the present invention. Such additional PAG is typically of non-polymeric form, but may be in polymeric form, for example, present in a polymerized repeating unit of an acid-sensitive polymer or as part of a different polymer. Suitable PAG compounds include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; di-t-butyphenyliodonium perfluorobutanesulfonate, and di-t-butyphenyliodonium camphorsulfonate. Non-ionic sulfonates and sulfonyl compounds are also known to function as photoacid generators, e.g., nitrobenzyl derivatives, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenesulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine. Other suitable sulfonate PAGs include sulfonated esters and sulfonyloxy ketones, nitrobenzyl esters, s-triazine derivatives, benzoin tosylate, t-butylphenyl α-(p-toluenesulfonyloxy)-acetate, and t-butyl α-(p-toluenesulfonyloxy)-acetate. Of these, onium salts such as sulfonium or iodonium salts are typical. Such additional PAG if present is present in an amount of from 1 to 65 wt %, more typically from 5 to 55 wt %, and still more typically from 8 to 30 wt %, based on total solids of the photoresist composition.

The photoresist composition may further include a material that comprises one or more base-labile groups (a "base-labile material"). As referred to herein, base-labile groups are functional groups that can undergo cleavage reaction to provide polar groups such as hydroxyl, carboxylic acid, sulfonic acid, and the like, in the presence of an aqueous alkaline developer after exposure and post-exposure baking steps. The base-labile group will not react significantly (e.g., will not undergo a bond-breaking reaction) prior to a development step of the photoresist composition that comprises the base-labile group. Thus, for instance, a base-labile group will be substantially inert during pre-exposure soft-bake, exposure, and post-exposure bake steps. By "substantially inert" it is meant that preferably of the base-labile groups (or moieties) will decompose, cleave, or react during the pre-exposure soft-bake, exposure, and post-exposure bake steps. The base-labile group is reactive under typical photoresist development conditions using, for example, an aqueous alkaline photoresist developer such as a 0.26 normal (N) aqueous solution of tetramethylammonium hydroxide (TMAH). For example, a 0.26 N aqueous solution of TMAH may be used to develop the resist pattern using a single puddle development or dynamic development process, e.g., where the 0.26 N TMAH developer is dispensed onto an imaged photoresist layer for a suitable time such as 10 to 120 seconds. An exemplary base-labile group is an ester group, typically a fluorinated ester group. Preferably, the base-labile material is substantially not miscible with and has a lower surface energy than other solid components of the photoresist composition. When coated on a substrate, the base-labile material can thereby segregate from other solid components of the photoresist composition to the top surface of the formed photoresist layer.

The base-labile material is preferably a polymeric material, also referred to herein as a base-labile polymer, which may include one or more repeating units comprising one or more base-labile groups. For example, the base-labile polymer may comprise a repeating unit comprising 2 or more base-labile groups that are the same or different. A preferred base-labile polymer comprises at least one repeating unit comprising 2 or more base-labile groups, for example a repeating unit comprising 2 or 3 base-labile groups.

The base-labile polymer may be a polymer comprising a repeating unit derived from a monomer of formula (E1)

(E1)

wherein $X^b$ is a polymerizable group selected from vinyl and acrylic, $L^5$ is a divalent linking group comprising one or more of substituted or unsubstituted linear or branched $C_{1-20}$ alkylene, substituted or unsubstituted $C_{3-20}$ cycloalkylene, —C(O)—, or —C(O)O—; and $R^k$ is a substituted or unsubstituted $C_{1-20}$ fluoroalkyl group provided that the carbon atom bonded to the carbonyl (C=O) in formula (E1) is substituted with at least one fluorine atom.

Exemplary monomers of formula (E1) include the following:

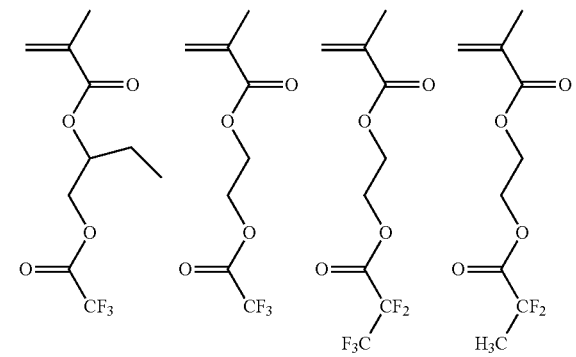

The base-labile polymer may include a repeating unit including two or more base-labile groups. For example, the base-labile polymer can include a repeating unit derived from a monomer of formula (E2)

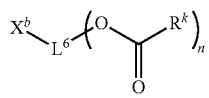
(E2)

wherein $X^b$ and $R^k$ are as defined in formula (E1); $L^6$ is a polyvalent linking group comprising one or more of substituted or unsubstituted straight chain or branched $C_{1-20}$ alkylene, substituted or unsubstituted $C_{3-20}$ cycloalkylene, —C(O)—, or —C(O)O—; and n is an integer of 2 or more, for example 2 or 3.

Exemplary monomers of formula (E2) include the following:

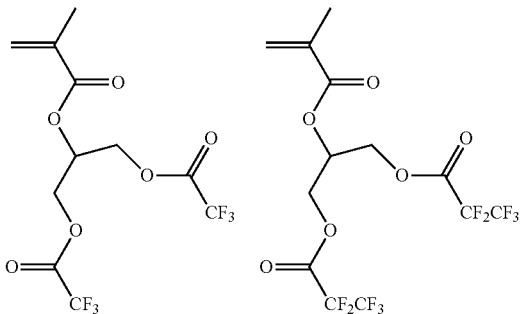

The base-labile polymer may include a repeating unit including one or more base-labile groups. For example, the base-labile polymer can include a repeating unit derived from a monomer of formula (E3):

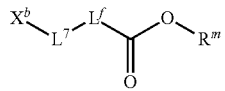
(E3)

wherein $X^b$ is as defined in formula (E1); $L^7$ is a divalent linking group comprising one or more of substituted or unsubstituted straight chain or branched $C_{1-20}$ alkylene, substituted or unsubstituted $C_{3-20}$ cycloalkylene, —C(O)—, or —C(O)O—; $L^f$ is a substituted or unsubstituted $C_{1-20}$ fluoroalkylene group wherein the carbon atom bonded to the carbonyl (C=O) in formula (E1) is substituted with at least one fluorine atom; and $R^m$ is substituted or unsubstituted straight chain or branched $C_{1-20}$ alkyl, or substituted or unsubstituted $C_{3-20}$ cycloalkyl.

Exemplary monomers of formula (E3) include the following:

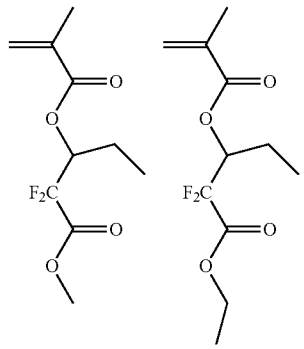 [SMILES: C=C(C)C(=O)OC(CC)C(F)(F)C(=O)OC ; C=C(C)C(=O)OC(CC)C(F)(F)C(=O)OCC]

In a further preferred aspect of the invention, a base-labile polymer may comprise one or more base-labile groups and one or more acid-labile groups, such as one or more acid-labile ester moieties (e.g. t-butyl ester) or acid-labile acetal groups. For example, the base-labile polymer may comprise a repeating unit including a base-labile group and an acid-labile group, i.e., wherein both a base-labile group and an acid-labile group are present on the same repeating unit. In another example, the base-labile polymer may comprise a first repeating unit comprising a base-labile group and a second repeating unit comprising an acid-labile group. Preferred photoresists of the invention can exhibit reduced defects associated with a resist relief image formed from the photoresist composition. If present, the content of the base-labile polymer is typically from 0.01 to 10 wt %, based on total solids of the photoresist composition.

The base-labile polymer may be prepared using any suitable methods in the art, including those described herein for the first and second polymers. For example, the base-labile polymer may be obtained by polymerization of the respective monomers under any suitable conditions, such as by heating at an effective temperature, irradiation with actinic radiation at an effective wavelength, or a combination thereof. Additionally, or alternatively, one or more base-labile groups may be grafted onto the backbone of a polymer using suitable methods.

The photoresist composition may further include one or more additional optional additives. For example, optional additives may include actinic and contrast dyes, anti-striation agents, plasticizers, speed enhancers, sensitizers, surfactants, and the like, or combinations thereof. If present, the content of each optional additive is typically from 0.01 to 10 wt %, based on total solids of the photoresist composition.

Exemplary surfactants include fluorinated and non-fluorinated surfactants and can be ionic or non-ionic, with non-ionic surfactants being preferable. Exemplary fluorinated non-ionic surfactants include perfluoro $C_4$ surfactants such as FC-4430 and FC-4432 surfactants (3M Corporation); and fluorodiols such as POLYFOX PF-636, PF-6320, PF-656, and PF-6520 fluorosurfactants (Omnova).

The photoresist compositions further include a solvent for dissolving the components of the composition and facilitating its coating on a substrate. Preferably, the solvent is an organic solvent conventionally used in the manufacture of electronic devices. Suitable solvents include, for example: aliphatic hydrocarbons such as hexane and heptane; aromatic hydrocarbons such as toluene and xylene; halogenated hydrocarbons such as dichloromethane, 1,2-dichloroethane and 1-chlorohexane; alcohols such as methanol, ethanol, 1-propanol, iso-propanol, tert-butanol, 2-methyl-2-butanol, 4-methyl-2-pentanol, and diacetone alcohol (4-hydroxy-4-methyl-2-pentanone); propylene glycol monomethyl ether (PGME); ethers such as diethyl ether, tetrahydrofuran, 1,4-dioxane and anisole; ketones such as acetone, methyl ethyl ketone, methyl iso-butyl ketone, 2-heptanone and cyclohexanone (CHO); esters such as ethyl acetate, n-butyl acetate, propylene glycol monomethyl ether acetate (PGMEA), ethyl lactate (EL), hydroxyisobutyrate methyl ester (HBM) and ethyl acetoacetate; lactones such as gamma-butyrolactone (GBL) and epsilon-caprolactone; lactams such as N-methyl pyrrolidone; nitriles such as acetonitrile and propionitrile; cyclic or non-cyclic carbonate esters such as propylene carbonate, dimethyl carbonate, ethylene carbonate, propylene carbonate, diphenyl carbonate, and propylene carbonate; polar aprotic solvents such as dimethyl sulfoxide and dimethyl formamide; water; and combinations thereof. Of these, preferred solvents are PGME, PGMEA, EL, GBL, HBM, CHO, and combinations thereof. The total solvent content (i.e., cumulative solvent content for all solvents) in the photoresist compositions is typically from 40 to 99 wt %, for example, from 70 to 99 wt %, or from 85 to 99 wt %, based on total solids of the photoresist composition. The desired solvent content will depend, for example, on the desired thickness of the coated photoresist layer and coating conditions.

The photoresist compositions can be prepared following known procedures. For example, the compositions can be prepared by dissolving solid components of the photoresist composition in the solvent. The photoresist compositions or one or more of the components of the compositions can optionally be subjected to one or more purification processes, for example, filtration and/or ion exchange processes. The desired total solids content of the compositions will depend on factors such as the desired final layer thickness. The solids content of the photoresist compositions is typically from 1 to 10 wt %, more preferably from 1 to 5 wt %, based on the total weight of the composition.

Pattern Formation Methods

Patterning methods using the photoresist compositions of the invention are described below. Suitable substrates on which the photoresist compositions can be coated include electronic device substrates. A wide variety of electronic device substrates may be used in the present invention, such as: semiconductor wafers; polycrystalline silicon substrates; packaging substrates such as multichip modules; flat panel display substrates; substrates for light emitting diodes (LEDs) including organic light emitting diodes (OLEDs); and the like, with semiconductor wafers being typical. Such substrates are typically composed of one or more of silicon, polysilicon, silicon oxide, silicon nitride, silicon oxynitride, silicon germanium, gallium arsenide, aluminum, sapphire, tungsten, titanium, titanium-tungsten, nickel, copper, and gold. Suitable substrates may be in the form of wafers such as those used in the manufacture of integrated circuits, optical sensors, flat panel displays, integrated optical circuits, and LEDs. Such substrates may be any suitable size. Typical wafer substrate diameters are 200 to 300 millimeters (mm), although wafers having smaller and larger diameters may be suitably employed according to the present invention. The substrates may include one or more layers or structures which may optionally include active or operable portions of devices being formed.

Typically, one or more lithographic layers such as a hardmask layer, for example, a spin-on-carbon (SOC), amorphous carbon, or metal hardmask layer, a CVD layer such as a silicon nitride (SiN), a silicon oxide (SiO), or silicon oxynitride (SiON) layer, an organic or inorganic underlayer, or combinations thereof, are provided on an upper surface of the substrate prior to coating a photoresist composition of the present invention. Such layers, together with an overcoated photoresist layer, form a lithographic material stack.

Optionally, a layer of an adhesion promoter may be applied to the substrate surface prior to coating the photoresist compositions. If an adhesion promoter is desired, any suitable adhesion promoter for polymer films may be used, such as silanes, typically organosilanes such as trimethoxyvinylsilane, triethoxyvinylsilane, hexamethyldisilazane, or an aminosilane coupler such as gamma-aminopropyltriethoxysilane. Particularly suitable adhesion promoters include those sold under the AP 3000, AP 8000, and AP 9000S designations, available from DuPont Electronics & Imaging (Marlborough, Massachusetts).

The photoresist composition may be coated on the substrate by any suitable method, including spin coating, spray coating, dip coating, doctor blading, or the like. For example, applying the layer of photoresist may be accomplished by spin coating the photoresist in solvent using a coating track, in which the photoresist is dispensed on a spinning wafer. During dispensing, the wafer is typically spun at a speed of up to 4,000 rotations per minute (rpm), for example, from 200 to 3,000 rpm, for example, 1,000 to 2,500 rpm, for a period of from 15 to 120 seconds to obtain a layer of the photoresist composition on the substrate. It will be appreciated by those skilled in the art that the thickness of the coated layer may be adjusted by changing the spin speed and/or the solids content of the composition. A photoresist layer formed from the compositions of the invention typically has a dried layer thickness of from 10 to 200 nanometers (nm), preferably from 15 to 100 nm, and more preferably from 20 to 60 nm The photoresist composition is typically next soft-baked to minimize the solvent content in the layer, thereby forming a tack-free coating and improving adhesion of the layer to the substrate. The soft bake is performed, for example, on a hotplate or in an oven, with a hotplate being typical. The soft bake temperature and time will depend, for example, on the particular photoresist composition and thickness. The soft bake temperature is typically from 90 to 170° C., for example, from 110 to 150° C. The soft bake time is typically from 10 seconds to 20 minutes, for example, from 1 minute to 10 minutes, or from 1 minute to 5 minutes. The heating time can be readily determined by one of ordinary skill in the art based on the ingredients of the composition.

The photoresist layer is next pattern-wise exposed to activating radiation to create a difference in solubility between exposed and unexposed regions. Reference herein to exposing a photoresist composition to radiation that is activating for the composition indicates that the radiation is capable of forming a latent image in the photoresist composition. The exposure is typically conducted through a patterned photomask that has optically transparent and optically opaque regions corresponding to regions of the resist layer to be exposed and unexposed, respectively. Such exposure may, alternatively, be conducted without a photomask in a direct writing method, typically used for e-beam lithography. The activating radiation typically has a wavelength of sub-400 nm, sub-300 nm or sub-200 nm, with 248 nm (KrF), 193 nm (ArF), and 13.5 nm (extreme ultraviolet, EUV) wavelengths or e-beam lithography being preferred. The methods find use in immersion or dry (non-immersion) lithography techniques. The exposure energy is typically from 1 to 200 millijoules per square centimeter (mJ/cm$^2$), preferably 10 to 100 mJ/cm$^2$ and more preferably 20 to 50 mJ/cm$^2$, dependent upon the exposure tool and components of the photoresist composition. In some aspects, the activating radiation is EUV at a wavelength of 13.5 nm.

Following exposure of the photoresist layer, a post-exposure bake (PEB) of the exposed photoresist layer is performed. The PEB can be conducted, for example, on a hotplate or in an oven, with a hotplate being typical. Conditions for the PEB will depend, for example, on the particular photoresist composition and layer thickness. The PEB is typically conducted at a temperature of from 80 to 150° C., and a time of from 30 to 120 seconds. A latent image defined by the polarity-switched (exposed regions) and unswitched regions (unexposed regions) is formed in the photoresist.

The exposed photoresist layer is then developed with a suitable developer to selectively remove those regions of the layer that are soluble in the developer while the remaining insoluble regions form the resulting photoresist pattern relief image. In the case of a positive-tone development (PTD) process, the exposed regions of the photoresist layer are removed during development and unexposed regions remain. Conversely, in a negative-tone development (NTD) process, the exposed regions of the photoresist layer remain, and unexposed regions are removed during development. Application of the developer may be accomplished by any suitable method such as described above with respect to application of the photoresist composition, with spin coating being typical. The development time is for a period effective to remove the soluble regions of the photoresist, with a time of from 5 to 60 seconds being typical. Development is typically conducted at room temperature.

Suitable developers for a PTD process include aqueous base developers, for example, quaternary ammonium hydroxide solutions such as tetramethylammonium hydroxide (TMAH), preferably 0.26 normal (N) TMAH, tetraethylammonium hydroxide, tetrabutylammonium hydroxide, sodium hydroxide, potassium hydroxide, sodium carbonate, potassium carbonate, and the like. Suitable developers for an NTD process are organic solvent-based, meaning the cumulative content of organic solvents in the developer is 50 wt % or more, typically 95 wt % or more, 95 wt % or more, 98 wt % or more, or 100 wt %, based on total weight of the developer. Suitable organic solvents for the NTD developer include, for example, those chosen from ketones, esters, ethers, hydrocarbons, and mixtures thereof. The developer is typically 2-heptanone or n-butyl acetate.

A coated substrate may be formed from the photoresist compositions of the invention. Such a coated substrate includes: (a) a substrate having one or more layers on a surface thereof; and (b) a layer of the photoresist composition over the one or more layers.

The photoresist pattern may be used, for example, as an etch mask, thereby allowing the pattern to be transferred to one or more sequentially underlying layers by known etching techniques, typically by dry-etching such as reactive ion etching. The photoresist pattern may, for example, be used for pattern transfer to an underlying hardmask layer which, in turn, is used as an etch mask for pattern transfer to one or more layers below the hardmask layer. If the photoresist pattern is not consumed during pattern transfer, it may be removed from the substrate by known techniques, for example, oxygen plasma ashing or a wet strip process. The photoresist compositions may, when used in one or more such patterning processes, be used to fabricate semiconductor devices such as memory devices, processor chips (CPUs), graphics chips, optoelectronic chips, LEDs, OLEDs, as well as other electronic devices.

The following non-limiting examples are illustrative of the invention.

EXAMPLES

PAG Synthesis

Example 1

PAG A1 was prepared in accordance with Scheme 1 as described below:

Scheme 1

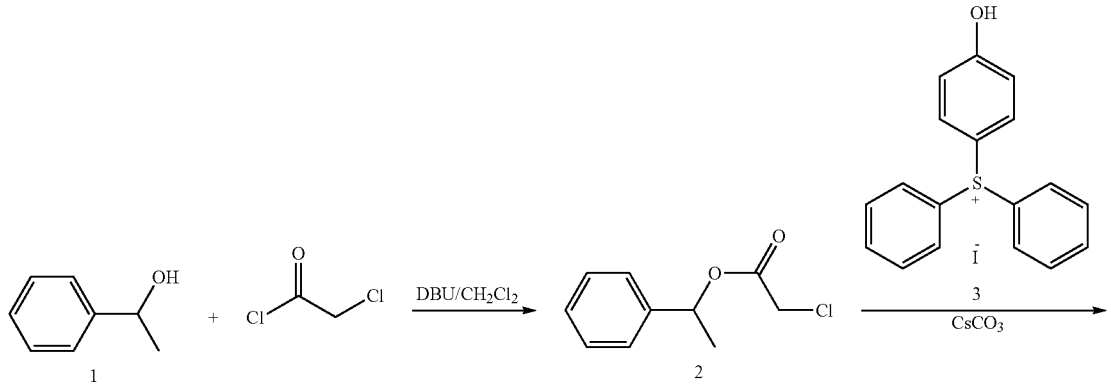

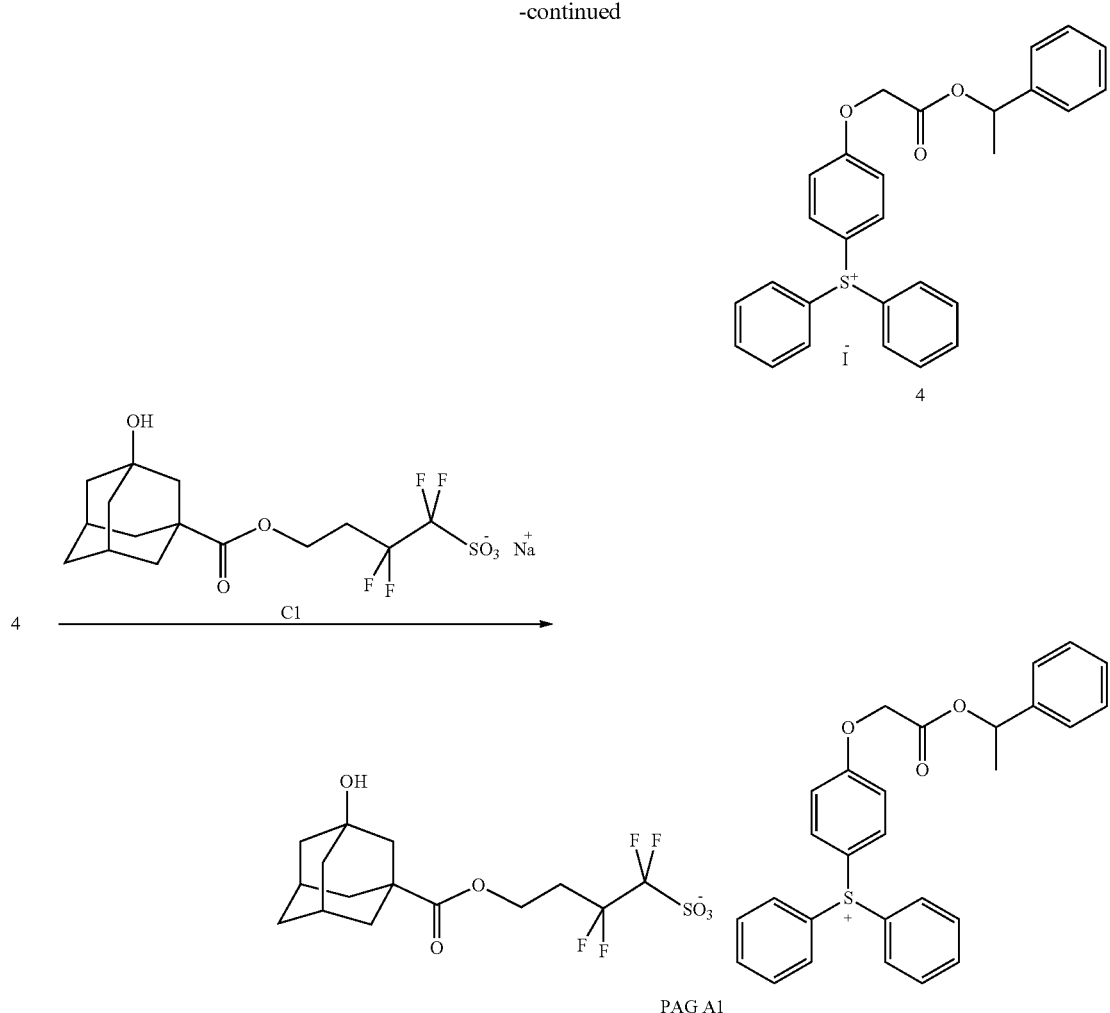

PAG A1

To a stirred solution of (±)-1-Phenylethanol (compound 1, 50 g, 0.40 mol) and 1,8-diazabicycloundec-7-ene (DBU, 63 g, 0.40 mol) in methylene chloride (300 mL) at 0° C. was added dropwise chloroacetyl chloride (46.0 g, 0.40 mol). The mixture was allowed to warm up to room temperature and stirring continued for 8 hours. The organic phase was washed with saturated solution of aqueous ammonium chloride (2×250 mL) and then washed with water (2×250 mL). The solvent was removed from the organic phase to produce the crude product. The crude product was dissolved in 20 mL heptane and passed through a short plug of silica-gel initially using heptane as eluent. The fractions that contained the product were combined and the heptane was fully removed under reduce pressure to produce the pure product 1-phenylethyl 2-chloroacetate (2) as colorless liquid. Yield: 35 g (43%). $^1$H NMR (acetone-d6), δ (ppm): 7.75 (d, 2H, ArH), 7.44-3.31 (m, 5H, ArH), 5.94 (q, 1H, Ar—CH), 1.56 (d, 3H, CH$_3$).

Under nitrogen atmosphere, an oven-dry flask was charged with of N,N-dimethylformamide (150 mL), compound 2 (20 g, 100 mmol) and (4-hydroxyphenyl)diphenylsulfonium iodide (compound 3, 25 g, 61.3 mmol). The resulting solution was heated to 50° C. and Cesium Carbonate (25 g, 129.6 mmol) was added in one portion. The reaction mixture was stirred at the same temperature for 36 hours and then cooled to room temperature. The mixture was filtered to remove insoluble salts and the filtrate solvent was removed under reduced pressure. The remaining residue was dissolved in methylene chloride (150 mL) and washed with water (3×150 mL). Methylene chloride was removed under reduced pressure and the resulting residue was dissolved in 50 mL acetone and poured into 500 mL of methyl t-butyl ether to produce salt product 4 which was collected and dried under vacuum at 35° C. for 24 hours. Yield: 32.0 g (91%). $^1$H NMR (acetone-d6), δ (ppm): 8.20 (d, 2H, ArH), 7.98 (d, 4H, ArH), 7.88 (m, 2H, ArH), 7.83 (m, 4H, ArH), 7.41-7.29 (m, 7H, ArH), 5.96 (q, 1H, Ar—CH), 5.06 (s, 2H, OCH$_2$), 1.56 (d, 3H, CH$_3$).

To a mixture of salt 4 (10 g, 17.58 mmol) and salt C1 (8.5 g, 19.93 mmol) was added 100 mL water and 100 mL dichloromethane. The resulting mixture was stirred at room temperature for 16 hours. The organic phase was separated and washed five times each with 100 mL deionized water. The solvent from the organic phase was completely removed under reduced pressure to produce a waxy crude product. The crude product was dissolved in 50 mL acetone and poured into 500 mL methyl t-butyl ether. A waxy solid of PAG A1 obtained which was isolated by decanted the solvents dried under reduced pressure at 35° C. Yield: 7.5 g (38%). $^1$H NMR (acetone-d6), δ (ppm): 7.94 (m, 8H, ArH), 7.84 (m, 4H, ArH), 7.39 (m, 6H, ArH), 7.35 (m, 1H, ArH), 6.08 (q, 1H, Ar—CH), 5.10 (s, 2H, OCH$_2$), 4.33 (q, 2H, OCH₂), 2.77 (M, 2H, CH₂CF₂), 1.95-1.5 (14H, adamantane moiety protons). 19F NMR δ (ppm): −112.30 (2F, CF₂SO₃), −119.40 (2F, CH₂CF₂). Sample of the PAG was assayed for purity by LC-MS. The cation was determined to be >96.0% pure as detected by UV at 232 nm, and purity detected by positive ion mass spectrometry was >98%. The anion purity as measured by negative ion LC-MS was determined to be >98%.

Example 2

PAG A2 was prepared in accordance with Scheme 2 as described below:

Scheme 2

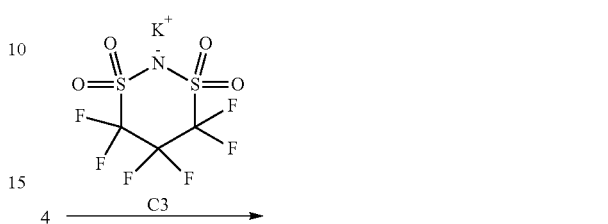

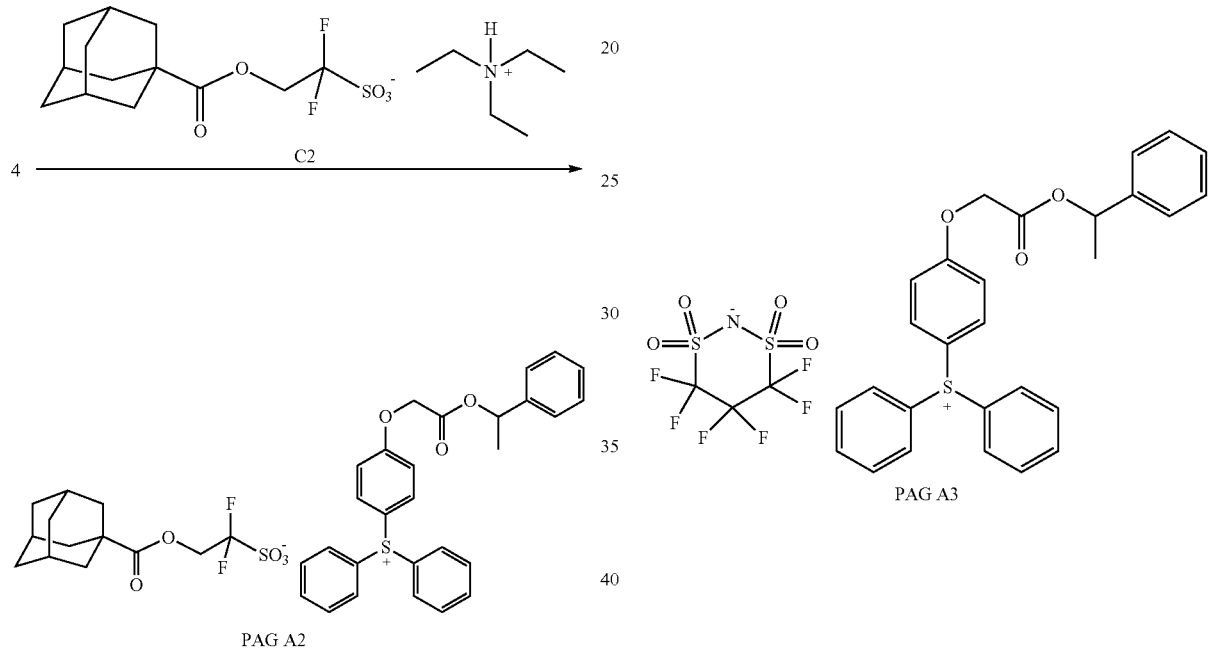

PAG A2

Example 3

PAG A3 was prepared in accordance with Scheme 3 as described below:

Scheme 3

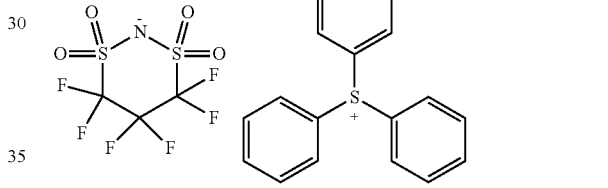

PAG A3

To a mixture of the salt 4 (10 g, 17.58 mmol) prepared as described in Example 1 and salt C2 (7.76 g, 18.27 mmol) was added 100 mL water and 100 mL dichloromethane. The resulting mixture was stirred at room temperature for 16 hours. The organic phase was separated and washed five times each with 100 mL deionized water. The solvent from the organic phase was completely removed under reduced pressure to produce a waxy crude product. The crude product was dissolved in 50 mL acetone and poured into 500 mL heptane. The product PAG A2 was collected and dried under reduced pressure at 35° C. Yield: 7.5 g (55.7%). Sample of the PAG was assayed for purity by LC-MS. The cation was determined to be >98.0% pure as detected by UV at 232 nm, and purity detected by positive ion mass spectrometry was >98%. The anion purity as measured by negative ion LC-MS was >98%. 19F NMR δ (ppm)=−110.2 (s, 2F).

To a mixture of the salt 4 (10 g, 17.58 mmol) prepared as described in Example 1 and salt C3 (6.10 g, 18.41 mmol) was added 100 mL water and 100 mL dichloromethane. The resulting mixture was stirred at room temperature for 24 hours. The organic phase was separated and washed five times each with 100 mL deionized water. The solvent from the organic phase was completely removed under reduced pressure to produce a waxy crude product. The crude product was dissolved in 50 mL acetone and poured into 500 mL heptane. The product was obtained as an oil which was isolated by decanting the solvents. The product PAG A3 was further dried under reduced pressure at 35° C. Yield: 8.7 g (67.4%). ¹H NMR (acetone-d6), δ (ppm): 7.94 (m, 8H, ArH), 7.84 (m, 4H, ArH), 7.39 (m, 6H, ArH), 7.35 (m, 1H, ArH), 6.08 (q, 1H, Ar—CH), 5.10 (s, 2H, OCH₂). Sample of the PAG was assayed for purity by LC-MS. The cation was determined to be >98.0% pure as detected by UV at 232 nm, and purity detected by positive ion mass spectrometry was >98%. The anion purity as measured by negative ion LC-MS was >98%.

Example 4

PAG A4 was prepared in accordance with Scheme 4 as described below:

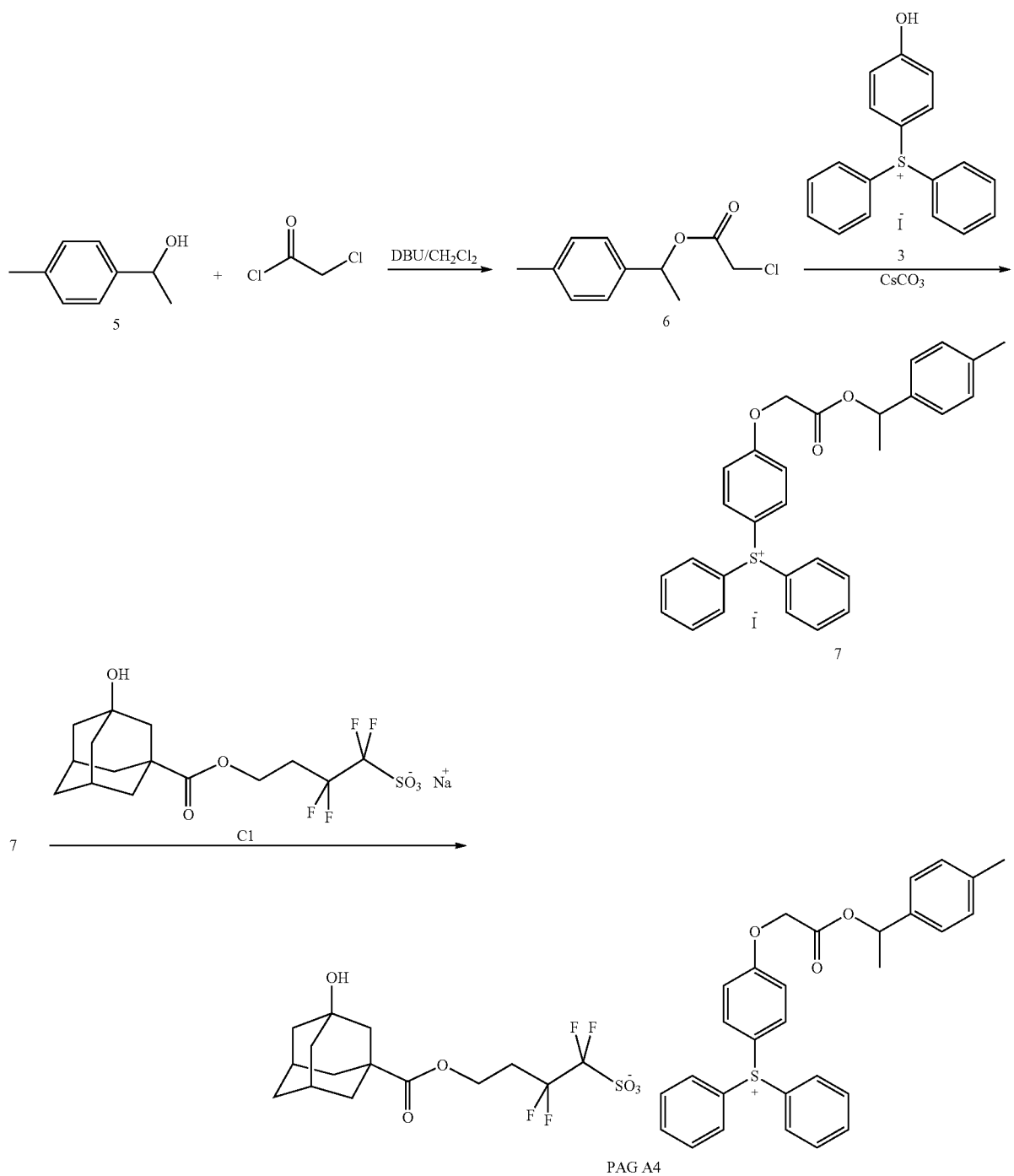

The procedure used for synthesis of compound 2 in Example 1 was used for preparation of compound 6 starting from (±)-1-(4-methylphenyl)ethanol (5) and chloroacetyl chloride. Under nitrogen atmosphere, an oven-dry flask was charged with of N,N-dimethylformamide (150 mL), compound 6 (25 g, 117.55 mmol) and (4-hydroxyphenyl)diphenylsulfonium chloride (compound 3, 20.0 g, 49.2 mmol). The resulting solution was heated to 50° C. and Cesium Carbonate (25 g, 129.6 mmol) was added in one portion. The reaction mixture was stirred at the same temperature for 36 hours and then cooled to room temperature. The mixture was filtered to remove insoluble salts and the filtrate solvent was removed under reduced pressure. The remaining residue was dissolved in methylene chloride (150 mL) and washed with water (3×150 mL). Methylene chloride was removed under reduced pressure and the resulting residue was dissolved in 50 mL acetone and poured into 500 mL of methyl t-butyl ether to produce salt product 7 which was collected and dried under vacuum at 35° C. for 24 hours. Yield: 21.5 g (75%). $^1$H NMR (acetone-d6), δ (ppm): 8.03 (d, 2H, ArH), 7.92 (d, 4H, ArH), 7.88 (m, 2H, ArH), 7.83 (m, 4H, ArH), 7.41-7.29 (7H, ArH), 5.93 (q, 1H, Ar—CH), 5.03 (s, 2H, OCH$_2$), 2.30 (s, 3H, ArCH$_3$), 1.52 (d, 3H, CH$_3$).

To a mixture of the salt 7 (10 g, 171.6 mmol) and salt C1 (11.0 g, 25.80 mmol) was added 75 mL water and 75 mL dichloromethane. The resulting mixture was stirred at room temperature for 24 hours. The organic phase was separated and washed five times each with 100 mL deionized water. The solvent from the organic phase was completely removed under reduced pressure to produce a waxy crude product. The crude product was dissolved in 50 mL acetone and poured into 500 mL heptane. The resulting PAG A4 was collected and dried under reduced pressure at 35° C. Yield: 13.5 g (67%). $^1$H NMR (acetone-d6), δ (ppm): 7.95-7.89 (8H, ArH), 7.85-7.81 (4H, ArH), 7.37 (d, 2H, ArH), 7.27 (d, 2H, ArH), 7.16 (d, 2H, ArH), 5.92 (q, 1H, Ar—CH), 5.05 (s, 2H, OCH$_2$), 4.33 (q, 2H, OCH$_2$), 2.77 (m, 2H, CH$_2$CF$_2$), 1.95-1.50 (14H, adamantane moiety protons), 1.55 (d, 3H, CH$_3$). 19F NMR δ (ppm): −112.26 (2F, CF$_2$SO$_3$), −119.37 (2F, CH$_2$CF$_2$).

Example 5

PAG A5 was prepared in accordance with Scheme 5 as described below:

Scheme 5

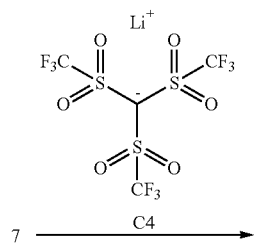

7 ——C4——→

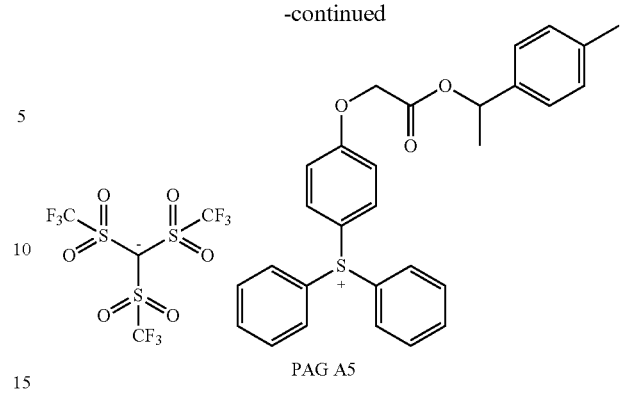

PAG A5

To a mixture of the salt 7 (10 g, 17.16 mmol) and salt C4 (11.0 g, 26.3 mmol) was added 75 mL water and 75 mL dichloromethane. The resulting mixture was stirred at room temperature for 24 hours. The organic phase was separated and washed five times each with 100 mL deionized water. The solvent from the organic phase was completely removed under reduced pressure to produce a waxy crude product. The crude product was dissolved in 50 mL acetone and poured into 500 mL heptane. The resulting PAG A5 was collected and dried under reduced pressure at 35° C. Yield: 11.6 g (78%). $^1$H NMR (acetone-d6), δ (ppm): 7.95-7.82 (12H, ArH), 7.37 (d, 2H, ArH), 7.27 (d, 2H, ArH), 7.18 (d, 2H, ArH), 5.97 (q, 1H, Ar—CH), 5.02 (s, 2H, OCH$_2$), 1.55 (d, 3H, CH$_3$). 19F NMR δ (ppm): −77.45 (9F, 3CF$_3$). A sample of the PAG was assayed for purity by LC-MS. The cation was determined to be >98.0% pure as detected by UV at 232 nm, and purity as detected by positive ion mass spectrometry was >98%. The anion purity as measured by negative ion LC-MS was >98%.

Example 6

PAG A6 was prepared in accordance with Scheme 6 as described below:

Scheme 6

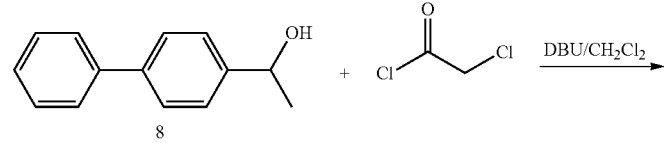

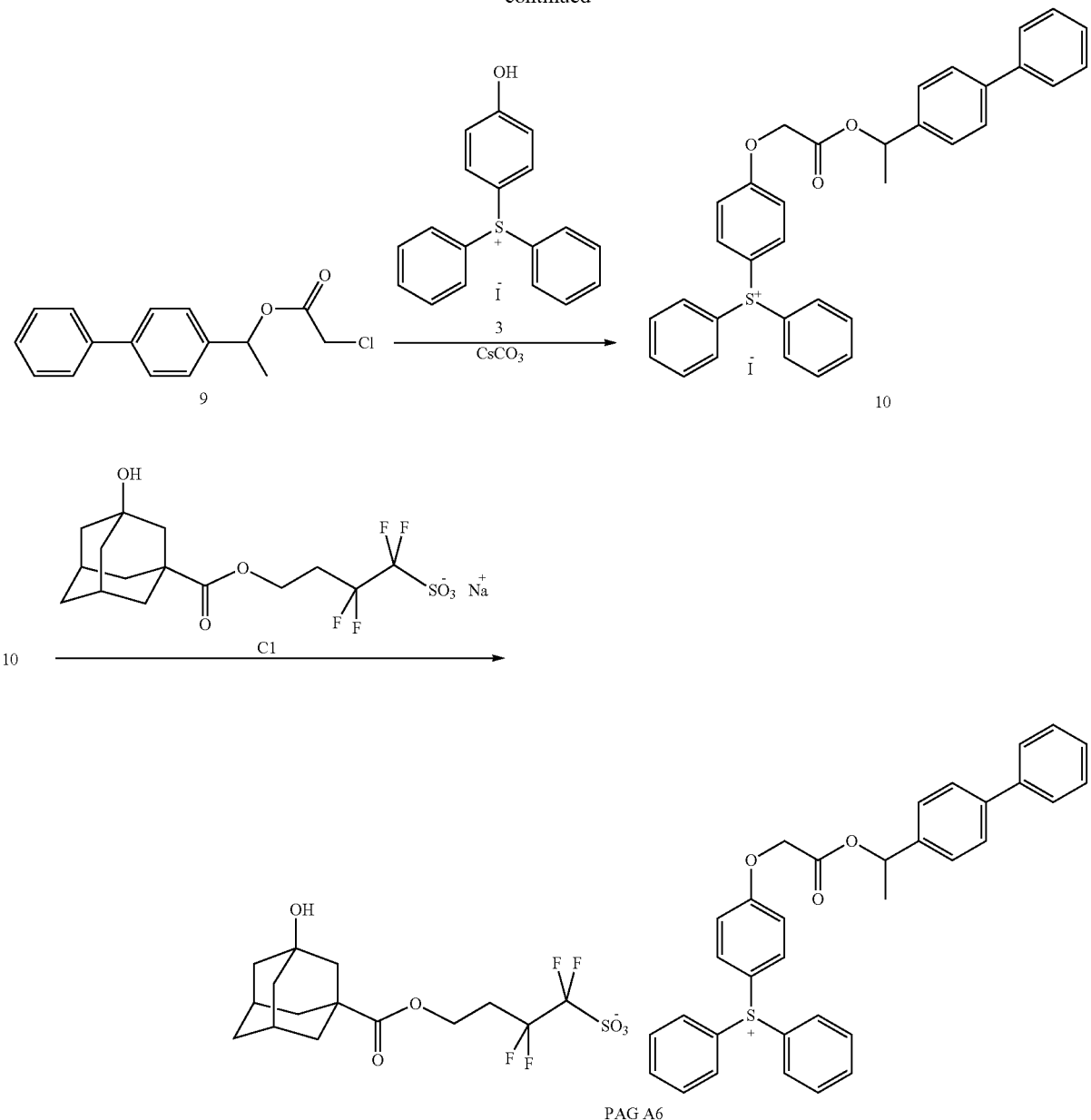

The procedure used for synthesis of compound 2 was used for preparing compound 9 starting from (±)-1-(4-bipheny) ethanol (8) and chloroacetyl chloride. Under nitrogen atmosphere, an oven-dry flask was charged with of N,N-dimethylformamide (150 mL), compound 9 (20.0 g, 72.79 mmol) and (4-hydroxyphenyl)diphenylsulfonium chloride (compound 3, 29.5 g, 72.6 mmol). The resulting solution was heated to 50° C. and Cesium Carbonate (20 g, 103.7 mmol) was added in one portion. The reaction mixture was stirred at the same temperature for 24 hours and then cooled to room temperature. The mixture was filtered to remove insoluble salts and the filtrate solvent was removed under reduced pressure. The remaining residue was dissolved in methylene chloride (150 mL) and washed with water (3×150 mL). Methylene chloride was removed under reduced pressure and the resulting residue was dissolved in 50 mL acetone and poured into 1 liter of methyl t-butyl ether to produce salt product 10 which was collected and dried under vacuum at 35° C. for 24 hours. Yield: 28.5 g (61%). To a mixture of the salt 10 (15.0 g, 23.27 mmol) and salt C1 (11.0 g, 25.8 mmol) was added 75 mL water and 75 mL dichloromethane. The resulting mixture was stirred at room temperature for 24 hours. The organic phase was separated and washed five times each with 100 mL deionized water. The solvent from the organic phase was completely removed under reduced pressure to produce a waxy crude product. The crude product was dissolved in 50 mL acetone and poured into 500 mL heptane. The resulting PAG A6 was collected and dried under reduced pressure at 35° C. Yield: 18.9 g (88%). $^1$H NMR (acetone-d6), δ (ppm): 7.94-7.79 (12H, ArH), 7.65 (4H, ArH), 7.48 (4H, ArH), 7.40 (3H, ArH), 6.10 (q, 1H, Ar—CH), 5.08 (s, 2H, OCH$_2$), 4.33 (q, 2H, OCH$_2$), 2.69 (m, 2H, CH$_2$CF$_2$), 1.80-1.57 (14H, adamantane moiety protons), 1.59 (d, 3H, CH$_3$). 19F NMR δ (ppm): −112.35 (2F, CF$_2$SO$_3$), −119.43 (2F, CH$_2$CF$_2$).

Example 7

PAG A7 was prepared in accordance with Scheme 7 as described below:

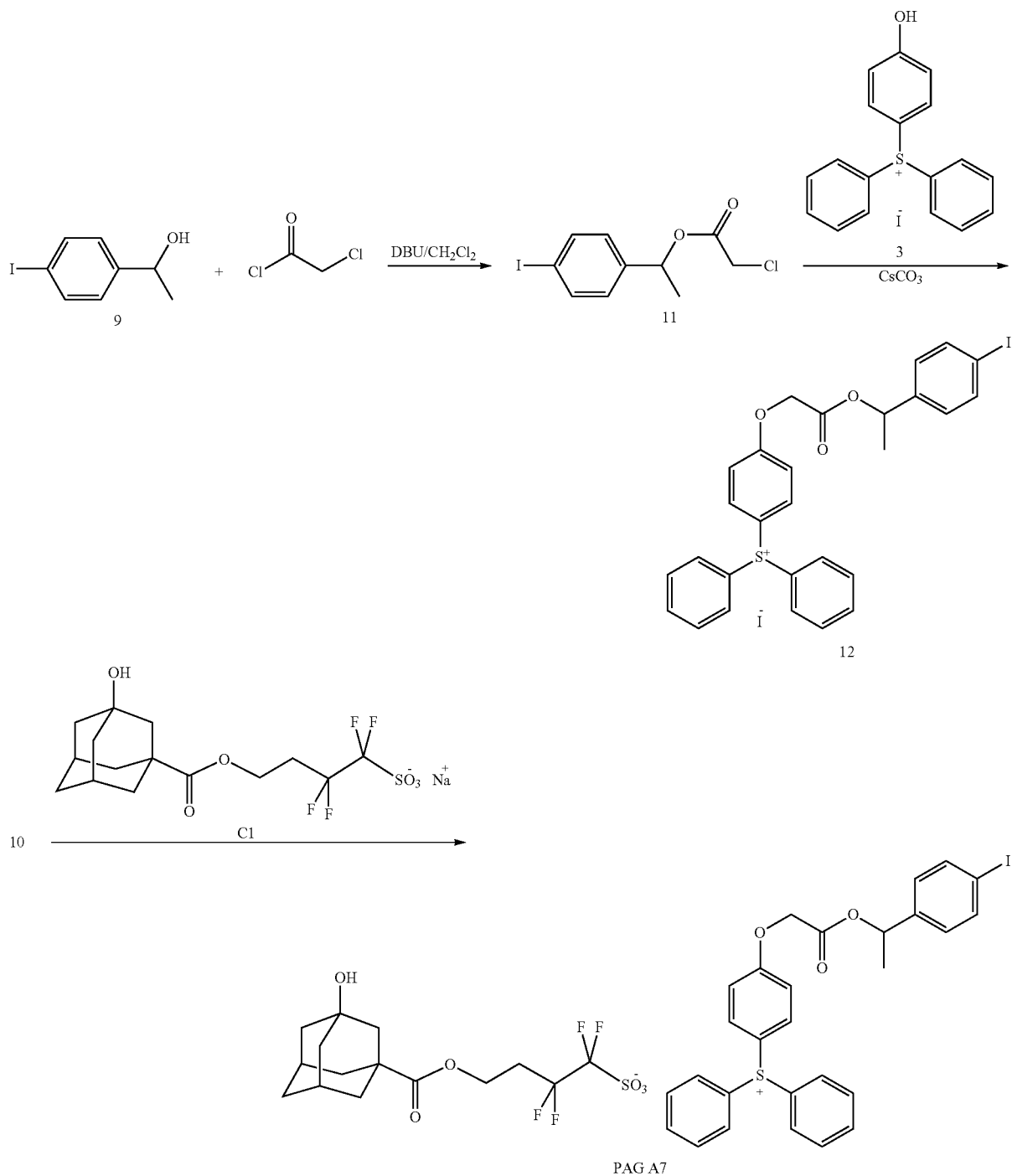

Scheme 4

PAG A7

The procedure used for synthesis of compound 2 was used for the preparation of compound 11 starting from (±)-1-(4-iodopheny)ethanol and chloroacetyl chloride. Under nitrogen atmosphere, an oven-dry flask was charged with of N,N-dimethylformamide (100 mL), compound 11 (9.0 g, 27.73 mmol) and (4-hydroxyphenyl)diphenylsulfonium chloride (compound 3, 9.0 g, 22.15 mmol). The resulting solution was heated to 50° C. and Cesium Carbonate (20 g, 103.7 mmol) was added in one portion. The reaction mixture was stirred at the same temperature for 24 hours and then cooled to room temperature. The mixture was filtered to remove insoluble salts and the filtrate solvent was removed under reduced pressure. The remaining residue was dissolved in 50 ml acetone and poured into 500 mL of methyl t-butyl ether to produce salt product 12 which was collected and dried under vacuum at 35° C. for 24 hours. Yield: 15.5 g. To a mixture of the salt 12 (8.0 g, 11.5 mmol) and salt C1 (5.2 g, 12.2 mmol) was added 75 mL water and 75 mL dichloromethane. The resulting mixture was stirred at room temperature for 24 hours. The organic phase was separated and washed five times each with 100 mL deionized water. The solvent from the organic phase was completely removed under reduced pressure to produce a waxy crude product. The crude product was dissolved in 50 mL acetone and poured into 500 mL heptane. The resulting PAG A7 was collected and dried under reduced pressure at 35° C. Yield: 7.9 g (70%). ¹H NMR (acetone-d6), δ (ppm): 7.92-7.80 (8H, ArH), 7.81-7.78 (4H, ArH), 7.37 (d, 2H, ArH), 7.27 (d, 2H, ArH), 7.16 (d, 2H, ArH), 5.98 (q, 1H, Ar—CH), 5.10 (s, 2H, OCH₂), 4.34 (q, 2H, OCH₂), 2.79 (m, 2H, CH₂CF₂), 1.95-1.50 (14H, adamantane moiety protons), 1.55 (d, 3H, CH₃). 19F NMR δ (ppm): −112.26 (2F, CF₂SO₃), −119.37 (2F, CH₂CF₂).

Example 8

PAG A8 was prepared in accordance with Scheme 8 as described below:

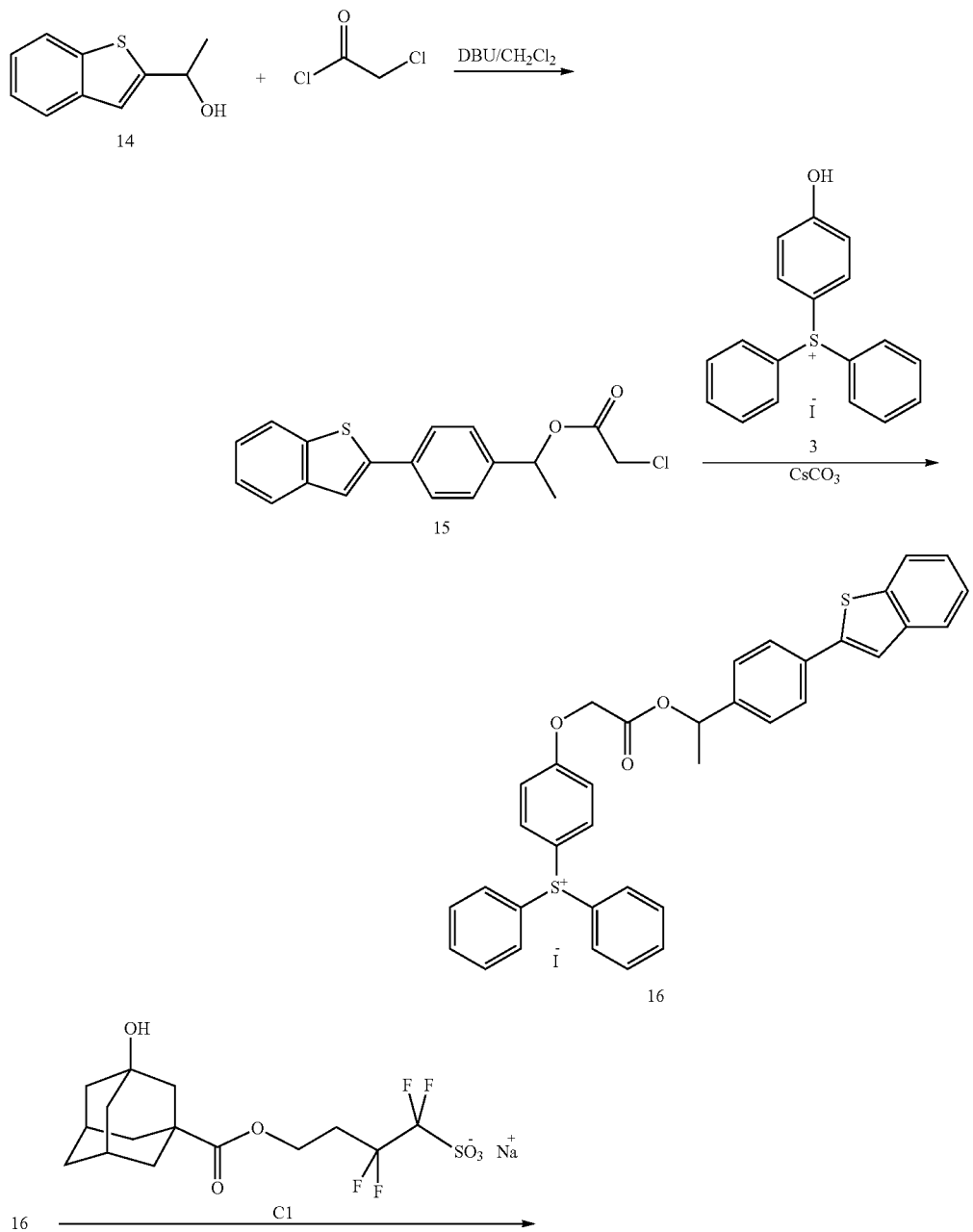

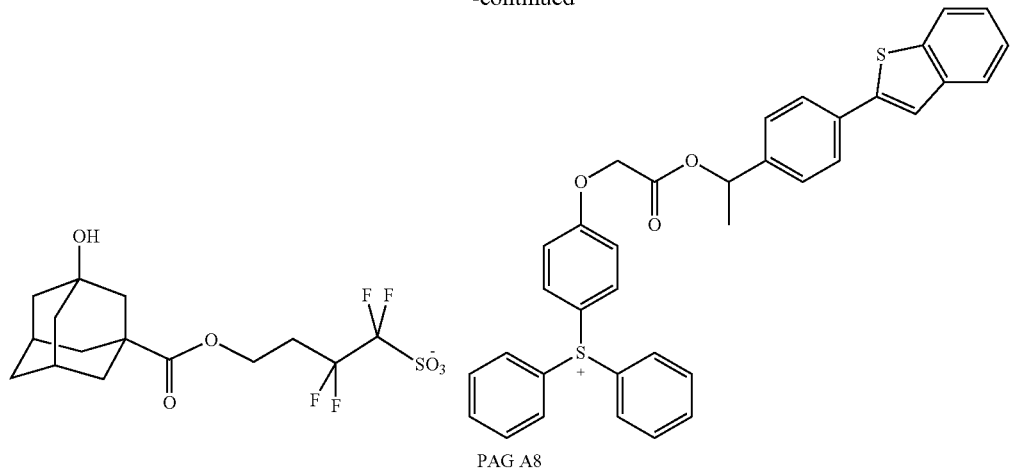

PAG A8

The procedure used for synthesis of compound 2 in Example 1 was used for preparation of compound 15 starting from 1-(benzo[b]thiophen-2-yl)ethan-1-ol (14) and chloroacetyl chloride. Under nitrogen atmosphere, an oven-dry flask was charged with of N,N-dimethylformamide (150 mL), compound 15 (8.0 g, 31.4 mmol) and (4-hydroxyphenyl)diphenylsulfonium chloride (compound 3, 8.5 g, 21 mmol). The resulting solution was heated to 50° C. and Cesium Carbonate (7.0 g, 36 mmol) was added in one portion. The reaction mixture was stirred at the same temperature for 36 hours and then cooled to room temperature. The mixture was filtered to remove insoluble salts and the filtrate solvent was removed under reduced pressure. The remaining residue was dissolved in 50 ml acetone and poured into 500 mL of methyl t-butyl ether to produce salt product 16 which was collected and dried under vacuum at 35° C. for 24 hours. Yield: 8.5 g. To a mixture of the salt 16 (8.0 g, 12.8 mmol) and salt C1 (5.5 g, 12.9 mmol) was added 75 mL water and 75 mL dichloromethane. The resulting mixture was stirred at room temperature for 24 hours. The organic phase was separated and washed five times each with 100 mL deionized water. The solvent from the organic phase was completely removed under reduced pressure to produce a waxy crude product. The crude product was dissolved in 50 mL acetone and poured into 500 mL heptane. The resulting PAG A8 was collected and dried under reduced pressure at 35° C. Yield: 6.9 g (60%). $^1$H NMR (acetone-d6), δ (ppm): 7.96-7.76 (12H, ArH), 7.40-7.30 (6H, ArH), 6.36 (q, 1H, Ar—CH), 5.07 (s, 2H, OCH$_2$), 4.30 (q, 2H, OCH$_2$), 2.69 (m, 2H, CH$_2$CF$_2$), 1.95-1.50 (14H, adamantane moiety protons), 1.55 (d, 3H, CH$_3$). 19F NMR δ (ppm): −112.4 (2F, CF$_2$SO$_3$), −119.68 (2F, CH$_2$CF$_2$).

Example 9

PAG A9 was prepared in accordance with Scheme 9 as described below:

Scheme 9

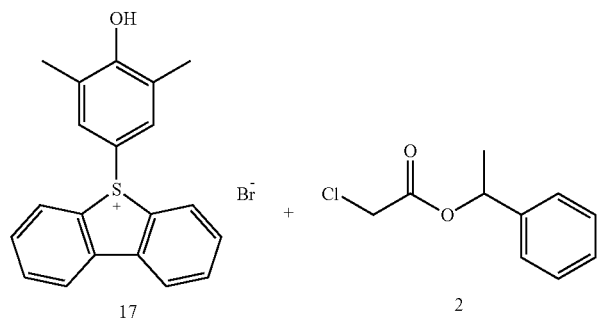

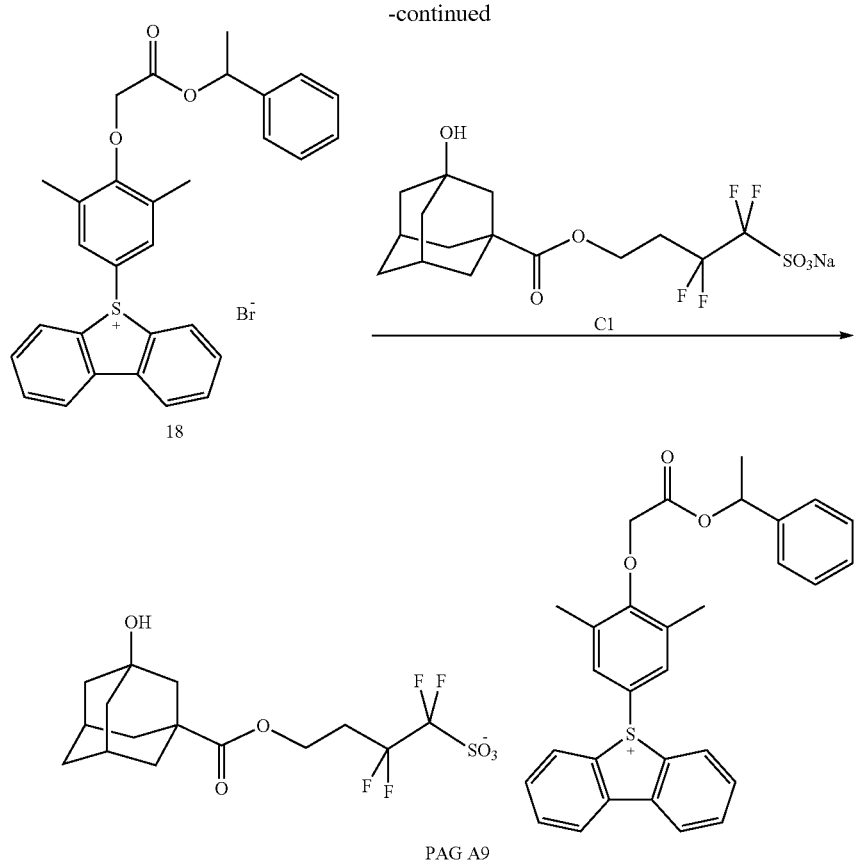

PAG A9

Under nitrogen atmosphere, an oven-dry flask was charged with N,N-dimethylformamide (250 mL), 1-phenylethyl 2-chloroacetate (compound 2, 25 g, 125.8.0 mmol) and 5-(4-hydroxy-3,5-dimethylphenyl)-5H-dibenzo[b,d]thiophenium bromide (compound 17, 38.5 g, 100 mmol). The resulting solution was heated to 50° C. and Cesium Carbonate (25.0 g, 130.0 mmol) was added in one portion. The reaction mixture was stirred at the same temperature for 36 hours and then cooled to room temperature. The mixture was filtered to remove insoluble salts and the filtrate solvent was removed under reduced pressure. Most of the N,N-dimethylformamide was removed by distillation under reduced pressure and the resulting residue was poured into saturated aqueous solution of ammonium chloride. The resulting solid was filtered, air-dried, dissolved in dichloromethane (50 mL), and poured into 500 mL methyl t-butyl ether (MTBE). The resulting residue was suspended in acetone (100 mL) to form a white solid of the salt product 18, which was filtered and dried, yielding 22.5 g. To a mixture of salt 18 (10.0 g, 18.20 mmol) and salt C1 (7.9 g, 18.52 mmol) was added 100 mL water and 100 mL dichloromethane. The resulting mixture was stirred at room temperature for 24 hours. The organic phase was separated and washed five times each with 50 mL deionized water. The solvent from the organic phase was completely removed under reduced pressure to produce a waxy crude product. The crude product was dissolved in 50 mL acetone and poured into 500 mL heptane. The resulting PAG A9 was collected and dried under reduced pressure at 35° C. Yield: 12.8 g (75%). $^1$H NMR (acetone-d6), δ (ppm): 8.53 (d, 2H, ArH), 8.37 (d, 2H, ArH), 8.03 (t, 2H, ArH), 7.83 (t, 2H, ArH), 7.52 (s, 2H, ArH), 7.41-7.30 (m, 6H, ArH), 6.0 (q, 1H, Ar—CH), 4.62 (s, 2H, OCH$_2$), 4.33 (q, 2H, OCH$_2$), 2.69 (m, 2H, CH$_2$CF$_2$), 2.30 (6H, 2CH$_3$), 1.95-1.50 (14H, adamantane moiety protons), 1.55 (d, 3H, CH$_3$). 19F NMR δ (ppm): −112.2 (2F, CF$_2$SO$_3$), −119.54 (2F, CH$_2$CF$_2$).

Example 10

PAG A10 was prepared in accordance with Scheme 10 as described below:

Scheme 10

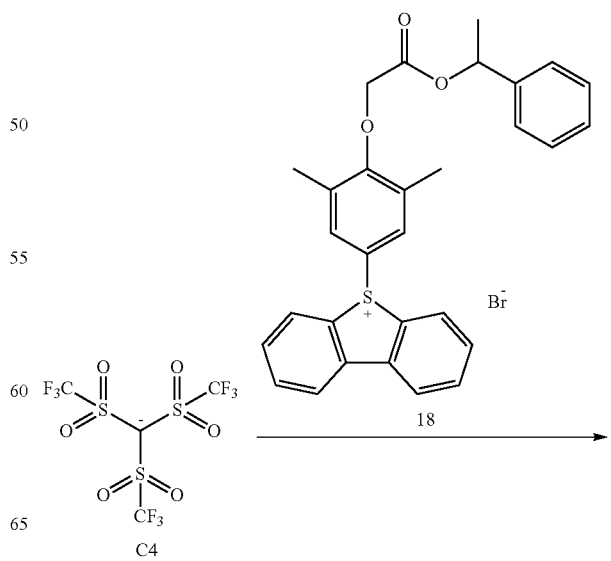

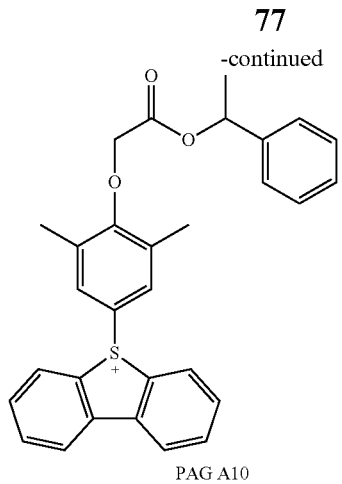

PAG A10

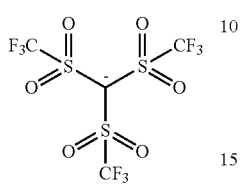

The procedure used for synthesis of PAG A9 was used for preparation of PAG A10 starting from salt C4 and salt 18. $^1$H NMR (acetone-d6), δ (ppm): 8.53 (d, 2H, ArH), 8.33 (d, 2H, ArH), 8.04 (t, 2H, ArH), 7.88 (t, 2H, ArH), 7.50 (s, 2H, ArH), 7.43-7.30 (m, 6H, ArH), 5.99 (q, 1H, Ar—CH), 4.71 (s, 2H, OCH$_2$), 2.29 (6H. 2CH$_3$), 55 (d, 3H, CH$_3$). 19F NMR δ (ppm): −77.45 (9F, 3CF$_3$).

Photoresist Compositions and Lithographic Evaluation

Photoresist compositions were prepared and lithographic processing and evaluation were conducted as described below:

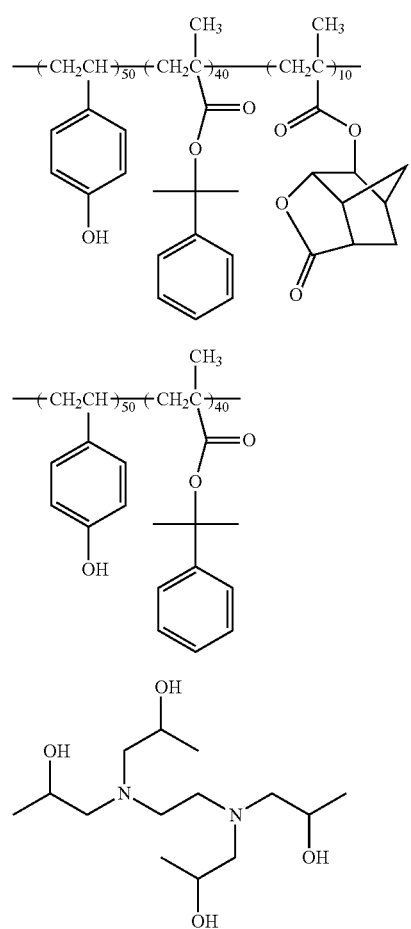

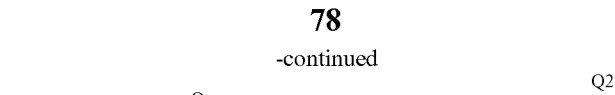

Q2

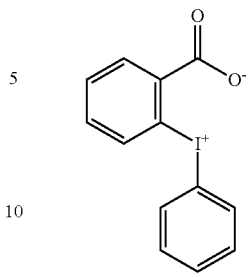

PAG-C1

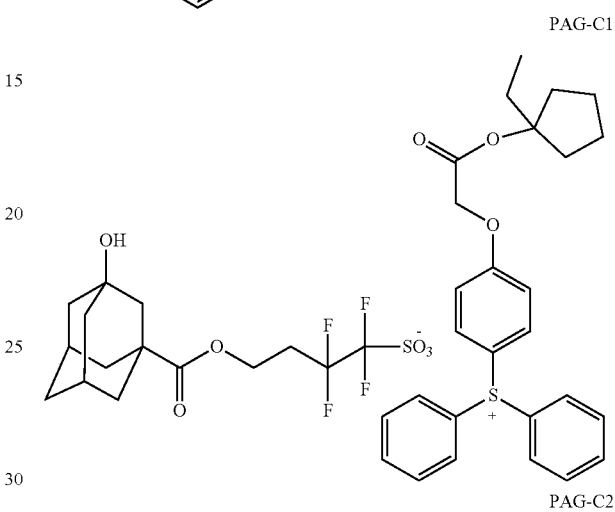

PAG-C2

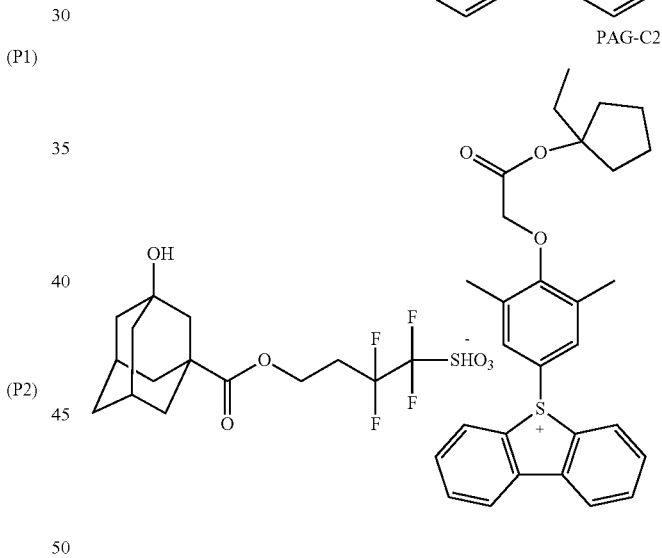

Examples 11-21

Photoresist compositions were prepared by dissolving solid components in solvents using the materials and proportions set forth in Table 1 to a total solids content of 1.5 wt %. The resulting mixtures were shaken on a mechanical shaker and then filtered through a PTFE disk-shaped filter having a 0.2 micron pore size. 200 mm silicon wafers overcoated with a BARC stack (60 nm thick AR™3 antireflectant over 80 nm thick AR™40A antireflectant [DuPont Electronics & Imaging]) were each spin-coated with a respective photoresist composition on a TEL Clean Track ACT 8 wafer track and softbaked at 110° C. for 60 seconds to provide a photoresist layer with a target thickness of about 40 nm. The resist layer thickness was measured with a THERMA-WAVE OP7350. The wafers were exposed with 248 nm radiation on a Canon FPA-5000 ES4 scanner at exposure doses between 3 and 53 mJ/cm$^2$. The wafers were post-exposure baked at 100° C. for 60 seconds, developed with MF™-CD26 TMAH developer (DuPont Electronics & Imaging) for 60 seconds, rinsed with deionized water, and dried. Photoresist layer thickness measurements were made in exposed and unexposed regions of the layer. A contrast curve for each wafer was generated by plotting the remaining photoresist layer thickness in the exposed regions vs. dose. Dose-to-clear ($E_0$) was determined from the contrast curve as the exposure dose at which the remaining photoresist layer thickness was less than 10% of the original coated thickness. Unexposed film thickness loss (UFTL) was determined based on the photoresist layer thickness measurements in the unexposed regions. The results are shown in Table 1.

having a 0.2 micron pore size. 200 mm silicon wafers overcoated with a BARC stack (60 nm thick AR™3 antireflectant over 80 nm thick AR™40A antireflectant [DuPont Electronics & Imaging]) were each spin-coated with a respective photoresist composition on a TEL Clean Track ACT 8 wafer track and softbaked at 110° C. for 60 seconds to provide a photoresist layer with a target thickness of about 40 nm. The resist layer thickness was measured with a THERMA-WAVE OP7350. The wafers were exposed with 248 nm radiation on a Canon FPA-5000 ES4 scanner at exposure doses between 3 and 53 mJ/cm$^2$. The wafers were post-exposure baked at 100° C. for 60 seconds, developed with MF™-CD26 TMAH developer (DuPont Electronics & Imaging) for 60 seconds, rinsed with deionized water, and dried. Photoresist layer thickness measurements were made in exposed regions of the layer. A contrast curve for each

TABLE 1

| Example | Resist Composition | Polymer | PAG | Base 1 | Base 2 | Solvent* | $E_0$ (mJ/cm$^2$) | UFTL (Å) |
|---|---|---|---|---|---|---|---|---|
| 11 | PR-1 | P1 [58.92] P2 [19.62] | A1 [19.81] | Q1 [0.47] | Q2 [1.18] | S1/S2 | 13.5 | 65.8 |
| 12 | PR-2 | P1 [60.05] P1 [20.02] | A2 [18.25] | Q1 [0.48] | Q2 [1.20] | S1/S2 | 10.5 | 61.4 |
| 13 | PR-3 | P1 [60.48] P1 [20.16] | A3 [17.67] | Q1 [0.48] | Q2 [1.21] | S1/S2 | 12.5 | 64.5 |
| 14 | PR-4 | P1 [59.30] P1 [19.76] | A3 [15.04] C2 [4.24] | Q1 [0.47] | Q2 [1.19] | S1/S2 | 16 | 69.8 |
| 15 (Comp) | PR-5 | P1 [59.0] P1 [19.67] | C1 [19.67] | Q1 [0.48] | Q2 [1.18] | S1/S2 | 14 | 74.0 |
| 16 (Comp) | PR-6 | P1 [59.0] P1 [19.67] | C1 [19.67] | Q1 [0.48] | Q2 [1.18] | S1/S2 | 23.5 | 72.6 |
| 17 | PR-7 | P1 [79.12] | A8 [19.30] | Q2 [1.58] | — | S1/S2 | 16.6 | 17 |
| 18 | PR-8 | P1 [79.64] | A9 [18.77] | Q2 [1.59] | — | S1/S2 | 17.5 | 17 |
| 19 | PR-9 | P1 [78.9] | A10 [19.46] | Q2 [1.58] | — | S1/S2 | 16.9 | 12 |
| 20 (Comp) | PR-10 | P1 [79.78] | C1 [18.63] | Q2 [1.59] | — | S1/S2 | 17.6 | 24 |
| 21 (Comp) | PR-11 | P1 80.23 | C2 [18.17] | Q2 [1.60] | — | S1/S2 | 14.4 | 25 |

Amounts for solids components provided in wt % based on total solids;
S1 = propylene glycol monomethyl ether acetate;
S2 = methyl 2-hydroxyisobutyrate;
*S1/S2 solvent blend is 1:1 (wt/wt);
Comp = Comparative Example.

Examples 22-29

Photoresist compositions were prepared by dissolving solid components in solvents using the materials and proportions set forth in Table 2 to a total solids content of 1.5 wt %. The resulting mixtures were shaken on a mechanical shaker and then filtered through a PTFE disk-shaped filter wafer was generated and $E_0$ determined from the contrast curves as described above. An additional contrast curve for each wafer was generated by plotting normalized photoresist layer thickness in the exposed regions vs. Log dose. Contrast (γ) was determined from the normalized contrast curve as the slope between the point of 80% and 20% photoresist film thickness. The results are shown in Table 2.

TABLE 2

| Example | Photoresist Composition | Polymer | PAG | Base 1 | Base 2 | Solvent* | $E_0$ (mJ/cm$^2$) | γ |
|---|---|---|---|---|---|---|---|---|
| 22 | PR-12 | P1 [83.06] | A1 [15.20] | Q1 [0.50] | Q2 [1.24] | S1/S2 | 14.1 | 15.4 |
| 23 | PR-13 | P1 [79.94] | A3 [18.38] | Q1 [0.48] | Q2 [1.20] | S1/S2 | 10.9 | 18.1 |
| 24 | PR-14 | P1 [81.47] | A2 [16.83] | Q1 [0.48] | Q2 [1.22] | S1/S2 | 12.8 | 10.6 |
| 25 | PR-15 | P1 [78.76] | A6 [19.59] | Q1 [0.47] | Q2 [1.18] | S1/S2 | 12.7 | 11.3 |
| 26 | PR-16 | P1 [79.82] | A4 [18.50] | Q1 [0.48] | Q2 [1.20] | S1/S2 | 15.9 | 12.6 |
| 27 | PR-17 | P1 [79.68] | A5 [18.65] | Q1 [0.48] | Q2 [1.19] | S1/S2 | 12.9 | 15.9 |
| 28 | PR-18 | P1 [77.94] | A7 [20.42] | Q1 [0.47] | Q2 [1.17] | S1/S2 | 16.6 | 9.7 |
| 29 (Comp) | PR-19 | P1 [82.78] | C2 [15.48] | Q1 [0.50] | Q2 [1.24] | S1/S2 | 17.2 | 8.8 |

Amounts for solids components provided in wt % based on total solids;
S1 = propylene glycol monomethyl ether acetate;
S2 = methyl 2-hydroxyisobutyrate;
*S1/S2 solvent blend is 1:1 (wt/wt);
Comp = Comparative Example.

Examples 30-34

Photoresist compositions were prepared by dissolving solid components in solvents using the materials and proportions set forth in Table 3 to a total solids content of 4.3 wt %. The resulting mixtures were shaken on a mechanical shaker and then filtered through a PTFE disk-shaped filter having a 0.2 micron pore size. 200 mm silicon wafers overcoated with a BARC stack (60 nm thick AR™3 antireflectant over 80 nm thick AR™40A antireflectant [DuPont Electronics & Imaging]) were each spin-coated with a respective photoresist composition on a TEL Clean Track ACT 8 wafer track and softbaked at 110° C. for 60 seconds to provide a photoresist layer with a thickness of 120 nm. The wafers were each exposed with 248 nm radiation on a Canon FPA-5000 ES4 scanner (NA=0.8, Outer Sigma=0.85, Inner Sigma=0.57) using a mask having 200 nm diameter/ 400 nm pitch 1:1 contact hole patterns. The wafers were post-exposure baked at 100° C. for 60 seconds, developed with MF™-CD26 TMAH developer (DuPont Electronics & Imaging) for 60 seconds, rinsed with deionized water, and dried. Critical dimension (CD) measurements of the formed contact hole patterns were made with a Hitachi S-9380 CD SEM. Sizing energy ($E_{size}$), exposure latitude (EL), and CD uniformity (3σ) (CDU) were determined based on the CD measurements. Sizing energy is the irradiation energy at which the target 200 nm diameter/400 nm pitch contact hole pattern was resolved. Exposure latitude is the difference in exposure energy required to print contact holes at plus and minus 10% of the target diameter, normalized by the sizing energy. The results are shown in Table 3.

TABLE 3

| Example | Photoresist Composition | Polymer | PAG | Base | Solvent* | $E_{size}$ (mJ/cm$^2$) | EL (%) | CDU (nm) |
|---|---|---|---|---|---|---|---|---|
| 30 | PR-20 | P1 [80.10] | A1 [18.30] | Q2 [1.60] | S1/S2 | 103.437 | 23.834 | 5.45 |
| 31 | PR-21 | P1 [79.88] | A4 [18.52] | Q2 [1.60] | S1/S2 | 118.186 | 27.457 | 5.15 |
| 32 | PR-22 | P1 [78.82] | A6 [15.60] | Q2 [1.57] | S1/S2 | 96.399 | 23.852 | 5.31 |
| 33 | PR-23 | P1 [78.0] | A7 [20.44] | Q2 [1.56] | S1/S2 | 126.198 | 25.01 | 4.96 |
| 34 (Comp) | PR-24 | P1 [80.23] | C1 [18.17] | Q2 [1.60] | S1/S2 | 110.633 | 25.262 | 5.71 |

Amounts for solids components provided in wt % based on total solids;
S1 = propylene glycol monomethyl ether acetate;
S2 = methyl 2-hydroxyisobutyrate;
*S1/S2 solvent blend is 1:1 (wt/wt);
Comp = Comparative Example.

Examples 35-36

Photoresist compositions were prepared by dissolving solid components in solvents using the materials and proportions set forth in Table 4 to a total solids content of 1.55 wt %. The resulting mixtures were shaken on a mechanical shaker and then filtered through a PTFE disk-shaped filter having a 0.2 micron pore size. 200 mm silicon wafers overcoated with a ~50 Å thick organic BARC layer was diced into coupons. Each coupon was spin-coated with a respective photoresist composition and softbaked at 110° C. for 90 seconds to provide a photoresist layer with a thickness of 40 nm. The photoresist-coated coupons were exposed to e-beam radiation with a JEOL Ltd. JBX-9500FS electron beam lithography system to print 35 nm diameter/70 nm pitch 1:1 contact hole patterns. The coupons were post-exposure baked at 90° C. for 60 seconds, developed with MF™-CD26 TMAH developer (DuPont Electronics & Imaging) for 45 seconds, rinsed with deionized water, and dried. Scanning electron microscopy was performed with a Hitachi S-9380 CD SEM to collect images and analyze printed patterns. CD measurements of the contact hole patterns were made based on the SEM images using Fractilia MetroLER metrology software. Sizing energy ($E_{size}$) and CD uniformity (3σ) (CDU) were determined based on the measurements. The sizing energy is the irradiation energy at which the target 35 nm diameter contact hole pattern was resolved. CDU was determined based on CDs of 35 contact holes. The results are shown in Table 4.

TABLE 4

| Example | Photoresist Composition | Polymer | PAG | Base 1 | Base 2 | Solvent* | $E_{size}$ (μC/cm²) | CDU (nm) |
|---|---|---|---|---|---|---|---|---|
| 35 | PR-25 | P1 [59.0] P2 [19.67] | PAG-C1 [19.67] | Q1 [0.48] | Q2 [1.18] | S1/S2 | 250 | 1.1 |
| 36 (Comp) | PR-26 | P1 [60.05] P2 [20.02] | PAG-A1 [18.25] | Q1 [0.48] | Q2 [1.20] | S1/S2 | 250 | 1.4 |

Amounts for solids components provided in wt % based on total solids;
S1 = propylene glycol monomethyl ether acetate;
S2 = methyl 2-hydroxyisobutyrate;
*S1/S2 solvent blend is 1:1 (wt/wt);
Comp = Comparative Example.

What is claimed is:

1. A photoacid generator, comprising a moiety of formula (1):

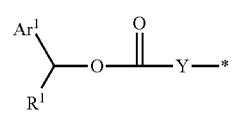

wherein: $Ar^1$ is a substituted or unsubstituted aryl group; $R^1$ is an alkyl or aryl group, each of which may be substituted or unsubstituted, wherein $Ar^1$ and $R^1$ are optionally connected together by a single bond or a divalent linking group to form a ring; Y is a single bond or a divalent group; and * is the point of attachment of the moiety to another atom of the photoacid generator, wherein the photoacid generator is non-ionic.

2. The photoacid generator of claim 1, wherein the non-ionic photoacid generator is chosen from nitrobenzyl derivatives, diazomethane derivatives, sulfonic acid ester derivatives, glyoxime derivatives, β-ketosulfone derivatives, disulfone derivatives, nitrobenzyl sulfonate derivatives, imido-yl sulfonate-derivatives, oxime sulfonate derivatives, imino sulfonate derivatives, and triazine derivatives.

3. The photoacid generator of claim 1, wherein the photoacid generator is in polymeric form.

4. A photoresist composition, comprising a photoacid generator of claim 1 and a solvent.

5. The photoresist composition of claim 4, wherein the photoresist composition comprises an acid-sensitive polymer.

6. A pattern formation method, comprising:
 (a) forming a photoresist layer from a photoresist composition of claim 4 on a substrate;
 (b) exposing the photoresist layer to activating radiation; and
 (c) developing the exposed photoresist layer to provide a resist relief image.

* * * * *